United States Patent [19]
Taylor

[11] 4,152,136
[45] May 1, 1979

[54] 3-PHENYL-5-SUBSTITUTED-4(1H)-PYRIDONES(THIONES)

[75] Inventor: Harold M. Taylor, Indianapolis, Ind.

[73] Assignee: Eli Lilly and Company, Indianapolis, Ind.

[21] Appl. No.: 810,219

[22] Filed: Jun. 27, 1977

Related U.S. Application Data

[63] Continuation-in-part of Ser. No. 591,661, Jul. 3, 1975, abandoned, which is a continuation-in-part of Ser. No. 501,424, Aug. 28, 1974, abandoned.

[51] Int. Cl.$^2$ .................... C07D 213/68; A01N 9/12; A01N 9/22
[52] U.S. Cl. .......................................... 71/90; 71/94; 546/288; 546/287; 546/283; 546/284; 546/294; 546/296; 546/297; 546/298; 546/299; 546/300; 546/301; 546/302; 546/303; 546/290
[58] Field of Search .................. 260/294.8 F, 294.8 R, 260/294.8 D, 294.8 G, 297.2, 295 R, 294.9, 296 R, 295.5 R; 71/90, 94

[56] References Cited

U.S. PATENT DOCUMENTS 4,051,142  9/1977  Carlson .................................. 71/94

FOREIGN PATENT DOCUMENTS 2241665  3/1973  Fed. Rep. of Germany.

*Primary Examiner*—John M. Ford
*Attorney, Agent, or Firm*—Joseph A. Jones; Arthur R. Whale

[57] ABSTRACT

A class of 3-phenyl-4(1H)-pyridones and pyridinethiones are broad-spectrum herbicides. The new compounds are characterized by a small substituent on the nitrogen, and usually bear a 5-substituent chosen from a class described herein. The phenyl ring may be substituted. The compounds are effective herbicides when applied both before and after the emergence of weeds, and are particularly useful for the control of weeds in cotton and rice cropland.

272 Claims, No Drawings

3-PHENYL-5-SUBSTITUTED-4(1H)-PYRIDONES(THIONES)

CROSS-REFERENCE

This application is a continuation-in-part of my copending application, Ser. No. 591,661, filed July 3, 1975, now abandoned which is a continuation-in-part of my then copending application. Ser. No. 501,424, filed Aug. 28, 1974, now abandoned.

BACKGROUND OF THE INVENTION

This invention belongs to the field of agriculture chemistry, and provides to the art new preemergence, postemergence, and aquatic herbicides, and methods for the use of the compounds for the control of weeds. Since the control of weeds is known to be a vital step in the maximization of crop yields, herbicides are now established as vital tools of the farmer and new and improved herbicidal compounds are in constant demand.

Despite the great amount of research which has been performed in the field of agricultural chemistry, active compounds closely related to the compounds of the present invention have not been previously discovered. The polyhalopyridones, which have two or more chlorine atoms as well as other alkyl and halo substituents on the pyridine ring, are known herbicides, but are obviously quite distinct from the present invention.

The organic chemical art has explored the pyridones rather extensively. For example, Ishibe et al., J. Am. Chem. Soc. 95, 3396–3397 (1973), disclosed a rearrangement of 3,5-diphenyl-1,2,6-trimethyl-4(1H)-pyridone. Such compounds, however, are not herbicides. Leonard et al., J. Am. Chem. Soc. 77, 1852–1855 (1955), taught the synthesis of 3,5-dibenzyl-1-methyl-4(1H)-pyridones, which compounds also have no herbicidal activity. The same principal author also disclosed 3,5-di(substituted-benzylidene)tetrahydro-4-pyridones, J. Am. Chem. Soc. 79, 156–160 (1957).

Light et al., J. Org. Chem. 25, 538–546 (1960), taught a number of 4-pyridone compounds including 2,6-diphenyl-1-methyl-4(1H)-pyridone, and related compounds bearing phenyl-ring substituents, none of which are herbicidally active.

An interesting recent article was published by El-Kholy et al. in J. Hetero. Chem. 10, 665–667 (published September 7, 1973). El-Kholy described a synthesis of 3,5-diphenyl-1-methyl-4(1H)-pyridone and related compounds by the reaction with methylamine of the sodium salt of 1,5-dihydroxy-2,4-diphenyl-1,4-pentadien-3-one.

A counterpart of the parent application Ser. No. 591,661, has been patented as Belgian Patent 832,702 (1976).

Articles reporting the herbicidal use of compounds of this invention include the following:

Berard and Rainey, Weed Sci. Soc. of Am. Abstracts 28, p. 13 (1977);

Waldrep and Taylor, J. Agric. Food Chem. 24, 1250-51 (1976);

Waldrep and Taylor, Weed Sci. Soc. of Am. Abstracts 266, p. 109 (1977);

Webster, Proc. Southern Weed Sci. Soc. 30, 103–12 (1977);

Wills, Proc. Southern Weed Sci. Soc. 30, 113–18 (1977).

SUMMARY OF THE INVENTION

A series of new 3-phenyl-4(1H)-pyridones(thiones) are herbicides which are active against an unusually wide range of weeds. New methods and compositions using the compounds for the control of weeds, which methods are particularly useful in cotton and rice cropland, are also disclosed. The new compounds are of the formula

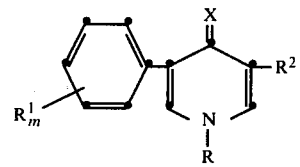

wherein
X represents oxygen or sulfur;
R represents $C_1$–$C_3$ alkyl,
$C_1$–$C_3$ alkyl substituted with halo, cyano, carboxy or methoxycarbonyl,
$C_2$–$C_3$ alkenyl,
$C_2$–$C_3$ alkynyl,
$C_1$–$C_3$ alkoxy,
acetoxy or
dimethylamino,
provided that R comprises no more than 3 carbon atoms;
the $R^1$ group independently represent halo,
$C_1$–$C_8$ alkyl,
$C_1$–$C_8$ alkyl substituted with halo,
$C_1$–$C_8$ alkyl monosubstituted with phenyl, cyano or $C_1$–$C_3$ alkoxy,
$C_2$–$C_8$ alkenyl,
$C_2$–$C_8$ alkenyl substituted with halo,
$C_2$–$C_8$ alkynyl,
$C_2$–$C_8$ alkynyl substituted with halo,
$C_3$–$C_6$ cycloalkyl,
$C_4$–$C_6$ cycloalkenyl,
$C_4$–$C_8$ cycloalkylalkyl,
$C_1$–$C_3$ alkanoyloxy,
$C_1$–$C_3$ alkylsulfonyloxy,
phenyl,
phenyl monosubstituted with halo, $C_1$–$C_3$ alkyl, $C_1$–$C_3$ alkoxy or nitro,
nitro,
cyano,
carboxy,
hydroxy,
$C_1$–$C_3$ alkoxycarbonyl,
—O—$R^3$,
—S—$R^3$,
—SO—$R^3$ or
—$SO_2$—$R^3$;
$R^3$ represents $C_1$–$C_{12}$ alkyl,
$C_1$–$C_{12}$ alkyl substituted with halo,
$C_1$–$C_{12}$ alkyl monosubstituted with phenyl, cyano or $C_1$–$C_3$ alkoxy,
phenyl,
phenyl monosubstituted with halo, $C_1$–$C_3$ alkyl, $C_1$–$C_3$ alkoxy or nitro,
$C_3$–$C_6$ cycloalkyl,
$C_4$–$C_8$ cycloalkylalkyl,
$C_2$–$C_{12}$ alkenyl,
$C_2$–$C_{12}$ alkenyl substituted with halo,
$C_2$–$C_{12}$ alkynyl or $C_2-C_{12}$ alkynyl substituted with halo,
provided that $R^3$ comprises no more than 12 carbon atoms;

$R^2$ represents halo,
hydrogen,
cyano,
$C_1-C_3$ alkoxycarbonyl,
$C_1-C_6$ alkyl,
$C_1-C_6$ alkyl substituted with halo or $C_1-C_3$ alkoxy,
$C_2-C_6$ alkenyl,
$C_2-C_6$ alkenyl substituted with halo or $C_1-C_3$ alkoxy,
$C_2-C_6$ alkynyl,
$C_3-C_6$ cycloalkyl,
$C_3-C_6$ cycloalkyl substituted with halo, $C_1-C_3$ alkyl or $C_1-C_3$ alkoxy,
$C_4-C_6$ cycloalkenyl,
$C_4-C_8$ cycloalkylalkyl,
phenyl—$C_1-C_3$ alkyl,
furyl,
naphthyl,
thienyl,
—O—$R^4$,
—S—$R^4$,
—SO—$R^4$,
—SO$_2$—$R^4$ or

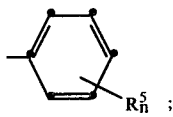

$R^4$ represents $C_1-C_3$ alkyl,
$C_1-C_3$ alkyl substituted with halo,
$C_2-C_3$ alkenyl,
$C_2-C_3$ alkenyl substituted with halo,
benzyl,
phenyl or
phenyl substituted with halo, $C_1-C_3$ alkyl or $C_1-C_3$ alkoxy;

the $R^5$ groups independently represent halo,
$C_1-C_8$ alkyl,
$C_1-C_8$ alkyl substituted with halo,
$C_1-C_8$ alkyl monosubstituted with phenyl, cyano or
$C_1-C_3$ alkoxy,
$C_2-C_8$ alkenyl,
$C_2-C_8$ alkenyl substituted with halo,
$C_2-C_8$ alkynyl,
$C_2-C_8$ alkynyl substituted with halo,
$C_3-C_6$ cycloalkyl,
$C_4-C_6$ cycloalkenyl,
$C_4-C_8$ cycloalkylalkyl,
$C_1-C_3$ alkanoyloxy,
$C_1-C_3$ alkylsulfonyloxy,
phenyl,
phenyl monosubstituted with halo, $C_1-C_3$ alkyl, $C_1-C_3$ alkoxy or nitro,
nitro,
cyano,
carboxy,
hydroxy,
$C_1-C_3$ alkoxycarbonyl,
—O—$R^6$,
—S—$R^6$,
—SO—$R^6$ or
—SO$_2$—$R^6$;
$R^6$ represents $C_1-C_{12}$ alkyl,
$C_1-C_{12}$ alkyl substituted with halo,
$C_1-C_{12}$ alkyl monosubstituted with phenyl, cyano or
$C_1-C_3$ alkoxy,
phenyl,
phenyl monosubstituted with halo,
$C_1-C_3$ alkyl, $C_1-C_3$ alkoxy or nitro,
$C_3-C_6$ cycloalkyl,
$C_4-C_8$ cycloalkylalkyl,
$C_2-C_{12}$ alkenyl,
$C_2-C_{12}$ alkenyl substituted with halo,
$C_2-C_{12}$ alkynyl or
$C_2-C_{12}$ alkynyl substituted with halo, provided that $R^6$ comprises no more than 12 carbon atoms;

m and n independently represent 0–2; and the acid addition salts thereof.

A preferred group of compounds comprises those wherein m represents 1, and the single $R^1$ group is located at the meta position of the phenyl ring to which it is attached. Highly preferred compounds are those of the above group wherein $R^1$ represents trifluoromethyl.

A particularly preferred class of compounds are those of the formula

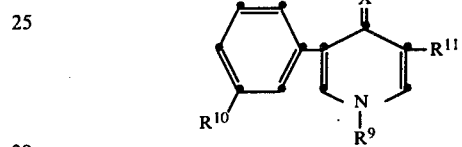

wherein
X represents oxygen or sulfur;
$R^9$ represents $C_1-C_3$ alkyl;
$R^{10}$ represents hydrogen, trifluoromethyl, $C_1-C_3$ alkyl, halo, methoxy or methylthio;
$R^{11}$ represents $C_1-C_4$ alkyl, $C_1-C_3$ alkoxy, $C_1-C_3$ alkylthio, phenyl, phenoxy, phenylthio, or phenyl, phenoxy or phenylthio monosubstituted with trifluoromethyl, $C_1-C_3$ alkyl, halo, methoxy or methylthio.

A further preferred group of compounds are of the formula

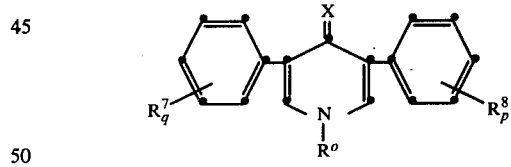

wherein
X represents oxygen or sulfur;
$R°$ represents $C_1-C_3$ alkyl, $C_2-C_3$ alkenyl, acetoxy or methoxy;
q and p independently represent 0–2; the $R^7$ groups independently represent halo, $C_1-C_3$ alkyl, trifluoromethyl or $C_1-C_3$ alkoxy; the $R^8$ groups independently represent halo, $C_1-C_3$ alkyl, trifluoromethyl or $C_1-C_3$ alkoxy, or two $R^8$ groups occupying adjacent o and m positions combine with the phenyl ring to which they are attached to form a 1-naphthyl group.

Within all of the above-described classes of compounds of this invention, the pyridones wherein X represents oxygen are a preferred subclass, and the pyridinethiones wherein X represents sulfur are another preferred subclass. Further preferred subclasses within all of the above classes of compounds are those wherein the 1-substituent, R, R° or R⁹, represents methyl or ethyl, and wherein the 1-substituent represents methyl.

DESCRIPTION OF THE PREFERRED EMBODIMENT

In the above formula, the general chemical terms are used in their normal meanings. For example, the terms $C_1$-$C_3$ alkyl, $C_2$-$C_3$ alkenyl, $C_2$-$C_3$ alkynyl, $C_1$-$C_3$ alkoxy, $C_1$-$C_3$ alkylthio, $C_1$-$C_8$ alkyl, $C_2$-$C_8$ alkenyl, $C_2$-$C_8$ alkynyl, $C_1$-$C_6$ alkyl, $C_2$-$C_6$ alkenyl and $C_2$-$C_6$ alkynyl refer to such groups as methyl, ethyl, isopropyl, vinyl, allyl, methoxy, isopropoxy, methylthio, isopropylthio, propargyl, isobutyl, hexyl, octyl, 1,1-dimethylpentyl, 2-octenyl, pentyl, 3-hexynyl, 1-ethyl-2-hexenyl, 3-octynyl, 5-heptenyl, 1-propyl-3-butynyl and crotyl.

The terms $C_3$-$C_6$ cycloalkyl and $C_4$-$C_6$ cycloalkenyl refer to such groups as cyclopropyl, cyclobutyl, cyclohexyl, cyclobutenyl, cyclopentenyl and cyclohexadienyl.

The term $C_4$-$C_8$ cycloalkylalkyl refers to such groups as cyclopropylmethyl, cyclobutylmethyl, cyclohexylmethyl and cyclohexylethyl.

The term $C_1$-$C_3$ alkanoyloxy refers to groups such as formyloxy, acetoxy and propionyloxy.

The term $C_1$-$C_3$ alkoxycarbonyl refers to groups such as methoxycarbonyl, ethoxycarbonyl and isopropoxycarbonyl.

The term $C_1$-$C_3$ alkylsulfonyloxy refers to such groups as methylsulfonyloxy and propylsulfonyloxy.

The term halo refers to fluoro, chloro, bromo, and iodo.

The compounds described above can form acid addition salts, and such salts are useful embodiments of the invention. The preferred salts are the hydrohalides such as hydroiodides, hydrobromides, hydrochlorides and hydrofluorides. Salts of the sulfonic acids are also particularly desirable. Such salts include sulfonates, methylsulfonates and toluenesulfonates.

Although the above general description of the compounds is believed to describe them unambiguously, a group of exemplary compounds of the invention will be named below to assure that the invention is understood by those skilled in the art.

1-methyl-3,5-bis(3-methoxyphenyl)-4(1H)-pyridinethione 1-ethyl-3-(4-ethoxyphenyl)-5-phenyl-4(1H)-pyridinethione 3-(3,5-diiodophenyl)-5-(3-propylphenyl)-1-propyl-4(1H)-pyridinethione 3-(2,6-dimethylphenyl)-1-isopropyl-5-(1-naphthyl)-4(1H)-pyridone 3-(4-methylphenyl)-5-phenyl-1-vinyl-4(1H)-pyridone, hydroiodide 1-allyl-3-(3-chlorophenyl)-5-(2,3-diethoxyphenyl)-4(1H)-pyridinethione 3,5-diphenyl-1-ethyl-4(1H)-pyridinethione 3-(3,5-difluorophenyl)-1-methoxy-5-phenyl-4(1H)-pyridone 1-acetoxy-3-(3,5-diethylphenyl)-5-(2,4-diethylphenyl)-4(1H)-pyridinethione 1-allyl-3-(1-naphthyl)-5-(4-propoxyphenyl)-4(1H)-pyridinethione 1-propyl-3-(4-trifluoromethylphenyl)-5-(3-trifluoromethylphenyl)-4(1H)-pyridone 3-(2,6-difluorophenyl)-5-(3-iodophenyl)-1-vinyl-4(1H)-pyridone 3-(3,5-dibromophenyl)-5-(3-isopropoxyphenyl)-1-propyl-4(1H)-pyridone 1-methyl-3-phenyl-5-(2-propylphenyl)-4(1H)-pyridinethione, hydrochloride 3-(3-bromophenyl)-1-methyl-5-phenyl-4(1H)-pyridone 3-(4-chlorophenyl)-5-(2,4-dimethoxyphenyl)-1-propyl-4(1H)-pyridone 1-allyl-3-phenyl-5-(3-trifluoromethylphenyl)-4(1H)-pyridinethione 1-acetoxy-3,5-diphenyl-4(1H)-pyridinethione 3-(2-iodophenyl)-5-(3-isopropylphenyl)-1-methoxy-4(1H)-pyridinethione 3-(2-iodo-4-methylphenyl)-5-phenyl-1-vinyl-4(1H)-pyridinethione 1-acetoxy-3-(4-chlorophenyl)-5-(1-naphthyl)-4(1H)-pyridone 3,5-diphenyl-1-isopropyl-4(1H)-pyridinethione 3-(3-bromo-5-ethylphenyl)-5-(3-methylphenyl)-1-propyl-4(1H)-pyridinethione 3-(4-ethoxy-2-fluorophenyl)-1-methoxy-5-phenyl-4(1H)-pyridone 1-allyl-3,5-bis(3-ethyl-4-methoxyphenyl)-4(1H)-pyridone 3-(2-iodo-4-propylphenyl)-1-methyl-5-(4-trifluoromethylphenyl)-4(1H)-pyridinethione 1-methyl-3-(3-methyl-5-propylphenyl)-5-phenyl-4(1H)-pyridinethione 3-(2-chloro-4-iodophenyl)-5-(3-fluorophenyl)-1-propyl-4(1H)-pyridinethione 3-(3-chlorophenyl)-5-[2,4-bis(trifluoromethyl)phenyl]-1-methoxy-4(1H)-pyridone 3-benzyloxy-1-chloromethyl-5-(3-ethynylphenyl)-4(1H)-pyridone 3-benzylthio-1-(2-bromoethyl)-5-(2,4-dimethylphenyl)-4(1H)-pyridone 3-benzylsulfinyl-1-ethyl-5-(3-fluoro-5-propylphenyl)-4(1H)-pyridone 3-benzylsulfonyl-5-(3-octylphenyl)-1-propyl-4(1H)-pyridone 3-(2-butylphenyl)-1-trifluoromethyl-4(1H)-pyridone, hydrobromide 1-(2-chloroethyl)-3-cyano-5-phenyl-4(1H)-pyridinethione 3-(3-hexylphenyl)-1-methyl-5-(2-methylphenyl)-4(1H)-pyridone 1-(3,3-dibromopropyl)-3-(2,4-dichlorophenyl)-5-methyl-4(1H)-pyridone 3-(2,4-dimethylphenyl)-5-methoxycarbonyl-1-methyl-4(1H)-pyridone 1-methyl-3-[3-(1-propylpentyl)phenyl]-5-propyl-4(1H)-pyridone 1-(2-cyanoethyl)-3-(3-octyl-4-methylphenyl)-5-propoxycarbonyl-4(1H)-pyridone 3-[3-(2-ethylpentyl)phenyl]-1-carboxymethyl-5-(3-trifluoromethylphenyl)-4(1H)-pyridone 3-(2-chloromethylphenyl)-1-methoxycarbonylmethyl-4(1H)-pyridone 3,5-diphenyl-1-ethynyl-4(1H)-pyridinethione 3-(4-heptafluoropropylphenyl)-5-hexyl-1-methyl-4(1H)-pyridinethione 3-(3,5-diethylphenyl)-1-propargyl-5-[3-(5,5-dibromopentyl)phenyl]-4(1H)-pyridone 3-(2,4-dipropylphenyl)-1-methyl-5-trifluoromethyl-4(1H)-pyridone 3-(4-benzylphenyl)-1-ethoxy-5-(2-fluoroethyl)-4(1H)-pyridone 3-(2-chloroethyl)-5-[4-(2,2-diiodooctyl)phenyl]-1-methoxy-4(1H)-pyridinethione 3-(3-chloro-2-methoxyphenyl)-5-(1,1-dibromopentyl)-1-methyl-4(1H)-pyridone 3-(6-iodohexyl)-1-isopropoxy-5-phenyl-4(1H)-pyridinethione 3-(3-hexylphenyl)-5-methoxymethyl-1-methyl-4(1H)-pyridone 1-dimethylamino-3,5-bis(3-trifluoromethylphenyl)-4(1H)-pyridinethione 1-methyl-3-[4-(4-phenylhexyl)phenyl]-5-(3-propylphenyl)-4(1H)-pyridone 3-(3-hexenyl)-5-[2-(2-methoxyethyl)phenyl]-1-methyl-4(1H)-pyridinethione 3-(2,2-dichlorovinyl)-1-methyl-5-[3-(3-propoxyheptyl)phenyl]-4(1H)-pyridone 3-(2-bromo-1-butenyl)-5-[3-(6-ethoxyheptyl)phenyl]-1-ethoxy-4(1H)-pyridone 3-(2-iodo-1-hexenyl)-1-methyl-5-(3-vinylphenyl)-4(1H)-pyridinethione 3-(4-allylphenyl)-1-dimethylamino-5-phenyl-4(1H)-pyridinethione 3-(2-methoxyallyl)-1-methyl-5-(4-trifluoromethylphenyl)-4(1H)-pyridinethione 3-(4-ethoxy-2-pentenyl)-5-[2-(2,4-hexadienyl)phenyl]-1-methoxy-4(1H)-pyridone 1-methoxycarbonylmethyl-3-[3-(3-octenyl)phenyl]-5-phenyl-4(1H)-pyridone, methanesulfonate 3-[3-(2-hexenyl)phenyl]-1-methyl-5-(3-propylphenyl)-4(1H)-pyridinethione 3-(2-ethyl-3-fluorophenyl)-5-ethynyl-1-methyl-4(1H)-pyridinethione 3-(2-butynyl)-5-(2,4-diiodophenyl)-1-ethoxy-4(1H)-pyridone 3-[4-(2,6-dibromo-2-heptenyl)phenyl]-1,5-dimethyl-4(1H)-pyridone 3-(2-hexenyl)-1-methyl-5-[3-(1,1,2,2-tetrachloro-4-octenyl)phenyl]-4(1H)-pyridone 3-cyclopropyl-5-[2-(2-fluoro-1-pentenyl)phenyl]-1-methoxy-4(1H)-pyridinethione 1-(2-chloroethyl)-3-[4-(2-cyanoethyl)phenyl]-4(1H)-pyridone 1-methyl-3-(2-propoxyethyl)-5-phenyl-4(1H)-pyridinethione, hydrofluoride 3-(6-ethoxyhexyl)-5-(3-ethyl-5-iodophenyl)-1-(3-iodopropyl)-4(1H)-pyridone 1-methyl-3-phenyl-5-vinyl-4(1H)-pyridinethione 3-allyl-5-[4-(3-cyanohexyl)phenyl]-1-propoxy-4(1H)-pyridinethione 3-[4-(8-cyanooctyl)phenyl]-1-methyl-5-(2-pentenyl)-4(1H)-pyridone 3-cyclobutyl-5-[4-(2-iodovinyl)phenyl]-1-propoxy-4(1H)-pyridone 3-cyclohexyl-5-(3-ethynylphenyl)-1-iodomethyl-4(1H)-pyridinethione 1-(1-carboxyethyl)-3-(2-chlorocyclopropyl)-5-[3-(3-chloropropargyl)phenyl]-4(1H)-pyridone 3-(2,2-dibromocyclohexyl)-1-methyl-5-[2-(3-pentynyl)phenyl]-4(1H)-pyridinethione 3-[4-(1,1-dibromo-4-pentynyl)phenyl]-1-isopropoxy-5-(2-methylcyclobutyl)-4(1H)-pyridone 3-(2,4-diiodocyclopentyl)-1-ethyl-5-[4-(2-octynyl)phenyl]-4(1H)-pyridone 1-acetoxy-3-(4-propylcyclohexyl)-5-[3-(6,6,6-trifluoro-2-hexynyl)phenyl]-4(1H)-pyridinethione 3-[3-(4-octynyl)phenyl]-5-(2-methoxycyclopropyl)-1-methyl-4(1H)-pyridinethione 3-[2-(1,1-dichloro-4-heptynyl)phenyl]-5-(4-methoxycyclohexyl)-1-methoxy-4(1H)-pyridone 3-(4-cyclopropylphenyl)-1-(2-methoxycarbonylmethyl)-5-(2-propoxycyclobutyl)-4(1H)-pyridinethione 3-(2-cyclobutenyl)-5-(3-cyclopentylphenyl)-1-ethoxy-4(1H)-pyridinethione 3-(3-cyclohexenyl)-5-(3-cyclohexylphenyl)-1-dimethylamino-4(1H)-pyridone 3-[4-(1-cyclobutenyl)phenyl]-5-methoxy-1-vinyl-4(1H)-pyridone, toluenesulfonate 3-chloromethoxy-1-cyanomethyl-5-(2-formyloxyphenyl)-4(1H)-pyridinethione 1-(2-carboxyethyl)-3-(3-propionyloxyphenyl)-5-trifluoromethoxy-4(1H)-pyridinethione 3-[4-(2-cyclohexenyl)phenyl]-5-isopropoxy-1-trifluoromethyl-4(1H)-pyridone 3-(1,2-dibromopropoxy)-1-ethoxy-5-(2-methylsulfonyloxyphenyl)-4(1H)-pyridinethione 1-dichloromethyl-3-(2-iodoethoxy)-5-(4-isopropylsulfonyloxyphenyl)-4(1H)-pyridone 3-(3-biphenylyl)-1-methyl-5-vinyloxy-4(1H)-pyridinethione 3-allyloxy-5-[4-(2-chlorophenyl)phenyl]-1-isopropyl-4(1H)-pyridone, hydrochloride 3-(2,2-dichlorovinyloxy)-5-[2-(3-iodophenyl)phenyl]-1-methyl-4(1H)-pyridone 3-(2-bromoallyloxy)-5-[3-(3-bromophenyl)phenyl]-1-vinyl-4(1H)-pyridone 1-allyl-3-[4-(2-methylphenyl)phenyl]-5-(3,3,3-trifluoro-1-propenyloxy)-4(1H)-pyridone 1-methoxy-3-phenoxy-5-[3-(4-propylphenyl)phenyl]-4(1H)-pyridone 3-(2-chlorophenoxy)-5-[4-methoxyphenyl)phenyl]-1-propargyl-4(1H)-pyridone 3-(4-bromophenoxy)-5-[4-(2-ethoxyphenyl)phenyl]-1-ethyl-4(1H)-pyridone 3-(2-iodophenoxy)-5-[3-(4-isopropoxyphenyl)phenyl]-1-methoxycarbonylmethyl-4(1H)-pyridone 1-cyanomethyl-3-(2-methylphenoxy)-5-[3-(4-nitrophenyl)phenyl]-4(1H)-pyridinethione 1-methyl-3-(4-nitrophenyl)-5-(3-propylphenoxy)-4(1H)-pyridone 3-(4-cyanophenyl)-1-ethoxy-5-(2-methoxyphenoxy)-4(1H)-pyridone 3-(3-carboxyphenyl)-5-(2-ethoxyphenoxy)-1-isopropyl-4(1H)-pyridone, hydrofluoride 1-(2-carboxyethyl)-3-(4-hydroxyphenyl)-5-(3-propoxyphenoxy)-4(1H)-pyridone 3-benzyl-5-(2-methoxycarbonylphenyl)-1-methyl-4(1H)-pyridone 1-dimethylamino-3-(3-phenylpropyl)-5-(4-propoxycarbonylphenyl)-4(1H)-pyridone 3-(3-butoxyphenyl)-5-(2-furyl)-1-trifluoromethyl-4(1H)-pyridone 3-(1-ethylpentyl)-5-(3-furyl)-1-methyl-4(1H)-pyridone 3-[4-(2-propylhexyloxy)phenyl]-1-methoxycarbonylmethyl-5-(2-thienyl)-4(1H)-pyridone 1-methyl-3-(4-nonyloxyphenyl)-5-(3-thienyl)-4(1H)-pyridinethione 1-methyl-3-[4-(2-propylnonyloxy)phenyl]-5-(4-trifluoromethylphenyl)-4(1H)-pyridinethione 3-(3,5-diethylphenyl)-1-ethyl-5-(4-trifluoromethoxyphenyl)-4(1H)-pyridinethione 3-(2,4-divinylphenyl)-5-[4-(2-fluoroethoxy)phenyl]-1-isopropoxy-4(1H)-pyridinethione 3-[3-(5,5-dibromopentoxy)phenyl]-5-(3,5-dicyclopropylphenyl)-1-ethyl-4(1H)-pyridone 3-(2,4-dimethoxyphenyl)-1-(2-methoxycarbonylmethyl)-5-[2-(12-iodododecyloxy)phenyl]-4(1H)-pyridinethione 3-(4-benzyloxyphenyl)-1-cyanomethyl-5-[3,5-di-(isopropenyl)phenyl]-4(1H)-pyridinethione 3-(2,6-dinitrophenyl)-1-methoxy-5-[5-phenylpentoxy)phenyl]-4(1H)-pyridone 3-(2,4-diformyloxyphenyl)-1-ethoxy-5-[4-(3-phenylhexyloxy)phenyl]-4(1H)-pyridinethione 3-[4-(3-cyanopropoxy)phenyl]-5-(3-ethoxy-5-iodophenyl)-1-methyl-4(1H)-pyridinethione 3-[4-(7-cyanoheptyloxy)phenyl]-1-ethyl-5-phenyl-4(1H)-pyridinethione 3-[3-(4-cyanoundecyloxy)phenyl]-5-[2,4-di(2-ethoxyethyl)phenyl]-1-methoxy-4(1H)-pyridinethione 3-[2-(2-ethoxyethoxy)phenyl]-1-(2-iodoethyl)-5-(3,4-diacetoxyphenyl)-4(1H)-pyridinethione 3-(4-butoxy-2-difluoromethylphenyl)-1-cyanomethyl-5-[3-(6-methoxyhexyloxy)phenyl]-4(1H)-pyridone 3-(2-cyclohexyl-4-ethylphenyl)-1-methoxycarbonylmethyl-5-[2-(6-propoxynonyloxy)phenyl]-4(1H)-pyridone 3-[2,4-di(2-pentynyl)phenyl]-1-isopropoxy-5-(2-vinyloxyphenyl)-4(1H)-pyridinethione 3-(2,4-diallyloxyphenyl)-1-(2,2-dichloropropyl)-5-(2-methyl-6-nitrophenyl)-4(1H)-pyridone 3-[3-(2,4-hexadienyloxy)phenyl]-1-isopropyl-5-phenyl-4(1H)-pyridinethione, hydroiodide 1-(2-carboxyethyl)-3-(2,6-dipropylphenyl)-5-[4-(5-dodecenyloxy)phenyl]-4(1H)-pyridinethione 3-[2-(2-chloroallyloxy)phenyl]-1-(2,2-dichloroethyl)-5-(2,4-diethoxyphenyl)-4(1H)-pyridinethione 1-allyl-3-(4-cyano-3-ethoxycarbonylphenyl)-5-[4-(4,4,4-trifluoro-2-butenyloxy)phenyl]-4(1H)-pyridone 1-chloromethyl-3-(3-methylsulfonyloxy-5-vinylphenyl)-5-[3-(2,2-dibromo-3-heptenyloxy)phenyl]-4(1H)-pyridinethione 1-ethoxy-3-[3-(9-iodo-1-nonenyloxy)phenyl]-5-phenyl-4(1H)-pyridone 1-chlorodifluoromethyl-3-[2,4-di(chloromethyl)phenyl]-5-[2-(1,2,3-trichloro-6-dodecenyloxy)phenyl]-4(1H)-pyridinethione 3-[3-(4-chloro-2-butynyloxy)phenyl]-1-ethoxy-5-(3-fluoro-4-isobutoxyphenyl)-4(1H)-pyridone 3-[3-(6,6-dibromo-3-hexynyloxy)phenyl]-1-methyl-5-(3-nitro-4-propylphenyl)-4(1H)-pyridinethione 1-acetoxy-3-(2,4-dibromophenyl)-5-[3-(1,1,2,2-tetrafluoro-3-decynyloxy)phenyl]-4(1H)-pyridone 3-(3-ethynyloxyphenyl)-1-methyl-5-phenyl-4(1H)-pyridinethione, hydrobromide 3-[2-(10-dodecynyloxy)phenyl]-1-methyl-5-(2-propyl-4-propylsulfonyloxyphenyl)-4(1H)-pyridone 3-[2,4-di(3-pentenyl)phenyl]-5-(3-phenoxyphenyl)-1-(1,1,2,2-tetrafluoroethyl)-4(1H)-pyridone 3-[4-(4-fluorophenoxy)phenyl]-1-isopropyl-5-phenyl-4(1H)-pyridinethione 1-(3-chloropropyl)-3-(3-cyanomethyl-5-ethylphenyl)-5-[3-(3-iodophenoxy)phenyl]-4(1H)-pyridone 3-(3-octyl-5-fluorophenyl)-5-[2-(3-ethylphenoxy)phenyl]-1-trifluoromethyl-4(1H)-pyridone 3-(2-ethyl-4-propylsulfonyloxyphenyl)-1-ethynyl-5-[2-(4-isopropylphenoxy)phenyl]-4(1H)-pyridone 1-carboxymethyl-3-(2,4-dinonyloxyphenyl)-5-[3-(4-methoxyphenoxy)phenyl]-4(1H)-pyridone 1-chloromethyl-3-(2,4-difluorophenyl)-5-[2-(3-propoxyphenoxy)phenyl]-4(1H)-pyridone 1-methyl-3-[4-(2-nitrophenoxy)phenyl]-5-phenyl-4(1H)-pyridinethione 3-(3-isobutylthiophenyl)-1-isopropyl-5-phenyl-4(1H)-pyridinethione 3-(3-chloro-4-heptylthiophenyl)-5-[3-(4-cyanopentyl)phenyl]-1-methyl-4(1H)-pyridone 1-methyl-3-phenyl-5-[2-(3-ethylhexylthio)phenyl]-4(1H)-pyridone, hydrofluoride 3-(2-chloro-4-ethylphenyl)-1-ethyl-5-(3-nonylthio-4-vinylphenyl)-4(1H)-pyridone 1-ethynyl-3-phenyl-5-[3-(2-ethylpentylthio)phenyl]-4(1H)-pyridone 1-(2-methoxycarbonylmethyl)-3-[4-(3-iodophenyl)phenyl]-5-(3-trifluoromethylthiophenyl)-4(1H)-pyridinethione 1-acetoxy-3-(3-cyclopentylphenyl)-5-[3-(2-fluoroethylthio)phenyl]-4(1H)-pyridinethione 3-(2-cyano-4-hydroxyphenyl)-1-dimethylamino-5-[3-(5,5-dibromopentylthio)-4-nitrophenyl]-4(1H)-pyridone 3-[4-(4,4-diiodododecylthio)phenyl]-1-methyl-5-phenyl-4(1H)-pyridone 3-(3-benzylthio-5-ethynylphenyl)-1-cyanomethyl-5-(2-hexylphenyl)-4(1H)-pyridinethione 3-[3,5-bis(4-phenylbutylthio)phenyl]-5-(2-methylphenyl)-1-(1,1,2,2-tetrafluoroethyl)-4(1H)-pyridone 3-[2-bromo-4-(6-phenylhexylthio)phenyl]-5-[4-(2-cyanopropylthio)-2-ethylphenyl]-1-methyl-4(1H)-pyridinethione 3-[4-(6-cyanoheptylthio)phenyl]-1-fluoromethyl-4(1H)-pyridone 3-(3-acetoxy-5-ethylphenyl)-5-[2-(8-cyanoundecylthio)phenyl]-1-chlorodifluoromethyl-4(1H)-pyridone 3-(4-benzyl-2-ethoxyethoxyphenyl)-1-(2-carboxyethyl)-5-[3-(2-ethoxyethoxy)-5-propargylphenyl]-4(1H)-pyridone, toluenesulfonate 1-ethyl-3-[4-(6-methoxyhexylthio)phenyl]-5-phenyl-4(1H)-pyridinethione 1-isopropenyl-3-[3-(3-phenylpentyl)phenyl]-5-[4-(6-isopropoxynonylthio)phenyl]-4(1H)-pyridone 3-(2-cyanomethyl-4-vinylthiophenyl)-1-ethyl-5-[2-(7-phenylheptyl)phenyl]-4(1H)-pyridone 3-(3-allylthio-4-methoxymethylphenyl)-5-[2-(6-cyanohexyl)-4-vinylphenyl]-1-methyl-4(1H)-pyridone 1-methoxycarbonylmethyl-3-[3-(2-pentenylthio)phenyl]-5-phenyl-4(1H)-pyridinethione 3-[3-(2-decenylthio)-5-(2,4-hexadienyl)phenyl]-1-ethoxy-5-phenyl-4(1H)-pyridone 3-[4-(1,1-dichloroallylthio)phenyl]-5-[3-(4-octenyl)-2-propylphenyl]-1-trifluoromethyl-4(1H)-pyridone 3-(4-carboxy-2-hydroxyphenyl)-5-[3-(2-chloro-3-butenylthio)-5-nitrophenyl]-1-vinyl-4(1H)-pyridone 3-[4-(5,5-dibromo-3-heptenylthio)phenyl]-1-methyl-5-phenyl-4(1H)-pyridone 3,5-bis[4-(9-iodo-8-nonenylthio)phenyl]-1-isopropyl-4(1H)-pyridinethione 1-ethyl-3-(3-fluorophenyl)-5-[4-(12,12,12-trichloro-2,6-dodecadienylthio)phenyl]-4(1H)-pyridinethione 3-[2-(1-chloropropargylthio)phenyl]-1-dimethylamino-5-[3-(4-pentenyl)-5-methoxycarbonylphenyl]-4(1H)-pyridone 3-[4-(3,3-dibromo-5-hexynylthio)phenyl[-1-methoxy-5-phenyl-4(1H)-pyridone 1-(2-chloropropyl)-3-[2-cyclopropyl-4-(1,1,2,2-tetrafluoro-5-decynylthio)phenyl]-5-phenyl-4(1H)-pyridinethione 1-acetoxy-3-(3-ethynylthiophenyl)-5-(3-ethynyl-5-fluorophenyl)-4(1H)-pyridone 3-[4-(4-decynylthio)-2-methylphenyl]-1-ethoxy-5-(5-fluoro-3-trifluoromethylphenyl)-4(1H)-pyridinethione 1-cyanomethyl-3-(4-phenylthiophenyl)-5-phenyl-4(1H)-pyridinethione, hydrochloride 3-(3-chlorophenyl)-5-[2-(3-fluorophenylthio)phenyl]-1-methyl-4(1H)-pyridone 1-carboxymethyl-3-[3-(2-iodophenylthio)phenyl]-5-(3-methyl-5-methoxycarbonylphenyl)-4(1H)-pyridone 1-(2-chloroethyl)-3-(2,4-diethylphenyl)-5-[4-(4-ethylphenylthio)-2-methoxyphenyl]-4(1H)-pyridone 3-[3-(3-isopropylphenylthio)phenyl]-5-phenyl-1-trifluoromethyl-4(1H)-pyridone 1-acetoxy-3-(4-butylphenyl)-5-[4-(3-methoxyphenylthio)phenyl]-4(1H)-pyridinethione 3-(2-methyl-6-propoxyphenyl)-3-[4-(3-propoxyphenylthio)phenyl]-1-propargyl-4(1H)-pyridone 3-[3-chloro-5-(4-nitrophenylthio)phenyl]-1-methyl-5-(2,4-divinylphenyl)-4(1H)-pyridone 3-(4-butylsulfinylphenyl)-5-phenyl-1-propargyl-4(1H)-pyridone 1-ethyl-3-(3-heptylsulfinylphenyl)-5-(4-propoxycarbonylphenyl)-4(1H)-pyridone 3-(2-carboxyphenyl)-1-dimethylamino-5-[2-hydroxy-4-(2-propylpentylsulfinyl)phenyl]-4(1H)-pyridinethione 1-acetoxy-3-(2-cyano-5-nonylsulfinylphenyl)-5-(3,5-dinitrophenyl)-4(1H)-pyridinethione 1-ethoxy-3-[3-(4-propylnonylsulfinyl)phenyl]-5-phenyl-4(1H)-pyridone 1-methoxy-3-(2-nitrophenyl)-5-(4-trifluoromethylsulfinylphenyl)-4(1H)-pyridinethione 3-(2-ethoxyphenyl)-1-isopropyl-5-[4-(2-fluoroethylsulfinyl)-2-isopropylphenyl]-4(1H)-pyridone 3-[3,5-di(4-chlorophenyl)phenyl]-3-[4-(5,5-dibromopentylsulfinyl)-2-ethoxyphenyl]-1-ethynyl-4(1H)-pyridone 3-[3-(12-iodododecylsulfinyl)phenyl]-5-phenyl-1-propargyl-4(1H)-pyridone, hydroiodide 3-(4-benzylsulfinylphenyl)-5-(3-biphenylyl)-1-isopropenyl-4(1H)-pyridone 3-[3,5-di(methylsulfonyloxy)phenyl]-5-[3-(5-phenylpentylsulfinyl)phenyl]-1-vinyl-4(1H)-pyridone 3-[2-(3-cyanopropylsulfinyl)phenyl]-1-methoxycarbonylmethyl-5-phenyl-4(1H)-pyridinethione 3-(3-acetoxyphenyl)-5-[2-(7-cyanoheptylsulfinyl)phenyl]-1-methoxycarbonylmethyl-4(1H)-pyridone 1-(2-carboxyethyl)-3-[3-(3-cyclohexenyl)-5-(3-cyanoundecenylsulfinyl)phenyl]-4(1H)-pyridone 3-(2-chloro-4-cyclohexylphenyl)-5-[3-chloro-5-(2-ethoxyethylsulfinyl)phenyl]-1-(2-cyanoethyl)-4(1H)-pyridinethione 1-(2-chloroethyl)-3-[4-(6-methoxyhexylsulfinyl)phenyl]-4(1H)-pyridone 3-(4-cyclopropylphenyl)-1-iodomethyl-5-[3-(6-propoxynonylsulfinyl)phenyl]-4(1H)-pyridone 3-[3-(2-chloro-6-undecynylsulfinyl)phenyl]-1-(2,2-dibromoethyl)-5-(2-ethyl-5-vinylsulfinylphenyl)-4(1H)-pyridinethione 3-[3,5-di(allylsulfinyl)phenyl]-5-phenyl-1-propyl-4(1H)-pyridone, hydrofluoride 3-[3-(2,4-hexadienylsulfinyl)phenyl[-1-methyl-5-phenyl-4(1H)-pyridinethione 1-dimethylamino-3-[2-(5-dodecenylsulfinyl)phenyl]-5-(3-isobutylphenyl)-4(1H)-pyridone 1-acetoxy-3-[4-(2-bromoallylsulfinyl)phenyl]-5-(2,4-dimethylphenyl)-4(1H)-pyridinethione 1-ethoxy-3-(3-iodo-4-pentylphenyl)-5-[3-(3,3,4,4-tetrafluoro-1-butenylsulfinyl)-5-hexylphenyl]-4(1H)-pyridone 1-isopropoxy-3-phenyl-5-[4-(1,1,2-trichloro-3-heptenylsulfinyl)phenyl]-4(1H)-pyridinethione 3-[4-(9-bromo-4-nonenylsulfinyl)phenyl]-5-[2-(3-ethylhexyl)phenyl]-1-ethynyl-4(1H)-pyridinethione 3-[2,4-di(chlorodifluoromethyl)phenyl-1-propargyl-5-[3-(1,2,3-triiodo-6-dodecenylsulfinyl)phenyl]-4-(1H)-pyridone 3-[3-(4-bromo-2-butynylsulfinyl)-5-methylphenyl]-5-[2-iodo-3-(1,2,3-trichloropentyl)phenyl]-1-vinyl-4(1H)-pyridone 1-allyl-3-[2-(2,2-dibromo-4-hexynylsulfinyl)phenyl]-5-phenyl-4(1H)-pyridone 1-methoxycarbonylmethyl-3-[3-ethyl-5-(9,9,10,10-tetrafluoro-2-decynylsulfinyl)phenyl]-5-phenyl-4(1H)-pyridinethione 3-(4-benzyl-2-bromophenyl)-1-(2-carboxyethyl)-5-[3-(1-chlorobutyl)-5-(6-dodecynylsulfinyl)phenyl]-4-(1H)-pyridone 1-(2-cyanoethyl)-3-(4-phenylsulfinylphenyl)-5-phenyl-4(1H)-pyridinethione 1-cyanomethyl-3-[4-(3-fluorophenylsulfinyl)phenyl]-5-[3-(4-octenyl)phenyl]-4(1H)-pyridone 1-chloromethyl-3-[3-(1,1-dichloro-4-octenyl)-4-nitrophenyl]-5-[3-(2-iodophenylsulfinyl)phenyl]-4(1H)-pyridone 3-[3-(2-chlorovinyl)-5-(4-methylphenylsulfinyl)phenyl]-1-ethoxy-5-[3-(8-iodo-4-octenyl)phenyl]-4(1H)-pyridone 3-[4-(3-isopropylphenylsulfinyl)phenyl]-5-phenyl-1-propyl-4(1H)-pyridone 3-[3-(2-ethoxyphenylsulfinyl)phenyl]-1-methyl-5-[4-(2-propoxyphenoxy)phenyl]-4(1H)-pyridone 3-[4-(2,4-cyclohexadienyl)-3-fluorophenyl]-1-ethyl-5-[3-hydroxy-5-(3-nitrophenylsulfinyl)phenyl]-4(1H)-pyridinethione 1-methyl-3-(4-methylsulfonylphenyl)-5-phenyl-4(1H)-pyridinethione 1-ethyl-3-(3-hexylsulfonylphenyl)-5-(4-hydroxyphenyl)-4(1H)-pyridone 3-(2-carboxy-4-ethylphenyl)-1-dimethylamino-5-[4-(3-ethylheptylsulfonyl)phenyl]-4(1H)-pyridone 1-acetoxy-3-(2-hexyl-5-fluorophenyl)-5-(3-nitro-5-nonylsulfonylphenyl)-4(1H)-pyridone 3-phenyl-1-propoxy-5-[2-(3-propylnonylsulfonyl)phenyl]-4(1H)-pyridone 1-ethoxy-3-phenyl-5-(3-trifluoromethyl-5-trifluoromethylsulfonylphenyl)-4(1H)-pyridone 3-[4-(2-chloroethylsulfonyl)phenyl]-5-(3-fluoro-4-octylphenyl)-1-methoxy-4(1H)-pyridinethione 3-(3-bromo-5-nitrophenyl)-1-ethynyl-5-[4-cyano-2-(6,6-dibromohexylsulfonyl)phenyl]-4(1H)-pyridone 3-[3-(4,4-diiodododecylsulfonyl)phenyl]-5-(2-naphthyl)-1-(1-propynyl)-4(1H)-pyridone 3-(4-benzylsulfonylphenyl)-5-[3-(2-ethoxyphenyl)phenyl]-1-isopropenyl-4(1H)-pyridinethione 3-[5-chloromethyl-4-(2-propylphenyl)phenyl]-1-vinyl-5-[4-(3-phenylbutylsulfonyl)phenyl]-4(1H)-pyridone 3-[3-(3-cyanopropylsulfonyl)phenyl]-1-methoxycarbonylmethyl-5-phenyl-4(1H)-pyridone 1-(2-carboxyethyl)-3-[4-(7-cyanoheptylsulfonyl)phenyl]-5-[3-(4-chlorophenyl)phenyl]-4(1H)-pyridone 1-cyanomethyl-3-[3-(11-cyanoundecylsulfonyl)-5-fluorophenyl]-5-(4-propylsulfonyloxyphenyl)-4(1H)-pyridone 3-(2-acetoxy-4-ethoxyethylsulfonylphenyl)-1-chloromethyl-5-(5-cyclopropyl-2-trifluoromethylphenyl)-4(1H)-pyridone 3-(3-ethoxyhexylsulfonylphenyl)-5-phenyl-1-trifluoromethyl-4(1H)-pyridinethione 3-[4-(3-cyclohexenyl)phenyl]-1-propyl-5-[3-(9-propoxynonylsulfonyl)phenyl]-4(1H)-pyridone 3-[3-cyanomethyl-4-(1-cyclobutenyl)phenyl]-1-methyl-5-(4-vinylsulfonylphenyl)-4(1H)-pyridinethione 3-(2-allylsulfonyl-4-chlorophenyl)-5-(2-allyl-3-cyclohexylphenyl)-1-dimethylamino-4(1H)-pyridinethione 1-acetoxy-3-[4-(2,3-hexadienylsulfonyl)phenyl]-5-phenyl-4(1H)-pyridone 3,5-bis[3-(4-decenylsulfonyl)phenyl]-1-methoxy-4(1H)-pyridone 3-[4-(2-bromoallylsulfonyl)-2-methylphenyl]-1-methyl-5-[3-(7,7,8,8-tetrafluoro-2-octynyl)phenyl]-4(1H)-pyridone 3-[4-(6-heptynyl)-3-methylphenyl]-1-ethyl-5-[3-(1,1,2-triiodo-3-butenylsulfonyl)-5-chlorophenyl]-4(1H)-pyridone 3-[2-(5,5-dibromo-2-pentynyl)phenyl]-1-dimethylamino-5-[3-(5-fluoro-2-nonenylsulfonyl)phenyl]-4(1H)-pyridone 1-acetoxy-3-[2-ethyl-4-(5-methoxypentyl)phenyl]-5-[3-(12,12,12-trichloro-6-dodecenylsulfonyl)phenyl]-4(1H)-pyridone 3-[2-(3-chloro-5-hexynylsulfonyl)-4-nitrophenyl]-5-[3-bromo-5-(6-cyanohexyl)phenyl]-1-methoxy-4(1H)-pyridone 3-[4-(6,6-dibromo-3-hexynylsulfonyl)phenyl]-5-phenyl-1-propoxy-4(1H)-pyridone 3-[3-(2-cyanoethyl)phenyl]-1-ethynyl-5-[1,1,2,2-tetrafluoro-6-decynylsulfonyl)phenyl]-4(1H)-pyridone 3-(3-benzyl-5-ethynylsulfonylphenyl)-5-[2-(7-phenylheptyl)phenyl]-1-vinyl-4(1H)-pyridinethione 1-cyanomethyl-3-[3-(6-dodecynylsulfonyl)-5-methylphenyl]-5-[2-methyl-4-(1,1,2,2-tetrafluoroethyl)phenyl]-4(1H)-pyridone 1-(2-carboxyethyl)-3-phenyl-5-(3-phenylsulfonylphenyl)-4(1H)-pyridone 3-[3-(4,4-diiodobutyl)phenyl]-5-[4-(4-fluorophenylsulfonyl)phenyl]-1-trifluoromethyl-4(1H)-pyridone 3-[2-chloromethyl-3-(6,6-dibromohexyl)phenyl]-5-[3-(3-iodophenylsulfonyl)phenyl]-1-methyl-4(1H)-pyridone 1-ethyl-3-[3-ethyl-5-(4-methylphenylsulfonyl)phenyl]-5-[4-iodo-3-(2-propylbutyl)phenyl]-4(1H)-pyridinethione 1-(1-cyanoethyl)-3-[3-(2-propylphenylsulfonyl)phenyl]-5-phenyl-4(1H)-pyridinethione 3-[5-butyl-2-(3-methoxyphenylsulfonyl)phenyl]-1-(1-carboxyethyl)-5-phenyl-4(1H)-pyridinethione 3-(3-isopropyl-4-trifluoromethylphenyl)-1-methyl-5-[3-(2-propoxyphenylsulfonyl)phenyl]-4(1H)-pyridone 3-[2-chloro-4-(4-nitrophenylsulfonyl)phenyl]-1-ethyl-5-[3-fluoro-5-(4-heptyl)phenyl]-4(1H)-pyridone 3-(3-cyclopropylmethylphenyl)-1-methyl-5-(2-trifluoromethylphenyl)-4(1H)-pyridone 3,5-bis[3-(2-cyclopentylethyl)phenyl]-1-methoxy-4(1H)-pyridone 3-(2-cyclopropoxyphenyl)-1-ethyl-5-(2-fluorophenyl)-4(1H)-pyridinethione 3-(4-cyclohexyloxyphenyl)-1-methyl-5-phenyl-4-(1H)-pyridone, methanesulfonate 3-(4-chlorophenyl)-5-(3-cyclobutylthiophenyl)-1-ethoxy-4(1H)-pyridone 3-(2-cyclopentylsulfinylphenyl)-5-(3-hexylphenyl)-1-propoxy-4(1H)-pyridone, hydrochloride 3-(4-cyclopropylsulfonylphenyl)-5-(2,4-diethylphenyl)-1-propyl-4(1H)-pyridinethione 3-(3-cyclohexylsulfonylphenyl)-5-(3,5-difluorophenyl)-1-trifluoromethyl-4(1H)-pyridone 1-cyanomethyl-3-(2-cyclopropylmethoxyphenyl)-5-(3-trifluoromethylphenyl)-4(1H)-pyridone 1-acetoxy-3-[3-(2-cyclohexylethoxy)phenyl]-5-phenyl-4(1H)-pyridone, hydrobromide 3-[4-(2-cyclobutylethylthio)phenyl]-1-dimethylamino-5-(3,5-dimethylphenyl)-4(1H)-pyridone 3-(3-cyclopentylmethylsulfinylphenyl)-1-methyl-5-(3-trifluoromethylphenyl)-4(1H)-pyridone 3-[4-(2-cyclohexylethylsulfonyl)phenyl]-1-ethyl-5-(3-propylphenyl)-4(1H)-pyridone 3-cyclopropylmethyl-5-(3-fluorophenyl)-1-methoxy-4(1H)-pyridone, methanesulfonate 3-(4-chlorophenyl)-3-(2-cyclohexylethyl)-1-ethoxy-4(1H)-pyridone 3-(3-fluorophenyl)-1-methyl-5-phenylthio-4(1H)-pyridone 3-(3-chloro-5-methylphenyl)-1-ethoxy-5-phenylsulfinyl-4(1H)-pyridone 1-acetoxy-3-phenylsulfonyl-5-(4-trifluoromethylphenyl)-4(1H)-pyridinethione 3-(2-butylphenyl)-5-(3,5-dichlorophenylthio)-1-(1-propenyl)-4(1H)-pyridone 3-(2,4-dibromophenyl)-1-dimethylamino-5-(4-ethylphenylsulfinyl)-4(1H)-pyridone 1-cyanomethyl-3-phenyl-5-(3-propoxyphenylsulfinyl)-4(1H)-pyridinethione 3-methylthio-5-phenyl-1-(1-propynyl)-4(1H)-pyridone 3-(2-chlorophenyl)-1-methyl-5-propylsulfinyl-4(1H)-pyridinethione, hydrofluoride 3-ethylsulfonyl-1-isopropyl-5-(3-trifluoromethylphenyl)-4(1H)-pyridone 1-ethoxy-3-(4-fluorophenyl)-5-trifluoromethyl-thio-4(1H)-pyridinethione, toluenesulfonate 3-(2-chloroethylsulfinyl)-1-chloromethyl-5-(3-methylphenyl)-4(1H)-pyridone 3-(2-bromopropylsulfonyl)-1-chlorodifluoromethyl-5-phenyl-4(1H)-pyridinethione 1-(1-carboxyethyl)-3-(2,4-dimethylphenyl)-5-vinylthio-4(1H)-pyridone 3-allylsulfinyl-3-(3,5-diiodophenyl)-1-methyl-4(1H)-pyridinethione 1-methyl-3-(2-trifluoromethylphenyl)-5-vinylsulfonyl-4(1H)-pyridinethione 3-(3-allylphenyl)-5-(2-chlorovinylthio)-1-ethoxy-4(1H)-pyridinethione 1-(2-bromoethyl)-3-(2-chloro-3-fluorophenyl)-5-(1,2-difluoroallylsulfinyl)-4(1H)-pyridone 3-(2-bromo-1-propenylsulfonyl)-1-methyl-5-(3-methylphenyl)-4(1H)-pyridinethione 1-dimethylamino-3-(4-methoxy-2-butenyl)-5-phenyl-4(1H)-pyridone 1-ethynyl-3-(2-propoxyvinyl)-5-(3-trifluoromethylphenyl)-4(1H)-pyridone 3-(6-ethoxy-2-hexenyl)-1-methyl-5-phenyl-4(1H)-pyridinethione, hydrochloride The following are the preferred compounds of the invention.

1-methyl-3-phenyl-5-(3-trifluoromethylphenyl)-4(1H)-pyridone 3-(3-fluorophenyl)-1-methyl-5-phenyl-4(1H)-pyridone 3-(3-chlorophenyl)-1-methyl-5-phenyl-4(1H)-pyridone 3,5-bis(3-chlorophenyl)-1-methyl-4(1H)-pyridone 3-(3-chlorophenyl)-5-(3-fluorophenyl)-1-methyl-4(1H)-pyridone
1-methyl-3-(3-methylphenyl)-5-phenyl-4(1H)-pyridone
3,5-diphenyl-1-methyl-4(1H)-pyridone
1-methyl-3,5-bis(3-trifluoromethylphenyl)-4(1H)-pyridone
3-(3-bromophenyl)-1-methyl-5-phenyl-4(1H)-pyridone
3-(3-methoxyphenyl)-1-methyl-5-phenyl-4(1H)-pyridone
3-(3-ethoxyphenyl)-1-methyl-5-phenyl-4(1H)-pyridone
1-methyl-3-phenyl-5-(3-propoxyphenyl)-4(1H)-pyridone
3-(3-isopropoxyphenyl)-1-methyl-5-phenyl-4(1H)-pyridone
1-methyl-3-phenyl-5-[3-(1,1,2,2-tetrafluoroethoxy)phenyl]-4(1H)-pyridone
3,5-bis(3-fluorophenyl)-1-methyl-4(1H)-pyridone
3-(2-chlorophenyl)-1-methyl-5-(3-trifluoromethylphenyl)-4(1H)-pyridone
3-(3-chlorophenyl)-1-methyl-5-(3-trifluoromethylphenyl)-4(1H)-pyridone
3-(4-chlorophenyl)-1-methyl-5-(3-trifluoromethylphenyl)-4(1H)-pyridone
3-(2-fluorophenyl)-1-methyl-5-(3-trifluoromethylphenyl)-4(1H)-pyridone
3-(3-fluorophenyl)-1-methyl-5-(3-trifluoromethylphenyl)-4(1H)-pyridone
3-(4-fluorophenyl)-1-methyl-5-(3-trifluoromethylphenyl)-4(1H)-pyridone
3-(3-chlorophenyl)-5-(4-chlorophenyl)-1-methyl-4(1H)-pyridone
1-ethyl-3-phenyl-5-(3-trifluoromethylphenyl)-4(1H)-pyridone
1-methyl-3-(3-trifluoromethylphenyl)-4(1H)-pyridone
3-chloro-1-methyl-5-(3-trifluoromethylphenyl)-4(1H)-pyridone
3-bromo-1-methyl-5-(3-trifluoromethylphenyl)-4(1H)-pyridone
1,3-dimethyl-5-(3-trifluoromethylphenyl)-4(1H)-pyridone
3-ethyl-1-methyl-5-(3-trifluoromethylphenyl)-4(1H)-pyridone
1-methyl-3-(3-methylthiophenyl)-5-phenyl-4(1H)-pyridone
3-(4-chloro-3-trifluoromethylphenyl)-1-methyl-5-phenyl-4(1H)-pyridone
3-(2-chlorophenyl)-5-(3-chlorophenyl)-1-methyl-4(1H)-pyridone
3-(3-bromophenyl)-5-(3-chlorophenyl)-1-methyl-4(1H)-pyridone
3-(3-bromophenyl)-1-methyl-5-(2-methylphenyl)-4(1H)-pyridone
3-(3-chlorophenyl)-1-methyl-5-(2-methylphenyl)-4(1H)-pyridone
1-methyl-3,5-bis(3-methylphenyl)-4(1H)-pyridone
3-(2-bromophenyl)-1-methyl-5-(3-trifluoromethylphenyl)-4(1H)-pyridone
1-methyl-3-(2-methylphenyl)-5-(3-trifluoromethylphenyl)-4(1H)-pyridone
3-(2-ethylphenyl)-1-methyl-5-(3-trifluoromethylphenyl)-4(1H)-pyridone
1-methyl-3-(2-trifluoromethylphenyl)-5-(3-trifluoromethylphenyl)-4(1H)-pyridone
3-(2-methoxyphenyl)-1-methyl-5-(3-trifluoromethylphenyl)-4(1H)-pyridone
3-(3-bromophenyl)-1-methyl-5-(3-trifluoromethylphenyl)-4(1H)-pyridone
1-methyl-3-(3-methylphenyl)-5-(3-trifluoromethylphenyl)-4(1H)-pyridone
1-methyl-3-(4-methylphenyl)-5-(3-trifluoromethylphenyl)-4(1H)-pyridone
3-(3-isobutylphenyl)-1-methyl-5-phenyl-4(1H)-pyridone
1-methyl-3-propyl-5-(3-trifluoromethylphenyl)-4(1H)-pyridone
3-methoxy-1-methyl-5-(3-trifluoromethylphenyl)-4(1H)-pyridone
3-ethoxy-1-methyl-5-(3-trifluoromethylphenyl)-4(1H)-pyridone
3-isopropoxy-1-methyl-5-(3-trifluoromethylphenyl)-4(1H)-pyridone
1-methyl-3-phenoxy-5-(3-trifluoromethylphenyl)-4(1H)-pyridone
3-(4-chloro-3-trifluoromethylphenyl)-5-ethoxy-1-methyl-4(1H)-pyridone
1-methyl-3-(4-chloro-3-trifluoromethylphenyl)-5-propyl-4(1H)-pyridone
3-ethyl-1-methyl-5-(4-chloro-3-trifluoromethylphenyl)-4(1H)-pyridone
3-ethylthio-1-methyl-5-(3-trifluoromethylphenyl)-4(1H)-pyridone
1-methyl-3-propylthio-5-(3-trifluoromethylphenyl)-4(1H)-pyridone
1-methyl-3-allylthio-5-(3-trifluoromethylphenyl)-4(1H)-pyridone
1-methyl-3-isopropylthio-5-(3-trifluoromethylphenyl)-4(1H)-pyridone
3-ethylsulfinyl-1-methyl-5-(3-trifluoromethylphenyl)-4(1H)-pyridone
1-methyl-3-(3-trifluoromethylphenyl)-5-trifluoromethylthio-4(1H)-pyridone
1-methyl-3-(2-chloro-4-fluorophenyl)-5-(3-trifluoromethylphenyl)-4(1H)-pyridone
3-(2,5-dimethylphenyl)-1-methyl-5-(3-trifluoromethylphenyl)-4(1H)-pyridone
3-(3,4-dimethylphenyl)-1-methyl-5-(3-trifluoromethylphenyl)-4(1H)-pyridone
1-methyl-3-(3-methylthiophenyl)-5-(3-trifluoromethylphenyl)-4(1H)-pyridone
1,3-diethyl-5-(3-trifluoromethylphenyl)-4(1H)-pyridone
1-ethyl-3,5-bis(3-trifluoromethylphenyl)-4(1H)-pyridone
3-isopropyl-1-methyl-5-(3-trifluoromethylphenyl)-4(1H)-pyridone
1-methyl-3-phenyl-5-(3-trifluoromethylphenyl)-4(1H)-pyridinethione The compounds of this invention can be prepared by various synthetic routes. Benary and Bitter, Ber. 61, 1058 (1928) taught the synthesis of an intermediate disodium salt of 1,5-dihydroxy-2,4-diphenyl-1,4-pentadien-3-one by the condensation of 1,3-diphenyl-2-propanone with ethyl formate in the presence of sodium methoxide. The intermediate pentadienone is neutralized by strong acid and forms 3,5-diphenyl-4-pyrone. Reaction of the pyrone with ammonium acetate at an elevated temperature produces 3,5-diphenyl-4(1H)-pyridone.

Alternatively, 3,5-diphenyl-4(1H)-pyridones can be prepared by the reaction of an appropriately ring-substituted 1,3-diphenyl-2-propanone with formamide and formamidine acetate. Reaction at reflux temperature produces the corresponding 3,5-diphenyl-4(1H)-pyridone, which is reacted with a halide of the desired 1-substituent in the presence of a suitable strong base to form the desired compound.

A preferred synthesis of the compounds is adapted from the methods of Benary and Bitter and of El-Kholy et al., cited above. An appropriately substituted 1-phenyl-2-propanone is formylated at low temperature with sodium methoxide and ethyl formate in ether, and the product is treated with an amine salt of the desired R substituent in aqueous medium. The resulting intermediate is predominantly a 1-(R-amino)-2-phenyl-1-buten-3-one. Some pyridone is also formed at this step, as reported by El-Kholy et al. The butenone is reformylated as before, and spontaneously cyclizes to form the 1-substituted-3-phenyl-4(1H)-pyridone.

Another preferred synthesis is similar to the above, but uses an aminoformylation step instead of formylation. A preferred aminoformylation agent is a formiminium halide, such as the reaction product of phosgene and dimethylformamide. The propanone is diaminoformylated, and the intermediate is exchanged with an amine or an amine salt of the R substituent and hydrolyzed with acid or alkali to form the 1-substituted-3-phenyl-4(1H)-pyridone.

The starting 2-propanones may be prepared by syntheses in the literature. For example, see Coan et al., *J. Am. Chem. Soc.* 76, 501 (1954); Sullivan et al., "Disodium Tetracarbonylferrate", *American Laboratory* 49–56 (June 1974); Collman et al., "Synthesis of Hemifluorinated Ketones using Disodium Tetracarbonylferrate," *J. Am. Chem. Soc.* 95, 2689–91 (1973); Collman et al., "Acyl and Alkyl Tetracarbonylferrate Complexes as Intermediates in the Synthesis of Aldehydes and Ketones", *J. Am. Chem. Soc.* 94, 2516–18 (1972).

The general synthesis methods of the compounds proceed from either ketone starting compounds or form carbonyl halides. The general process is the same, whichever starting compound is used. The general process, of which the preferred synthesis described above is an embodiment, will be discussed first. Reagents and reaction conditions will then be explained in detail, and some preparative examples will be illustrated. The synthesis proceeds through an intermediate of the formula

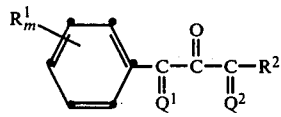

wherein
 $Q^1$ and $Q^2$ independently represent 2 hydrogen atoms, =CHOH, or an alkali metal salt thereof, =CHN($R^9$)$_2$ or =CHNHR, provided that only one of $Q^1$ and $Q^2$ represents =CHNHR.

The $R^9$ groups independently represent $C_1$–$C_3$ alkyl, or the $R^9$ groups combine with the nitrogen atom to which they are attached to form pyrrolidino, piperidino, morpholino, N-methylpiperazino and the like.

The =CHOH groups, which may be in the form of alkali metal salts, are provided by reaction with formylating agents which will be defined below. The =CHN($R^9$)$_2$ groups are provided by reaction with aminoformylating agents, and the =CHNHR groups are provided by exchanging either =CHOH groups or =CHN($R^9$)$_2$ groups with amines of the formula RNH$_2$.

The intermediates described above are prepared from either ketones or carbonyl halides, as will be explained below. When $Q^1$ and $Q^2$ each represent 2 hydrogen atoms, the pyridones are prepared by either
1. reacting with a formylating or aminoformylating agent;
2. reacting again with a formylating or aminoformylating agent; and
3. reacting with an amine of the formula RNH$_2$; or
1. reacting with a formylating or aminoformylating agent;
2. reacting with an amine of the formula RNH$_2$; and
3. reacting again with a formylating or aminoformylating agent.

When one of $Q^1$ and $Q^2$ represents either =CHOH or =CHN($R^9$)$_2$, and the other represents 2 hydrogen atoms, the pyridones are prepared by either
1. reacting with a formylating or aminoformylating agent; and
2. reacting with an amine of the formula RNH$_2$; or
1. reacting with an amine of the formula RNH$_2$; and
2. reacting with a formylating or aminoformylating agent.

When each of $Q^1$ and $Q^2$ represent either =CHOH or =CHN($R^9$)$_2$, the pyridones are prepared by reacting with an amine of the formula RNH$_2$.

The variations of the synthesis, and the preparation of the intermediates, will be sketched below.

When the process starts with a ketone of the general formula

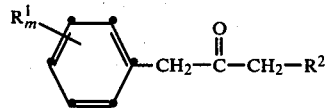

the first step is the formylation or aminoformylation of one of the methylene groups. If a formylating agent is used, a ketone of the formula

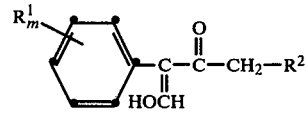

is produced. Reaction with an aminoformylating agent produces an enaminoketone such as (III) below.

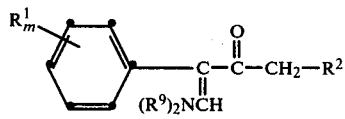

Organic chemists will understand that, although the sketches above show the first formylation or aminoformylation as occurring on a certain side of the ketone, it may in fact occur on either side of the ketone, depending on the activating characteristics of $R^1$ and $R^2$. The course of the reaction is the same in either case. It will also be understood that, in many instances, the product of the formylation or aminoformylation step will actually be a mixture containing the two possible monosubstituted compounds and the disubstituted compound.

The monosubstituted product is formylated or aminoformylated again, and exchanged with an amine of the formula RNH$_2$. The steps may be performed in either order. If the exchange is performed first, the intermediate product is an enaminoketone of the formula

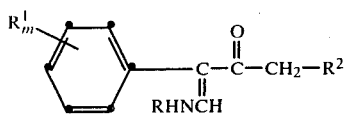
IV.

Either formylation or aminoformylation of the above enaminoketone affords the pyridone product, as the intermediate cyclizes as soon as the second group is introduced on the other methylene group.

Alternatively, either of compounds (II) or (III) may be either formylated or aminoformylated to provide intermediates of any of the formulae below.

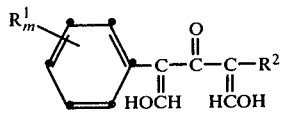
V.

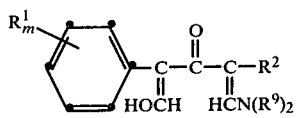
VI.

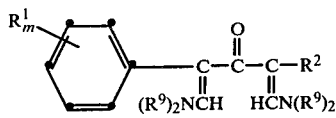
VII.

It will be understood that the compound similar to (VI), wherein the formyl and aminoformyl groups are reversed, is equivalent in all respects to compound (VI). Pyridones are formed from any of the above three intermediates by simple contact of the intermediate with an amine of the formula $RNH_2$.

When the starting compound is a carbonyl halide, the process proceeds essentially as described above, except for a first step performed as follows:

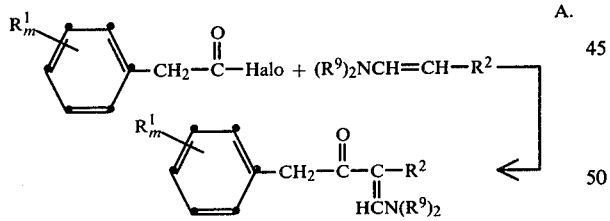
A.

It will be understood that reaction (A) can also be performed in the opposite manner, as shown below:

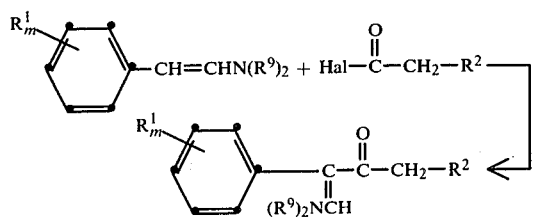
B.

It is also possible to form intermediates using phosgene as the carbonyl halide when the 3- and 5-substituents of the pyridone product are identical.

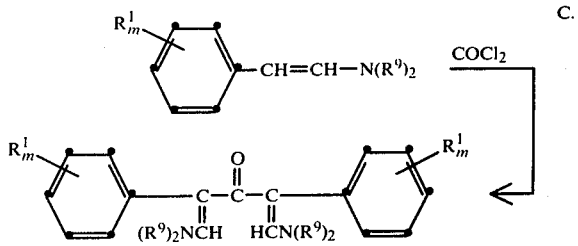
C.

The enaminoketones formed in equations (A), (B) and (C) above are identical to the intermediates described in (III) and (VII) above, and are converted to the pyridone products as described above.

Alternatively, it is possible to prepare the 1-unsubstituted pyridones by using $NH_3$ in place of $RNH_2$ in the process, or by using the process of Benary and Bitter. The pyridone is then alkylated at the 1-position with a halide of R, or with a dialkyl sulfate, according to common procedures.

An alternative method of alkylation proceeds by converting the 1-unsubstituted pyridone to the 4-halo or 4-alkoxy derivative by reaction with a halogenating agent, or an O-alkylating agent. Suitable halogenating agents include such agents as $POCl_3$, $POBr_3$, $PCl_5$ and the like. O-alkylating agents include such reagents as methyl trifluoromethanesulfonate, methyl fluorosulfonate and the like, as well as alkyl halides used in the presence of base. In the next step, the 4-halo or 4-alkoxy compound is reacted with a halide of R to form the 1-R-substituted, 4-substituted pyridinium salt. The salt is then hydrolyzed with either a mineral acid or an alkali metal hydroxide to produce the desired product. See, for example, Takahashi et al., Pharm. Bull. (Japan) 1, 70–74 (1953).

As a chemist would expect, the amines, $RNH_2$, may be used in the form of salts, preferably hydrohalide salts, including hydrochlorides, hydrobromides and the like. Such salts are often more convenient than the free amines.

The formylating agents used in the process are chosen from the common agents used for such reactions. The preferred formylating agents are esters of formic acid of the formulae

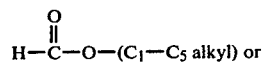

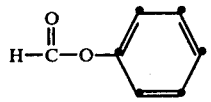

Similar formylations are discussed in Organic Syntheses 300–02 (Collective Vol. III 1955).

The esters are used in the presence of strong bases, of which alkali metal alkoxides are preferred, such as sodium methoxide, potassium ethoxide and lithium propoxide. Other bases may also be used, including alkali metal hydrides, alkali metal amides, and inorganic bases including alkali metal carbonates and hydroxides. Such strong organic bases as diazabicyclononane and diazabicycloundecane are also useful.

Reactions with formylating agents are performed in aprotic solvents such as are regularly used in chemical synthesis. Ethyl ether is usually the preferred solvent.

Ethers in general, including solvents such as ethyl propyl ether, ethyl butyl ether, 1,2-dimethoxyethane and tetrahydrofuran, aromatic solvents such as benzene and xylene, and alkanes such as hexane and octane can be used as formylation solvents.

Because of the strong bases used in the formylation reactions, low temperatures produce the best yields. Reaction at temperatures in the range of from about −25° C. to about 10° C. is preferred. The reaction mixture may be allowed to warm to room temperature, however, after the reaction has proceeded part way to completion. Reaction times from about 1 to about 24 hours are adequate for economic yields in the formylation reactions.

The aminoformylating agents used in these syntheses may be any compounds capable of reacting with an active methylene group to introduce a $=CHN(R^9)_2$ group, or its acid addition salt. Such agents are chosen from among s-triazine, the orthoformamides,

the formate ester aminals,

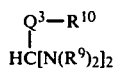

the formamide acetals,

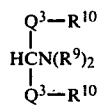

the tris(formylamino)methanes,

and preferably from the formiminium halides,

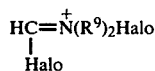

$Q^3$ in the structures above represents oxygen or sulfur, and $R^{10}$ represents $C_1$-$C_6$ alkyl or phenyl.

Useful references on the aminoformylating agents include DeWolfe, Carboxylic Acid Derivatives 420–506 (Academic Press 1970), and Ulrich, Chemistry of Imidoyl Halides 87–96 (Plenum Press 1968). Bredereck et al. have written many papers on such agents and reactions, of which the following are typical. Ber. 101, 4048–56 (1968); Ber. 104, 2709–26 (1971); Ber. 106, 3732–42 (1973); Ber. 97, 3397–406 (1964); Ann. 762, 62–72 (1972); Ber. 97, 3407–17 (1964); Ber. 103, 210–21 (1970); Angew. Chem. 78, 147 (1966); Ber. 98, 2887–96 (1965); Ber. 96, 1505–14 (1963); Ber. 104, 3475–85 (1971); Ber. 101, 41–50 (1968); Ber. 106, 3725–31 (1973); and Angew. Chem. Int'l. Ed. 5, 132 (1966). Other notable papers on the subject include Kreutzberger et al., Arch. der Pharm. 301, 881–96 (1968), and 302, 362–75 (1969), and Weingarten et al., J. Org. Chem. 32, 3293–94 (1967).

Aminoformylations are usually carried out without solvent, at elevated temperatures from about 50° C. to about 200° C. Solvents such as dimethylformamide are sometimes used, however, particularly when it is desirable to raise the boiling point of the reaction mixture.

When aminoformylating with formiminium halides, however, aprotic solvents, such as described above in the description of solvents for formylation, are used at temperatures from about 0° C. to about 80° C., preferably above room temperature. Halogenated solvents such as chloroform and methylene chloride can also be used in such aminoformylations if desired.

The exchange reactions with $RNH_2$ are best performed in protic solvents of which alkanols are preferred and ethanol is most appropriate. Temperatures from about −20° C. to about 100° C. can be used for the exchange reactions. Room temperature is satisfactory and is preferred.

In general, intermediate compounds in the synthesis are not purified, but are simply used in successive steps after separation by extraction, neutralization or removal of excess solvent or reactant as appropriate.

The enamine acylation reactions, A-C, are performed in the presence of bases such as tertiary amines, alkali metal carbonates, magnesium oxide and the like, and in aprotic solvents as described above.

In some instances, as organic chemists will understand, it is necessary to apply additional synthetic steps after the pyridone compound has been formed. For example, it is convenient to form compounds having alkoxy, alkanoyloxy and like $R^1$ and $R^5$ substituents by first making the corresponding hydroxy-substituted compound, and then substituting on the oxygen atom.

The pyridinethiones of this invention are readily prepared by the treatment of the corresponding pyridones with $P_2S_5$ in pyridine at reflux temperature, according to known methods.

The 1-acetoxy compounds are made by first making the corresponding 1-hydroxypyridone, using $NH_2OH$ as the amine, and esterifying it with acetic anhydride. The other 1-substituents are provided by appropriate R substituents on the amines, $RNH_2$, used to prepare the pyridones.

The following preparative examples are presented to assure that those skilled in organic chemistry can obtain any desired compound of this invention.

The examples below show the various processes by which compounds of the invention have been made. It will be understood, however, that all of the various processes can be used, with appropriate variations, to make any compound of the invention.

Many exemplary compounds are indicated as made by the general process of a previous exemplary compound. In such instances, an ordinarily skilled organic chemist will readily see the minor changes to the exemplary process which will be needed to prepare the other exemplary compounds.

The first example below illustrates the preparation of a compound by a preferred synthetic process.

EXAMPLE 1

1-methyl-3-phenyl-5-(3-trifluoromethylphenyl)-4(1H)-pyridone

A 30 ml. portion of phosgene was combined with 135 ml. of chloroform and cooled to −10° C. The temperature was held approximately constant while 23 ml. of dimethylformamide was added dropwise. After the addition, a solution of 32 g. of 1-phenyl-3-(3-trifluoromethylphenyl)-2-propanone in 40 ml. of chloroform was added, and the reaction mixture was stirred under reflux at 62° C. for 90 minutes. The reaction mixture was then cooled, and to it was added 40 ml. of water, 17 ml. of 25 percent aqueous sodium hydroxide, and 26 ml. of 40 percent aqueous methylamine. The mixture was stirred and heated to 100° C. to distill off the solvent.

The reaction mixture was then cooled, and to it was added 135 ml. of denatured ethanol, 26 ml. of 40 percent aqueous methylamine, and 24 g. of sodium hydroxide. The mixture was then stirred under reflux at 78° C. for 3 hours, and was then cooled. One hundred ml. of additional water was added, and the reaction mixture was heated at 100° C. to distill off the ethanol.

The mixture was then cooled again, and to it was added 200 ml. of dichloromethane. The layers were separated, and the organic layer was washed with 25 ml. of 5 percent aqueous hydrochloric acid. The layers were separated again, and the organic layer was evaporated to an oily residue under vacuum at 55° C. The residue was cooled, and triturated with 100 ml. of water and 200 ml. of diethyl ether. The product precipitated, and was recovered by filtration. The crude product was washed on the filter with 100 ml. of water and 200 ml. of diethyl ether and vacuum dried at 50° C. to produce 30.3 g. of 1-methyl-3-phenyl-5-(3-trifluoromethylphenyl)-4(1H)-pyridone, m.p. 149°–151° C. The yield was 92.1 percent of the theoretical yield.

The following example illustrates another preferred method of synthesis.

EXAMPLE 2

3,5-diphenyl-1-methyl-4(1H)-pyridone

A 10.5 g. portion of 1,3-diphenyl-2-propanone was dissolved in 11.1 g. of ethyl formate and added to 8.1 g. of sodium methoxide in 150 ml. of ethyl ether at 0°–5° C. over a 30-minute period. The reaction mixture was allowed to warm to room temperature and was stirred overnight. Then, a solution of 10.1 g. of methylamine hydrochloride in 50 ml. of water was added. The two-phase mixture was stirred at 30° C. for 10 minutes. The mixture was then extracted with methylene chloride, and the extracts were combined and concentrated under vacuum, leaving an oily residue which consisted principally of 2,4-diphenyl-1-methylamino-1-buten-3-one.

The residue was added to a stirred suspension of 8.1 g. of sodium methoxide in 150 ml. of ethyl ether. An 11.1 g. portion of ethyl formate was added and the mixture was stirred for 2 hours at 0°–5° C., during which a heavy white precipitate formed. The mixture was then filtered and the solids were washed on the filter with water and with ethyl ether. After drying, the solid product was found to weigh 8 g. A 50 ml. portion of water was added to the filtrate, the layers were separated, and the ether layer was concentrated under vacuum to yield 0.5 g. additional product. The products were combined and recrystallized from chloroform-hexane, and the purified product was identified as 3,5-diphenyl-1-methyl-4(1H)-pyridone, m.p. 187°–188° C., by infrared, nuclear magnetic resonance, and thin-layer chromatography analyses. The elemental analysis was as follows.

|   | Theoretical | Found |
|---|---|---|
| C | 82.73% | 82.54% |
| H | 5.79 | 5.98 |
| N | 5.36 | 5.15 |

The process of Example 2 was also used to produce the compounds below.

EXAMPLE 3

1-methyl-3,5-bis(3-trifluoromethylphenyl)-4(1H)-pyridone, m.p. 152°–154° C., yield 39%

EXAMPLE 4

3-phenyl-1-(2,2,2-trifluoroethyl)-5-(3-trifluoromethylphenyl)-4(1H)-pyridone, NMR, quartet centered at 256 CPS; aromatic protons at 420°–468 CPS; yield 46%

EXAMPLE 5

3-(3-bromophenyl)-5-(3-chlorophenyl)-1-methyl-4(1H)-pyridone, m.p. 192° C., yield 23%

EXAMPLE 6

3-(3-chlorophenyl)-5-(4-chlorophenyl)-1-methyl-4(1H)-pyridone, m.p. 170°–172° C., yield 26%

EXAMPLE 7

3-(2-fluorophenyl)-1-methyl-5-(3-trifluoromethylphenyl)-4(1H)-pyridone, m.p. 152°–154° C., yield 20%

EXAMPLE 8

3-(2-chlorophenyl)-5-(3-chlorophenyl)-1-methyl-4(1H)-pyridone, m.p. 160°–161° C., yield 15%

EXAMPLE 9

3-(3-methoxyphenyl)-1-methyl-5-(3-trifluoromethylphenyl)-4(1H)-pyridone, m.p. 113°–115° C., yield 7%

EXAMPLE 10

3-(4-chlorophenyl)-1-methyl-5-(3-trifluoromethylphenyl)-4(1H)-pyridone, m.p. 153°–155° C., yield 26%

EXAMPLE 11

1-allyl-3-phenyl-5-(3-trifluoromethylphenyl)-4(1H)-pyridone, m.p. 107°–109° C., yield 38%

EXAMPLE 12

3-(4-isopropylphenyl)-1-methyl-5-phenyl-4(1H)-pyridone, m.p. 159° C., yield 60%

EXAMPLE 13

3-(2-chlorophenyl)-1-methyl-5-(3-trifluoromethylphenyl)-4(1H)-pyridone, m.p. 191°–193° C., yield 14%

EXAMPLE 14

3-(3-fluorophenyl)-1-methyl-5-(3-trifluoromethylphenyl)-4(1H)-pyridone, m.p. 94°–96° C., yield 13%

EXAMPLE 15

3-(4-fluorophenyl)-1-methyl-5-(3-trifluoromethylphenyl)-4(1H)-pyridone, m.p. 133°–134° C., yield 29%

EXAMPLE 16

3-(4-methoxyphenyl)-1-methyl-5-(3-trifluoromethylphenyl)-4(1H)-pyridone, m.p. 162°–165° C., yield 33%

EXAMPLE 17

1-ethyl-3,5-bis(3-trifluoromethylphenyl)-4(1H)-pyridone, m.p. 185° C., yield 30%

The following example demonstrates the preparation of a pyridone by the formamidine acetate process, followed by alkylation at the 1-position.

EXAMPLE 18

3-(2,4-dichlorophenyl)-1-methyl-5-phenyl-4(1H)-pyridone

Ten g. of 1-(2,4-dichlorophenyl)-3-phenyl-2-propanone was heated at reflux with 10 g. of formamidine acetate in 75 ml. of formamide for 3 hours. The mixture was then poured onto ice and water was added. After the ice had melted, the mixture was filtered and the separated solids were washed with ethyl ether. The solids were then dissolved in ethanol, decolorized with charcoal and recrystallized to produce 1.3 g. of 3-(2,4-dichlorophenyl)-5-phenyl-4(1H)-pyridone, which was identified by infrared and nuclear magnetic resonance analyses.

The above pyridone was added to a solution of 0.5 g. of 50 percent sodium hydride in 60 ml. of DMSO and warmed until the pyridone dissolved. Excess methyl iodide was then added and the mixture was stirred for one-half hour. The mixture was then poured into water and filtered. The solids were extracted with methylene chloride, which was then dried with magnesium sulfate and evaporated to dryness. The residue was recrystallized from benzene-hexane to give 1.1 g. of 3-(2,4-dichlorophenyl)-1-methyl-5-phenyl-4(1H)-pyridone, m.p. 202°-204° C., which was identified by nuclear magnetic resonance and infrared analyses. The results of elemental microanalysis were as follows.

|   | Theory | Found |
|---|--------|-------|
| C | 66.68% | 66.84% |
| H | 3.83   | 4.05  |
| N | 4.09   | 4.01  |

The following exemplary compounds were made by the general process of Example 18. In some instances, the 1-unsubstituted pyridone intermediate was made by the prior art procedure of Benary and Bitter, cited above.

EXAMPLE 19

3,5-diphenyl-1-ethyl-4(1H)-pyridone, m.p. 171° C., yield 75%

EXAMPLE 20

1-allyl-3,5-diphenyl-4(1H)-pyridone, m.p. 174° C., yield 79%

EXAMPLE 21

3,5-diphenyl-1-isopropyl-4(1H)-pyridone, m.p. 152° C., yield 15%

EXAMPLE 22

1-cyanomethyl-3,5-diphenyl-4(1H)-pyridone, m.p. 221°-224° C., yield 55%

The next example illustrates the variation of the formylation process wherein the starting ketone is diformylated, and the pyridone is formed by exchange with an amine.

EXAMPLE 23

3,5-diphenyl-1-propyl-4(1H)-pyridone

A 100 g. portion of 1,3-diphenyl-2-propanone was dissolved in 35 g. of ethyl formate and added to 25 g. of sodium methoxide in 500 ml. of ethyl ether at 0°-5° C. over a 30-minute period. The reaction mixture was then allowed to warm to room temperature and was stirred overnight. The mixture was then filtered to yield 460 g. of crude disodium salt of 1,5-dihydroxy-2,4-diphenyl-1,4-pentadien-3-one, which was used in the next step without purification.

A 20 g. portion of the crude salt above was added to a solution of 20 g. of propylamine and 5 ml. of concentrated hydrochloric acid in 75 ml. of water. The mixture was stirred for one-half hour at room temperature. The reaction mixture was then extracted with ethyl ether, and the aqueous layer was evaporated to dryness. The residue was extracted with chloroform, the combined organic extracts were evaporated to dryness, and the residue was recrystallized from benzene-hexane to produce 3.05 g. of 3,5-diphenyl-1-propyl-4(1H)-pyridone, m.p. 172°-174° C.

The following typical compounds were also made by the general process of Example 23.

EXAMPLE 24

3,5-diphenyl-1-methoxy-4(1H)-pyridone, m.p. 165° C., yield 95%

EXAMPLE 25

3-(3-fluorophenyl)-1-methyl-5-phenyl-4(1H)-pyridone, m.p. 133.5° C., yield 69%

EXAMPLE 26

3-(4-bromophenyl)-1-methyl-5-phenyl-4(1H)-pyridone, m.p. 172° C., yield 63%

EXAMPLE 27

3-(4-methoxyphenyl)-1-methyl-5-phenyl-4(1H)-pyridone, m.p. 165° C., yield 32%

EXAMPLE 28

3-(3-chlorophenyl)-1-methyl-5-phenyl-4(1H)-pyridone, m.p. 172.5° C., yield 27%

EXAMPLE 29

3-(4-chlorophenyl)-1-methyl-5-phenyl-4(1H)-pyridone, m.p. 141.5° C., yield 76%

EXAMPLE 30

1-methyl-3-(1-naphthyl)-5-phenyl-4(1H)-pyridone, NMR peaks at 204 and 483 CPS; aromatic protons at 430-470 CPS; yield 12%

EXAMPLE 31

3,5-bis(3-chlorophenyl)-1-methyl-4(1H)-pyridone, m.p. 164°-167° C., yield 59%

EXAMPLE 32

1-methyl-3-(3-methylphenyl)-5-phenyl-4(1H)-pyridone (complex containing 1/2 mole of benzene), m.p. 79.5° C., yield 25%

EXAMPLE 33

1-methyl-3-(4-methylphenyl)-5-phenyl-4(1H)-pyridone, m.p. 144.5° C., yield 28%

EXAMPLE 34

1-methyl-3-(2-methylphenyl)-5-phenyl-4(1H)-pyridone, NMR peaks at 133 and 201 CPS; aromatic protons at 420-440 and 442-460 CPS; yield 16%

EXAMPLE 35

3-(4-fluorophenyl)-1-methyl-5-phenyl-4(1H)-pyridone, m.p. 166° C., yield 60%

EXAMPLE 36

1-methyl-3-phenyl-5-(3-trifluoromethylphenyl)-4(1H)-pyridone, m.p. 152°–156° C., yield 52%

EXAMPLE 37

3-(3-methoxyphenyl)-1-methyl-5-phenyl-4(1H)-pyridone, NMR peaks at 200 and 220 CPS; aromatic protons at 420–440 and 442–460 CPS; yield 33%

EXAMPLE 38

3-(3,4-dichlorophenyl)-1-methyl-5-phenyl-4(1H)-pyridone, m.p. 166.5° C., yield 54%

EXAMPLE 39

3-(2,5-dichlorophenyl)-1-methyl-5-phenyl-4(1H)-pyridone, m.p. 155.5° C., yield 22%

EXAMPLE 40

3-(2-chlorophenyl)-1-methyl-5-phenyl-4(1H)-pyridone, m.p. 145° C., yield 29%

EXAMPLE 41

3,5-bis(3-fluorophenyl)-1-methyl-4(1H)-pyridone, m.p. 149°–151° C., yield 60%

EXAMPLE 42

3-(3-chlorophenyl)-5-(3-fluorophenyl)-1-methyl-4(1H)-pyridone, m.p. 145°–146° C., yield 64%

EXAMPLE 43

3-(3,5-dichlorophenyl)-1-methyl-5-phenyl-4(1H)-pyridone, m.p. 131°–135° C., yield 28%

EXAMPLE 44

3,5-bis(3-bromophenyl)-1-methyl-4(1H)-pyridone, m.p. 216.5° C., yield 43%

EXAMPLE 45

3-(3-bromophenyl)-1-methyl-5-phenyl-4(1H)-pyridone, m.p. 172° C., yield 38%

EXAMPLE 46

3-(2-fluorophenyl)-1-methyl-5-phenyl-4(1H)-pyridone, m.p. 165° C., yield 19%

EXAMPLE 47

3-(3-bromophenyl)-1-methyl-5-(3-trifluoromethylphenyl)-4(1H)-pyridone, m.p. 151°–153° C., yield 37%

EXAMPLE 48

1-(1-carboxyethyl)-3-phenyl-5-(3-trifluoromethylphenyl)-4(1H)-pyridone, m.p. 236°–237° C., yield 13%

EXAMPLE 49

1-dimethylamino-3,5-diphenyl-4(1H)-pyridone, m.p. 143° C., yield 94%

EXAMPLE 50

1-methyl-3-(2-naphthyl)-5-phenyl-4(1H)-pyridone, m.p. 101°–105° C., yield 45%

EXAMPLE 51

1-ethyl-3-phenyl-5-(3-trifluoromethylphenyl)-4(1H)-pyridone, m.p. 98°–100° C., yield 66%

EXAMPLE 52

3-phenyl-1-propyl-5-(3-trifluoromethylphenyl)-4(1H)-pyridone, NMR, triplet peaks at 60 and 230 CPS, and a sextuplet at 114 CPS; yield 42%

EXAMPLE 53

1-methoxy-3-phenyl-5-(3-trifluoromethylphenyl)-4(1H)-pyridone, NMR peak at 248 CPS

EXAMPLE 54

3-(3-chlorophenyl)-1-methyl-5-(3-trifluoromethylphenyl)-4(1H)-pyridone, m.p. 133°–135° C., yield 28%

EXAMPLE 55

3-(4-biphenylyl)-1-methyl-5-phenyl-4(1H)-pyridone, m.p. 186°–190° C., yield 1%

EXAMPLE 56

3-(3-biphenylyl)-1-methyl-5-phenyl-4(1H)-pyridone, m.p. 186°–190° C., yield 2%

The following compound was prepared from the compound of Example 36 by refluxing for four hours in 60% sulfuric acid.

EXAMPLE 57

3-(3-carboxyphenyl)-1-methyl-5-phenyl-4(1H)-pyridone, m.p. 265°–267° C., yield 75%

The following typical salt compounds were prepared by making the free base compounds according to the general procedure of Example 23, and forming the salts by contact with the appropriate acids in aqueous solvents.

EXAMPLE 58

1-methyl-3,5-diphenyl-4(1H)-pyridone, hydroiodide, m.p. 110° C., yield 100%

EXAMPLE 59

1-methyl-3,5-diphenyl-4(1H)-pyridone, hydrochloride, m.p. 187°–194° C., yield 100%

The next example shows how 1-acetoxy compounds are prepared.

EXAMPLE 60

1-acetoxy-3,5-diphenyl-4(1H)-pyridone

A 2.4 g. portion of 3,5-diphenyl-1-hydroxy-4(1H)-pyridone was made by the process of Example 23, using hydroxylamine as the aminating agent. The pyridone was added to 25 ml. of acetic anhydride and the mixture was heated on the steam bath for about 1 hour. The volatiles were then evaporated under vacuum, and the residue was washed with benzene and then recrystallized, first from benzene and then from chloroform-hexane. The yield was 2.1 g. of 1-acetoxy-3,5-diphenyl-4(1H)-pyridone, m.p. 197°–199° C.

The following compound was also produced by the process of Example 60.

EXAMPLE 61

1-acetoxy-3-phenyl-5-(3-trifluoromethylphenyl)-4(1H)-pyridone, m.p. 232°–235° C., yield 5%

The following example illustrates the synthesis of pyridones by the di(aminoformylation) of ketones, followed by exchange with amines.

EXAMPLE 62

1-methyl-3-phenyl-4(1H)-pyridone

A mixture of 26.8 g. of phenylacetone and 71.4 g. of dimethylformamide dimethyl acetal in 100 ml. of anhydrous dimethylformamide was refluxed for 5 days. The reaction mixture was then evaporated to dryness under vacuum. Analysis of the remaining dark red oil showed that it consisted of about 75% of the desired 1,5-di(-dimethylamino)-2-phenyl-1,4-pentadien-3-one, and about 25% of the corresponding monoaminoformylated compound. The yield was 30 g., and the intermediate was used without purification.

The mixture prepared above was dissolved in 100 ml. of denatured ethanol, and 30 g. of methylamine hydrochloride was added. The mixture was refluxed overnight, and the solvent was removed under vacuum. The residue was taken up in methylene chloride, and the solution was washed with water and saturated aqueous sodium chloride solution. The washed organic layer was dried over magnesium sulfate, and the solvent was removed under vacuum. The remaining oil was shaken with ethyl ether. The solid product which precipitated from the ether was washed with further ether and air dried. The product was recrystallized from isopropyl ether-methylene chloride to produce 10 g. of purified 1-methyl-3-phenyl-4(1H)-pyridone, m.p. 123°–125° C.

EXAMPLE 63

3-bromo-1-methyl-5-phenyl-4(1H)-pyridone

A 3 g. portion of the product of Example 62 was dissolved in 100 ml. of water, and aqueous bromine was added dropwise until no more precipitate formed on further addition. The precipitate was removed by filtration, washed with water and air dried. The product was recrystallized from ethanol to yield 3 g. of 3-bromo-1-methyl-5-phenyl-4(1H)-pyridone, m.p. 195°–197° C.

The procedure of Example 62, and of Example 63 where appropriate, was used to prepare the following compounds.

EXAMPLE 64

3-bromo-1-methyl-5-(3-trifluoromethylphenyl)-4(1H)-pyridone, m.p. 167°–169° C., yield 76%

EXAMPLE 65

1-methyl-3-(3-trifluoromethylphenyl)-4(1H)-pyridone, m.p. 122°–123° C., yield 16%

EXAMPLE 66

3-chloro-1-methyl-5-(3-trifluoromethylphenyl)-4(1H)-pyridone, m.p. 170°–172° C., yield 67%

EXAMPLE 67

3-(3-carboxyphenyl)-1-methyl-5-phenyl-4(1H)-pyridone, hydrochloride, m.p. 266°–268° C., yield 10%

EXAMPLE 68

3-(3-cyanophenyl)-1-methyl-5-phenyl-4(1H)-pyridone, m.p. 164°–166° C., yield 33%

EXAMPLE 69

3-(3-ethoxycarbonylphenyl)-1-methyl-5-phenyl-4(1H)-pyridone, m.p. 167°–168° C., yield 11%

EXAMPLE 70

3,5-bis(3-cyanophenyl)-1-methyl-4(1H)-pyridone, m.p. 322°–327° C., yield 22%

EXAMPLE 71

1-methyl-3-phenyl-5-(3-thienyl)-4(1H)-pyridone, NMR peaks at 204 and 495 CPS; aromatic protons at 430–460 CPS; yield 34%

EXAMPLE 72

1-methyl-3-(2-methylphenyl)-5-(3-trifluoromethylphenyl)-4(1H)-pyridone, m.p. 144°–147° C., yield 5%

EXAMPLE 73

1-methyl-3-(3-methylphenyl)-5-(3-trifluoromethylphenyl)-4(1H)-pyridone, m.p. 155°–157° C., yield 2.4%

EXAMPLE 74

1-methyl-3-(4-methylphenyl)-5-(3-trifluoromethylphenyl)-4(1H)-pyridone, m.p. 154°–156° C., yield 6%

EXAMPLE 75

5-(3-methoxycarbonylphenyl)-1-methyl-3-(4-methylphenyl)-4(1H)-pyridone, m p. 85°–88° C., yield 5%

EXAMPLE 76

5-(3-methoxycarbonylphenyl)-1-methyl-3-(3-methylphenyl)-4(1H)-pyridone, m.p. 180°–183° C., yield 1%

EXAMPLE 77

3-methoxy-1-methyl-5-(3-trifluoromethylphenyl)-4(1H)-pyridone, m.p. 173°–175° C., yield 18%

EXAMPLE 78

3-(4-bromophenyl)-1-methyl-5-(3-methylphenyl)-4(1H)-pyridone, m.p. 201°–204° C., yield 21%

EXAMPLE 79

3-(3,4-dichlorophenyl)-1-methyl-5-(3-trifluoromethylphenyl)-4(1H)-pyridone, m.p. 109°–112° C., yield 4%

EXAMPLE 80

3,5-bis(3,5-dichlorophenyl)-1-methyl-4(1H)-pyridone, m.p. 275°–278° C., yield 14%

EXAMPLE 81

3-(3,4-dichlorophenyl)-1-methyl-5-(3-methylphenyl)-4(1H)-pyridone, mass spectrometry MI, 342, yield 10%

EXAMPLE 82

3-(3,4-dichlorophenyl)-5-(3,4-dimethylphenyl)-1-methyl-4(1H)-pyridone, m.p. 150°–152° C., yield 6%

EXAMPLE 83

3-(3-chlorophenyl)-1-methyl-5-(2-methylphenyl)-4(1H)-pyridone, m.p. 171°–173° C., yield 12%

EXAMPLE 84

3-(4-bromophenyl)-1-methyl-5-(3-trifluoromethylphenyl)-4(1H)-pyridone, m.p. 144°–146° C., yield 30%

The following compound was produced by refluxing the compound above in 60% sulfuric acid.

EXAMPLE 85

3-(4-bromophenyl)-5-(3-carboxyphenyl)-1-methyl-4(1H)-pyridone, m.p. 259°–263° C., yield 50%

The following compounds were made by the process of Example 62.

EXAMPLE 86
3-(3-chlorophenyl)-1-methyl-5-(4-trifluoromethylphenyl)-4(1H)-pyridone, m.p. 147°-151° C., yield 2%

EXAMPLE 87
3-(2-methylphenyl)-5-(4-methylphenyl)-1-methyl-4(1H)-pyridone, m.p. 151°-154° C., yield 6%

EXAMPLE 88
3-(3-methylphenyl)-5-(4-methylphenyl)-1-methyl-4(1H)-pyridone, m.p. 155°-157° C., yield 28%

EXAMPLE 89
3-(2-chlorophenyl)-5-(2-methylphenyl)-1-methyl-4(1H)-pyridone, m.p. 87°-91° C., yield 1%

EXAMPLE 90
1-methyl-3,5-bis(4-methylphenyl)-4(1H)-pyridone, m.p. 212°-214° C., yield 3%

EXAMPLE 91
1-methyl-3-(3-chlorophenyl)-5-(3,4-dichlorophenyl)-4(1H)-pyridone, m.p. 107°-110° C., yield 10%

EXAMPLE 92
1-methyl-3-(3,4-dichlorophenyl)-5-(2-methylphenyl)-4(1H)-pyridone, m.p. 103°-106° C., yield 10%

EXAMPLE 93
1-methyl-3-(2-chlorophenyl)-5-(3,4-dichlorophenyl)-4(1H)-pyridone, m.p. 169°-171° C., yield 25%

EXAMPLE 94
1-methyl-3-(3-bromophenyl)-5-(3,4-dichlorophenyl)-4(1H)-pyridone, m.p. 152°-154° C., yield 10%

EXAMPLE 95
1-methyl-3-(3,5-dichlorophenyl)-5-(3-trifluoromethylphenyl)-4(1H)-pyridone, m.p. 156°-160° C., yield 30%

EXAMPLE 96
1-methyl-3-(3-bromophenyl)-5-(3-methylphenyl)-4(1H)-pyridone, m.p. 144°-147° C., yield 3%

EXAMPLE 97
1-methyl-3,5-bis(3-methylphenyl)-4(1H)-pyridone, m.p. 148°-150° C., yield 8%

EXAMPLE 98
1-methyl-3-(3-fluorophenyl)-5-(2,5-dimethylphenyl)-4(1H)-pyridone, mass spectroscopy MI, 307, yield 10%

EXAMPLE 99
3-(3-bromophenyl)-1-methyl-5-(2-methylphenyl)-4(1H)-pyridone, mass spectroscopy MI, 353, yield 2%

EXAMPLE 100
3-(3-bromophenyl)-5-(2-chlorophenyl)-1-methyl-4(1H)-pyridone, m.p. 177°-179° C., yield 10%

EXAMPLE 101
3-(2-bromophenyl)-1-methyl-5-(3-trifluoromethylphenyl)-4(1H)-pyridone, m.p. 197°-199° C., yield 15%

EXAMPLE 102
3-(2,3-dimethoxyphenyl)-1-methyl-5-(3-trifluoromethylphenyl)-4(1H)-pyridone, m.p. 153°-155° C., yield 20%

EXAMPLE 103
3-(2-methoxyphenyl)-1-methyl-5-(3-trifluoromethylphenyl)-4(1H)-pyridone, m.p. 193°-196° C., yield 10%

EXAMPLE 104
3-(2-ethylphenyl)-1-methyl-5-(3-trifluoromethylphenyl)-4(1H)-pyridone, m.p. 123°-125° C., yield 15%

EXAMPLE 105
3-(3-bromo-4-methylphenyl)-1-methyl-5-(3-trifluoromethylphenyl)-4(1H)-pyridone, m.p. 158°-161° C., yield 30%

EXAMPLE 106
3-(3-ethoxy-4-methoxyphenyl)-1-methyl-5-(3-trifluoromethylphenyl)-4(1H)-pyridone, mass spectroscopy MI, 403, yield 10%

The following example demonstrates the synthesis process starting from a carbonyl halide. The corresponding enaminoketone is first formed by reaction with an enamine, the enaminoketone is aminoformylated, and the pyridone is formed by exchange with an amine.

EXAMPLE 107
3-cyano-1-methyl-5-phenyl-4(1H)-pyridone

A mixture of 1.92 g. of dimethylaminoacrylonitrile and 1.6 g. of pyridine was dissolved in 25 ml. of ethyl ether at 0° C. A 3.08 g. portion of phenylacetyl chloride in 25 ml. of ethyl ether was added dropwise, and the mixture was stirred for 2 hours at 0° C. after completion of the addition. The mixture was then evaporated to dryness under vacuum. The residue was taken up in methylene chloride, washed with water, dried and evaporated to dryness again. Upon standing, the mixture began to crystallize, and the solids were separated by filtration and recrystallized from isopropanol to yield 400 mg. of 2-cyano-1-dimethylamino-4-phenyl-1-buten-3-one.

A 300 mg. portion of the above enaminoketone and 10 ml. of dimethylformamide dimethyl acetal was heated at reflux temperature for 12 hours. The mixture was then evaporated under vacuum. To the residue was added 25 ml. of denatured ethanol and 1 g. of methylamine hydrochloride. The ethanol solution was heated at reflux for 12 hours more and evaporated to dryness, and the residue was taken up in methylene chloride. After washing with water and drying, the organic solution was evaporated to dryness, and the residue was triturated in ethyl ether and filtered. The solids were recrystallized from isopropyl ether-acetone to yield 260 mg. of 3-cyano-1-methyl-5-phenyl-4(1H)-pyridone, m.p. 209°-210° C.

The following exemplary compounds were prepared according to the general process of Example 107 above.

EXAMPLE 108
1,3-dimethyl-5-(3-trifluoromethylphenyl)-4(1H)-pyridone, m.p. 130°-131° C., yield 12%

EXAMPLE 109

1,3-dimethyl-5-phenyl-4(1H)-pyridone, m.p. 111°–113° C., yield 8%

EXAMPLE 110

3-(3-chlorophenyl)-1,5-dimethyl-4(1H)-pyridone, m.p. 143°–143.5° C., yield 6%

EXAMPLE 111

3-ethyl-1-methyl-5-(3-trifluoromethylphenyl)-4(1H)-pyridone, m.p. 95.5°–96.5° C., yield 7%

EXAMPLE 112

3-cyclohexyl-1-methyl-5-(3-trifluoromethylphenyl)-4(1H)-pyridone, m.p. 174°–175° C., yield 40%

EXAMPLE 113

3-isopropyl-1-methyl-5-(3-trifluoromethylphenyl)-4(1H)-pyridone, m.p. 98.5°–99.5° C., yield 10%

EXAMPLE 114

3-hexyl-1-methyl-5-(3-trifluoromethylphenyl)-4(1H)-pyridone, m.p. 89.5°–90.5° C., yield 7%

EXAMPLE 115

3-benzyl-1-methyl-5-(3-trifluoromethylphenyl)-4(1H)-pyridone, m.p. 98°–100° C., yield 18%

EXAMPLE 116

3-butyl-1-methyl-5-(3-trifluoromethylphenyl)-4(1H)-pyridone, m.p. 82.5°–84° C., yield 9%

EXAMPLE 117

3-(3-cyclohexenyl)-1-methyl-5-(3-trifluoromethylphenyl)-4(1H)-pyridone, m.p. 194°–195° C., yield 43%

EXAMPLE 118

1-methyl-3-propyl-5-(3-trifluoromethylphenyl)-4(1H)-pyridone, m.p. 45°–47° C., yield 3%

EXAMPLE 119

1-methyl-3-(4-nitrophenyl)-5-phenyl-4(1H)-pyridone, m.p. 212°–214° C., yield 48%

EXAMPLE 120

3,5-bis(3,4-dimethoxyphenyl)-1-methyl-4(1H)-pyridone, m.p. 182°–184° C., yield 1%

EXAMPLE 121

3-ethoxycarbonyl-1-methyl-5-phenyl-4(1H)-pyridone, m.p. 107°–108° C., yield 68%

EXAMPLE 122

3-(2-furyl)-1-methyl-5-phenyl-4(1H)-pyridone, m.p. 191°–192° C., yield 69%

EXAMPLE 123

3-cyano-1-methyl-5-(3-trifluoromethylphenyl)-4(1H)-pyridone, m.p. 228°–229° C., yield 40%

EXAMPLE 124

3-(3,4-dimethoxyphenyl)-1-methyl-5-phenyl-4(1H)-pyridone, m.p. 154°–157° C., yield 4%

EXAMPLE 125

3-(3,4-dibromocyclohexyl)-1-methyl-5-(3-trifluoromethylphenyl)-4(1H)-pyridone, hydrobromide, m.p. 196°–198° C., yield 26%, made by bromination of the corresponding 3-(3-cyclohexenyl) compound

EXAMPLE 126

3-(3-isopropenylphenyl)-1-methyl-5-phenyl-4(1H)-pyridone, NMR peaks at 125, 214, 302 and 327 CPS; aromatic protons at 420–470 CPS; yield 4%

EXAMPLE 127

3-(3-ethylphenyl)-1-methyl-5-phenyl-4(1H)-pyridone, m.p. 135°–137° C., yield 5%

EXAMPLE 128

3-(3-hexylphenyl)-1-methyl-5-phenyl-4(1H)-pyridone, m.p. 93°–95° C., yield 6%

EXAMPLE 129

3-(4-ethylphenyl)-1-methyl-5-phenyl-4(1H)-pyridone, m.p. 143°–145° C., yield 6%

EXAMPLE 130

3-(3-cyclohexylmethylphenyl)-1-methyl-5-phenyl-4(1H)-pyridone, m.p. 147°–148° C., yield 9%

EXAMPLE 131

1-methyl-3-phenyl-5-benzylthio-4(1H)-pyridone, m.p. 155°–157° C., yield 36%

EXAMPLE 132

1-methyl-3-phenyl-5-phenylthio-4(1H)-pyridone, m.p. 164°–165° C., yield 18%

EXAMPLE 133

1-methyl-3-phenoxy-5-phenyl-4(1H)-pyridone, m.p. 176°–177° C., yield 19%

EXAMPLE 134

1-methyl-3-phenyl-5-phenylsulfonyl-4(1H)-pyridone, m.p. 218°–220° C., yield 50%, made by oxidation of the corresponding phenylthio compound with m-chloroperbenzoic acid.

EXAMPLE 135

3-(4-methoxy-3-methylphenyl)-1-methyl-5-phenyl-4(1H)-pyridone, m.p. 157°–160° C., yield 2.5%

EXAMPLE 136

3-(3-bromo-4-methylphenyl)-1-methyl-5-phenyl-4(1H)-pyridone, m.p. 168°–170° C., yield 13%

EXAMPLE 137

1-methyl-3-(3-nitrophenyl)-5-(3-trifluoromethylphenyl)-4(1H)-pyridone, m.p. 209°–211° C., yield 51%

EXAMPLE 138

1-methyl-3-phenyl-5-(3-phenylthiophenyl)-4(1H)-pyridone, mass spectrometry MI, 369, yield 8%

The following compound was prepared by oxidizing the compound above with hydrogen peroxide in acetic acid.

EXAMPLE 139

1-methyl-3-phenyl-5-(3-phenylsulfonylphenyl)-4(1H)-pyridone, m.p. 65°–72° C., yield 48%

The following compounds are also prepared by following the process of Example 107.

EXAMPLE 140

3-(2-chloro-4-fluorophenyl)-1-methyl-5-phenyl-4(1H)-pyridone, m.p. 190°–192° C., yield 5%

EXAMPLE 141

3-(3,4-dimethylphenyl)-1-methyl-5-phenyl-4(1H)-pyridone, m.p. 108°–111° C., yield 5%

EXAMPLE 142

3-(3,5-dimethylphenyl)-1-methyl-5-phenyl-4(1H)-pyridone, m.p. 148°–150° C., yield 10%

EXAMPLE 143

3-(3-butylphenyl)-1-methyl-5-phenyl-4(1H)-pyridone, m.p. 87°–89° C., yield 6%

EXAMPLE 144

3-(2,5-dimethylphenyl)-1-methyl-5-phenyl-4(1H)-pyridone, m.p. 188°–190° C., yield 4%

EXAMPLE 145

3-(2,4-dimethylphenyl)-1-methyl-5-phenyl-4(1H)-pyridone, m.p. 153°–155° C., yield 3%

EXAMPLE 146

1-methyl-3-phenoxy-5-(3-trifluoromethylphenyl)-4(1H)-pyridone, m.p. 144°–145° C., yield 15%

EXAMPLE 147

3-ethoxycarbonyl-1-methyl-5-(3-trifluoromethylphenyl)-4(1H)-pyridone, m.p. 151°–152° C., yield 62%

EXAMPLE 148

1-methyl-3-(3-trifluoromethylphenyl)-5-phenylthio-4(1H)-pyridone, m.p. 164°–165° C., yield 18%

EXAMPLE 149

3-(2,4-dichlorophenoxy)-1-methyl-5-(3-trifluoromethylphenyl)-4(1H)-pyridone, m.p. 129°–130° C., yield 40%.

EXAMPLE 150

1-methyl-3-(2-thienyl)-5-(3-trifluoromethylphenyl)-4(1H)-pyridone, m.p. 185°–186° C., yield 84%

EXAMPLE 151

3-ethylthio-1-methyl-5-phenyl-4(1H)-pyridone, m.p. 94°–95° C., yield 40%

EXAMPLE 152

3-ethylthio-1-methyl-5-(3-trifluoromethylphenyl)-4(1H)-pyridone, m.p. 84°–85° C., yield 40%

The following exemplary compound was prepared by oxidation of the compound of Example 152 with hydrogen peroxide in methylene dichloride at about 0° C.

EXAMPLE 153

3-ethylsulfonyl-1-methyl-5-(3-trifluoromethylphenyl)-4(1H)-pyridone, m.p. 196°–198° C., yield 70%

The following compound was prepared by oxidizing the compound of Example 152 with sodium periodate in aqueous ethanol at room temperature for 16 hours.

EXAMPLE 154

3-ethylsulfinyl-1-methyl-5-(3-trifluoromethylphenyl)-4(1H)-pyridone, m.p. 146°–148° C., yield 82%

The following compounds were also made by the process of Example 107.

EXAMPLE 155

3-(5-bromo-2-fluorophenyl)-1-methyl-5-phenyl-4(1H)-pyridone, m.p. 148°–150° C., yield 6%

EXAMPLE 156

1-methyl-3-(5-nitro-2-methylphenyl)-5-phenyl-4(1H)-pyridone, m.p. 185°–187° C., yield 5%

EXAMPLE 157

3-cyano-5-(2,5-dimethoxyphenyl)-1-methyl-4(1H)-pyridone, m.p. 209°–211° C., yield 4%

EXAMPLE 158

3-(2,6-dichlorophenyl)-1-methyl-5-phenyl-4(1H)-pyridone, m.p. 223°–226° C., yield 20%

EXAMPLE 159

3-ethoxycarbonyl-1-methyl-5-phenyl-4(1H)-pyridone, m.p. 107°–108° C., yield 68%

EXAMPLE 160

1-methyl-3-propylthio-5-(3-trifluoromethylphenyl)-4(1H)-pyridone, m.p. 101°–102° C., yield 25%

EXAMPLE 161

3-butylthio-1-methyl-5-(3-trifluoromethylphenyl)-4(1H)-pyridone, m.p. 109°–110° C., yield 35%

EXAMPLE 162

1-methyl-3-methylthio-5-(3-trifluoromethylphenyl)-4(1H)-pyridone, m.p. 121°–122° C., yield 20%

EXAMPLE 163

1-methyl-3-(3-trifluoromethylphenyl)-5-(4-trifluoromethylphenyl)-4(1H)-pyridone, m.p. 110°–113° C., yield 10%

EXAMPLE 164

1-methyl-3-(3-trifluoromethylphenyl)-5-trifluoromethylthio-4(1H)-pyridone, m.p. 122°–124° C., yield 21%

EXAMPLE 165

3-(3,4-dimethoxyphenyl)-1-methyl-5-(3-trifluoromethylphenyl)-4(1H)-pyridone, m.p. 148°–150° C., yield 10%

EXAMPLE 166

Mixture of 3-(5-fluoro-2-iodophenyl)-1-methyl-5-phenyl-4(1H)-pyridone and 3-(2-bromo-5-fluorophenyl)-1-methyl-5-phenyl-4(1H)-pyridone, mixed m.p. 211°–214° C., yield 7%

EXAMPLE 167

3-benzylthio-1-methyl-5-(3-trifluoromethylphenyl)-4(1H)-pyridone, m.p. 121°–122° C., yield 40%

EXAMPLE 168

3-(4-benzyloxyphenyl)-1-methyl-5-(3-trifluoromethylphenyl)-4(1H)-pyridone, amorphous, yield 10%

EXAMPLE 169

1,3-diethyl-5-(3-trifluoromethylphenyl)-4(1H)-pyridone, m.p. 67°–70° C., yield 3%

The compound below was prepared by the hydrogenation of Example 168 in acetic acid in the presence of 5% palladium on carbon hydrogenation catalyst.

EXAMPLE 170

3-(4-hydroxyphenyl)-1-methyl-5-(3-trifluoromethylphenyl)-4(1H)-pyridone, m.p. 162°-163° C., yield 50%

The general process of Example 107 was used to prepare the compounds below.

EXAMPLE 171

3-(4-chloro-3-trifluoromethylphenyl)-5-ethoxy-1-methyl-4(1H)-pyridone, m.p. 158°-159° C., yield 15%

EXAMPLE 172

1-methyl-3-isopropylthio-5-(3-trifluoromethylphenyl)-4(1H)-pyridone, m.p. 93°-94° C., yield 32%

EXAMPLE 173

3-(4-chloro-3-trifluoromethylphenyl)-5-ethylthio-1-methyl-4(1H)-pyridone, m.p. 115°-116° C., yield 11%

EXAMPLE 174

3-(4-chloro-3-trifluoromethylphenyl)-1-methyl-5-phenyl-4(1H)-pyridone, m.p. 154°-155° C., yield 17%

EXAMPLE 175

3-(2,5-dimethylphenyl)-1-methyl-5-(3-trifluoromethylphenyl)-4(1H)-pyridone, m.p. 165°-167° C., yield 2%

EXAMPLE 176

3-(3,5-dimethylphenyl)-1-methyl-5-(3-trifluoromethylphenyl)-4(1H)-pyridone, m.p. 160°-163° C., yield 6%

EXAMPLE 177

3-(2,4-dichlorophenyl)-1-methyl-5-(3-trifluoromethylphenyl)-4(1H)-pyridone, m.p. 139°-142° C., yield 11%

EXAMPLE 178

1-methyl-3-phenyl-5-(2-trifluoromethylphenyl)-4(1H)-pyridone, m.p. 168°-171° C., yield 14%

EXAMPLE 179

1-methyl-3-(2-trifluoromethylphenyl)-5-(3-trifluoromethylphenyl)-4(1H)-pyridone, m.p. 135°-138° C., yield 24%

EXAMPLE 180

3-(3,4-dimethylphenyl)-1-methyl-5-(3-trifluoromethylphenyl)-4(1H)-pyridone, m.p. 150°-153° C., yield 15%

EXAMPLE 181

3-(3-iodophenyl)-1-methyl-5-(3-trifluoromethylphenyl)-4(1H)-pyridone, m.p. 178°-181° C., yield 15%

EXAMPLE 182

3-ethyl-1-methyl-5-(3-methoxyphenyl)-4(1H)-pyridone, yield 5%, mass spectroscopy MI, 243

EXAMPLE 183

1-methyl-3-(3-iodophenyl)-5-phenyl-4(1H)-pyridone, m.p. 190°-193° C., yield 8%

EXAMPLE 184

1-methyl-3-(4-methoxyphenoxy)-5-(3-trifluoromethylphenyl)-4(1H)-pyridone, m.p. 119°-120° C., yield 25%

EXAMPLE 185

1-methyl-3-(2-chloro-4-fluorophenyl)-5-(3-trifluoromethylphenyl)-4(1H)-pyridone, m.p. 183°-186° C., yield 20%

EXAMPLE 186

1-methyl-3-(4-chloro-3-trifluoromethylphenyl)-5-trifluoromethyl-4(1H)-pyridone, m.p. 164°-165° C., yield 2%

EXAMPLE 187

1-methyl-3-(4-chloro-3-trifluoromethylphenyl)-5-propyl-4(1H)-pyridone, m.p. 141°-142° C., yield 8%

EXAMPLE 188

1-methyl-3-isopropylthio-5-(4-chloro-3-trifluoromethylphenyl)-4(1H)-pyridone, m.p. 127°-129° C., yield 15%

EXAMPLE 189

1-methyl-3-(4-chloro-3-trifluoromethylphenyl)-5-propylthio-4(1H)-pyridone, m.p. 128°-130° C., yield 15%

EXAMPLE 190

1-methyl-3-(4-chloro-3-trifluoromethylphenyl)-5-(2-thienyl)-4(1H)-pyridone, m.p. 166°-168° C., yield 10%

EXAMPLE 191

3-ethyl-1-methyl-5-(4-chloro-3-trifluoromethylphenyl)-4(1H)-pyridone, m.p. 121°-123° C., yield 1%

EXAMPLE 192

1-methyl-3-(2,4-dimethylphenyl)-5-(3-trifluoromethylphenyl)-4(1H)-pyridone, m.p. 128°-131° C., yield 6%

EXAMPLE 193

3-isopropoxy-1-methyl-5-(3-trifluoromethylphenyl)-4(1H)-pyridone, mass spectroscopy MI, 311, yield 1%

EXAMPLE 194

1-methyl-3-(4-chlorophenoxy)-5-(3-trifluoromethylphenyl)-4(1H)-pyridone, m.p. 90°-91° C., yield 15%

EXAMPLE 195

1-methyl-3-(3-methylthiophenyl)-5-(3-trifluoromethylphenyl)-4(1H)-pyridone, m.p. 150°-153° C., yield 25%

The following compound was prepared by oxidation of the compound of Example 195 with hydrogen peroxide in pyridine at room temperature.

EXAMPLE 196

1-methyl-3-(3-methylsulfonylphenyl)-5-(3-trifluoromethylphenyl)-4(1H)-pyridone, m.p. 180°-183° C., yield 20%

The general process of Example 107 was used to prepare the following compounds.

EXAMPLE 197

1-methyl-3-(3-trifluoromethylphenoxy)-5-(3-trifluoromethylphenyl)-4(1H)-pyridone, m.p. 93°–95° C., yield 40%

EXAMPLE 198

3-(4-methoxyphenyl)-1-methyl-5-(3-trifluoromethylphenyl)-4(1H)-pyridone, m.p. 160°–162° C., yield 40%

EXAMPLE 199

3-(2,3-dichlorophenoxy)-1-methyl-5-(3-trifluoromethylphenyl)-4(1H)-pyridone, m.p. 200°–202° C., yield 30%

EXAMPLE 200

3-(3,5-dichlorophenoxy)-1-methyl-5-(3-trifluoromethylphenyl)-4(1H)-pyridone, m.p. 128°–130° C., yield 30%

EXAMPLE 201

3-(3,4-dichlorophenoxy)-1-methyl-5-(3-trifluoromethylphenyl)-4(1H)-pyridone, m.p. 127°–129° C., yield 20%

EXAMPLE 202

3-(4-chloro-3-trifluoromethylphenyl)-1-methyl-5-isopropyl-4(1H)-pyridone, m.p. 85°–87° C., yield 25%

EXAMPLE 203

3-(2,5-dichlorophenoxy)-1-methyl-5-(3-trifluoromethylphenyl)-4(1H)-pyridone, m.p. 162°–164° C., yield 28%

The next example illustrates a synthesis similar to the synthesis of Example 107, except that the enaminoketone is reacted first with an amine, and then with an aminoformylating agent to form the desired pyridone.

EXAMPLE 204

1-methyl-3-(3-methylthiophenyl)-5-phenyl-4(1H)-pyridone

An enaminoketone was made according to the procedure of the first step of Example 107 above, starting with 17.5 g. of N,N-diethylstyrylamine and 15 g. of (3-methylthiphenyl)acetyl chloride. The enaminoketone was dissolved in 300 ml. of ethanol, mixed with 20 g. of methylamine hydrochloride and stirred for about 60 hours. The solvent was then evaporated, the residue was extracted with ethyl ether, and the solution was washed with water. The organic layer was dried over anhydrous sodium sulfate, and the dried solution was evaporated to dryness.

The residue was mixed with 50 ml. of dimethylformamide dimethyl acetal and heated at reflux temperature for 20 hours. The reaction mixture was then poured into water, and the mixture was extracted first with ether and then with methylene chloride. Both extracts were washed with water, dried and evaporated to dryness. The product was 9 g. of 1-methyl-3-(3-methylthiophenyl)-5-phenyl-4(1H)-pyridone, which was identified by NMR, which showed peaks at 144 and 227 CPS, with aromatic protons at 420–440 and 442–458 CPS.

By a similar process, the following compounds were also produced. Examples 205 and 206 were produced by oxidation of the compound of Example 204 with m-chloroperbenzoic acid.

EXAMPLE 205

1-methyl-3-(3-methylsulfinylphenyl)-5-phenyl-4(1H)-pyridone, m.p. 161°–164° C., yield 57%

EXAMPLE 206

1-methyl-3-(3-methylsulfonylphenyl)-5-phenyl-4(1H)-pyridone, m.p. 176°–181° C., yield 31%

EXAMPLE 207

1-methyl-3-phenyl-5-(4-trifluoromethylphenyl)-4(1H)-pyridone, m.p. 164°–166° C., yield 16%

The following example illustrates a variation of the process beginning with a carbonyl halide, wherein the enaminoketone is first exchanged with an amine, and the pyridone is then formed by formylation of the intermediate.

EXAMPLE 208

3-(3-benzyloxyphenyl)-1-methyl-5-phenyl-4(1H)-pyridone

An enaminoketone was prepared, following the first step of the procedure of Example 107 above, from 14.4 g. of (3-benzyloxyphenyl)acetyl chloride and 9.6 g. of N,N-diethylstyrylamine. A 13 g. portion of the enaminoketone was dissolved in 100 ml. of methanol and 26 g. of methylamine hydrochloride was added. The reaction mixture was heated at reflux temperature overnight. The solvent was removed under vacuum, 100 ml. of water was added, and the mixture was then extracted with methylene chloride. The extract was washed with dilute hydrochloric acid and then with water, and the organic layer was separated, dried, filtered and evaporated to dryness. The resulting intermediate, 4-(3-benzyloxyphenyl)-1-methylamino-2-phenyl-1-buten-3-one, was dissolved in 125 ml. of ethyl ether.

The solution was cooled to 5° C., and 12 g. of sodium methoxide was added. While the reaction mixture was held at about 5° C., 50 ml. of ethyl formate was added slowly. The mixture was then stirred as it was allowed to warm slowly to room temperature. The reaction mixture was then evaporated to dryness, the residue was extracted with chloroform, and the extract was washed with water and dried. The product was purified by chromatography over silica gel with a 50:50 mixture of ethyl acetate:hexane. The product-containing fractions were collected, combined, and evaporated to dryness. The product was recrystallized from ethyl acetate to produce 1.5 g. of 3-(3-benzyloxyphenyl)-1-methyl-5-phenyl-4(1H)-pyridone, m.p. 158°–160° C.

The following exemplary compounds were also produced according to the process of Example 208 above.

EXAMPLE 209

1-methyl-3-phenyl-5-(2-thienyl)-4(1H)-pyridone, m.p. 147°–148° C., yield 6%

EXAMPLE 210

3-(3-isobutylphenyl)-1-methyl-5-phenyl-4(1H)-pyridone, NMR doublets at 54 and 147 CPS; a septet at 113 CPS; aromatic protons at 420–460 CPS.

EXAMPLE 211

1-methyl-3-(3-nitrophenyl)-5-phenyl-4(1H)-pyridone, m.p. 135°–136.5° C., yield 33%

EXAMPLE 212

1-methyl-3-allylthio-5-(3-trifluoromethylphenyl)-4(1H)-pyridone, m.p. 74°–75° C., yield 5%

EXAMPLE 213

3-(4-chloro-3-trifluoromethylphenyl)-1-methyl-5-phenoxy-4(1H)-pyridone, m.p. 130°–131° C., yield 27%

EXAMPLE 214

1-methyl-3-phenyl-5-allylthio-4(1H)-pyridone, m.p. 136°–138° C., yield 15%

The next example illustrates a process similar to that above, but wherein the enaminoketone is first formylated and then exchanged with the amine to form the pyridone.

EXAMPLE 215

3-methoxy-1-methyl-5-phenyl-4(1H)-pyridone

An enaminoketone was formed from 3.5 g. of N,N-diethylstyrylamine and 2.16 g. of methoxyacetyl chloride in the presence of 2 g. of triethylamine. The yield was about 5 g. of the desired enaminoketone, 1-diethylamino-4-methoxy-2-phenyl-1-buten-3-one.

The above enaminoketone was mixed with 3.2 g. of sodium methoxide in 50 ml. of dry tetrahydrofuran at 0° C., and 4.4 g. of ethyl formate was added dropwise. After the mixture had stirred for three hours, 25 ml. of 40% aqueous methylamine was added, followed by 5 g. of methylamine hydrochloride. The mixture was stirred overnight at room temperature, and the solvents were removed under vacuum. The residue was taken up in methylene chloride, washed with water and saturated sodium chloride solution and dried. The solvent was then removed under vacuum, and the residue was triturated with ethyl ether. The solids were recrystallized from isopropyl ether-methylene chloride to produce 1 g. of 3-methoxy-1-methyl-5-phenyl-4(1H)-pyridone, m.p. 153°–155° C.

The following compound was also produced by the process of Example 215.

EXAMPLE 216

3-ethoxy-1-methyl-5-(3-trifluoromethylphenyl)-4(1H)-pyridone, m.p. 131°–133° C., yield 17%

The following examples illustrate the preparation of 3-hydroxyphenyl-substituted compounds, from which other substituted compounds are prepared in the next examples following.

EXAMPLE 217

3-(3-hydroxyphenyl)-1-methyl-5-phenyl-4(1H)-pyridone

A 1 g. portion of the product of Example 208 was dissolved in 250 ml. of acetic acid, and 1 g. of 5% palladium on carbon was added. The mixture was hydrogenated for about 45 minutes, filtered, and the filtrate was evaporated to dryness. The product was recrystallized from ethyl acetate-hexane to produce 0.45 g. of 3-(3-hydroxyphenyl)-1-methyl-5-phenyl-4(1H)-pyridone, m.p. 223°–225° C.

The same compound was also made by a cleavage with pyridine hydrochloride as follows.

A 2 g. portion of 3-(3-methoxyphenyl)-1-methyl-5-phenyl-4(1H)-pyridone was mixed with 15 g. of pyridine hydrochloride and the mixture was heated at reflux temperature for about 1 hour. The mixture was then poured into a large amount of water, and the precipitated solids were separated by filtration. The solids were then recrystallized from ethanol-ethyl ether to yield 1.1 g. of 3-(3-hydroxyphenyl)-1-methyl-5-phenyl-4(1H)-pyridone. An additional 0.65 g. was recovered by concentration of the filtrate above. The product was identical to that of the above example.

The following compound was made by a process similar to Example 217.

EXAMPLE 218

3-cyclohexyl-5-(3-hydroxyphenyl)-1-methyl-4(1H)-pyridone, m.p. 155°–165° C., yield 13%

EXAMPLE 219

3-(3-ethoxyphenyl)-1-methyl-5-phenyl-4(1H)-pyridone

A 3.2 g. portion of the product of Example 217 was added to a suspension of 0.86 g. of sodium hydride in 50 ml. of dimethylsulfoxide. The mixture was stirred at room temperature, and 3.5 g. of ethyl iodide was added. The mixture was stirred for two and one-half hours more, and extracted with ethyl acetate. The extract was washed with dilute hydrochloric acid and then with water, and dried. The dried extract was then filtered and concentrated to dryness under vacuum. The product was 2.2 g. of 3-(3-ethoxyphenyl)-1-methyl-5-phenyl-4(1H)-pyridone, m.p. 133°–135° C.

The exemplary compounds below were prepared according to methods similar to that of Example 219.

EXAMPLE 220

3-(3-allyloxyphenyl)-1-methyl-5-phenyl-4(1H)-pyridone, NMR peaks at 211 and 270 CPS; broad peaks at 296–328, 341–378 and 399–458 CPS; yield 10%

EXAMPLE 221

3-[3-(1-fluoro-2-iodovinyloxy)phenyl]-1-methyl-5-phenyl-4(1H)-pyridone, NMR peaks at 218 CPS; a broad peak at 270–316 CPS; aromatic protons at 416–464 CPS; yield 67%

EXAMPLE 222

3-(3-isopropoxyphenyl)-1-methyl-5-phenyl-4(1H)-pyridone, NMR peaks at 81, 209 and 276 CPS; aromatic protons at 401–468 CPS; yield 18%

EXAMPLE 223

3-(3-cyanomethoxyphenyl)-1-methyl-5-phenyl-4(1H)-pyridone, NMR peaks at 207 and 275 CPS; aromatic protons at 396–456 CPS; yield 6%

EXAMPLE 224

3-(3-dodecyloxyphenyl)-1-methyl-5-phenyl-4(1H)-pyridone, NMR peaks at 52, 207 and 234 CPS; a broad peak at 60–122 CPS; aromatic protons at 396–461 CPS; yield 26%

EXAMPLE 225

1-methyl-3-[3-(4-nitrophenoxy)phenyl]-5-phenyl-4(1H)-pyridone, NMR peaks at 222 and 488.5 CPS; aromatic protons at 414–463 CPS; yield 14%

EXAMPLE 226

1-methyl-3-(3-methylsulfonyloxyphenyl)-5-phenyl-4(1H)-pyridone, NMR peaks at 185 and 213 CPS; aromatic protons at 422–472 CPS; yield 20%

EXAMPLE 227

1-methyl-3-phenyl-5-[3-(1,1,2,2-tetrafluoroethoxy)-phenyl]-4(1H)-pyridone, m.p. 119°–121° C., yield 84%, made by using tetrafluoroethylene, in the presence of potassium hydroxide.

EXAMPLE 228

3-(3-acetoxyphenyl)-1-methyl-5-phenyl-4(1H)-pyridone, NMR peaks at 134 and 210 CPS; aromatic protons at 415–466 CPS; yield 28%, made by using acetic anhydride

EXAMPLE 229

3-(3-hexyloxyphenyl)-1-methyl-5-phenyl-4(1H)-pyridone, NMR peaks at 53, 214 and 239 CPS; a broad peak at 60–120 CPS; aromatic protons at 402–465 CPS; yield 55%

EXAMPLE 230

3-(3-decyloxyphenyl)-1-methyl-5-phenyl-4(1H)-pyridone, NMR peaks at 53, 211 and 239 CPS; a broad peak at 62–123 CPS; aromatic protons at 404–467 CPS; yield 24%

EXAMPLE 231

1-methyl-3-phenyl-5-(3-propoxyphenyl)-4(1H)-pyridone, NMR peaks at 54, 101.5, 208 and 232 CPS; aromatic protons at 400–463 CPS; yield 31%

EXAMPLE 232

1-methyl-3-phenyl-5-(3-propargyloxyphenyl)-4(1H)-pyridone, NMR peaks at 150 and 215 CPS; a broad peak at 280–285 CPS; aromatic protons at 430–470 CPS; yield 6%

EXAMPLE 233

3-(3-cyclohexylmethoxyphenyl)-1-methyl-5-phenyl-4(1H)-pyridone, NMR peaks at 214 and 226 CPS; a broad peak at 35–124 CPS; aromatic protons at 402–466 CPS; yield 16%

EXAMPLE 234

1-methyl-3-(3-octyloxyphenyl)-5-phenyl-4(1H)-pyridone, NMR peaks at 52, 218 and 239 CPS; a broad peak at 58–122 CPS; aromatic protons at 403–467 CPS; yield 19%

EXAMPLE 235

1-methyl-3-(3-phenoxyphenyl)-5-phenyl-4(1H)-pyridone, NMR peak at 214 CPS; aromatic protons at 410–470 CPS; yield 34%

The examples below illustrate the preparation of pyridinethiones.

EXAMPLE 236

3,5-diphenyl-1-methyl-4(1H)-pyridinethione

A 10 g. portion of 3,5-diphenyl-1-methyl-4(1H)-pyridone was made by the process of Example 2. A 10 g. portion of $P_2S_5$ was mixed with it in 100 ml. of pyridine, and the mixture was heated under reflux for 2 hours, after which it was poured into a large amount of water and stirred for one hour. The mixture was then filtered, and the solids were recrystallized from ethanol to yield 9.8 g. of 3,5-diphenyl-1-methyl-4(1H)-pyridinethione, m.p. 168°–171° C.

EXAMPLE 237

3,5-bis(3-chlorophenyl)-1-methyl-4(1H)-pyridinethione, m.p. 210°–212° C., yield 86%

EXAMPLE 238

3-(3-chlorophenyl)-1-methyl-5-phenyl-4(1H)-pyridinethione, m.p. 190°–193° C., yield 71%

EXAMPLE 239

1-methyl-3-phenyl-5-(3-trifluoromethylphenyl)-4(1H)-pyridinethione, m.p. 210° C., yield 70%

EXAMPLE 240

3-(3-bromophenyl)-1-methyl-5-phenyl-4(1H)-pyridinethione, m.p. 185°–188° C., yield 59%

EXAMPLE 241

1-methyl-3-(4-chlorophenyl)-5-(3-trifluoromethylphenyl)-4(1H)-pyridinethione, m.p. 239°–242° C., yield 25%

EXAMPLE 242

1-methyl-3-(3-methylphenyl)-5-(3-trifluoromethylphenyl)-4(1H)-pyridinethione, m.p. 193°–196° C., yield 50%

EXAMPLE 243

1-methyl-3-(2-methylphenyl)-5-(3-trifluoromethylphenyl)-4(1H)-pyridinethione, m.p. 193°–195° C., yield 35%

EXAMPLE 244

1-methyl-3-propyl-5-(3-trifluoromethylphenyl)-4(1H)-pyridinethione, m.p. 145°–148° C., yield 40%

EXAMPLE 245

1-methyl-3-phenoxy-5-(3-trifluoromethylphenyl)-4(1H)-pyridinethione, m.p. 127°–131° C., yield 40%

EXAMPLE 246

3-ethylthio-1-methyl-5-(3-trifluoromethylphenyl)-4(1H)-pyridinethione, m.p. 136°–138° C., yield 55%

EXAMPLE 247

3-ethoxy-1-methyl-5-(3-trifluoromethylphenyl)-4(1H)-pyridinethione, m.p. 153°–155° C., yield 5%

The following example illustrates the synthesis of compounds of the invention by the 4-chlorination of a 1-unsubstituted pyridone, followed by 1-alkylation and hydrolysis.

EXAMPLE 248

3,5-diphenyl-1-methyl-4(1H)-pyridone

A 30 g. portion of 3,5-diphenyl-4(1H)-pyridone, made by the method of Benary and Bitter, was refluxed with 100 ml. of $POCl_3$ and 5 ml. of dimethylformamide for three hours. The excess $POCl_3$ was then removed under vacuum, and the residue was taken up in chloroform. The solution was poured into ice-water and the mixture was stirred until the mixture reached room temperature. The aqueous mixture was then extracted with chloroform, and the organic solution was washed with dilute sodium hydroxide solution, and dried. The organic solution was then evaporated to dryness under vacuum, and the residue was recrystallized from hexane to produce 29 g. of 4-chloro-3,5-diphenylpyridine.

A 2 g. portion of the above compound was dissolved in 20 ml. of chloroform, and 10 ml. of methyl iodide was added. The mixture was allowed to stand for four days. The mixture was then evaporated to dryness, and the residue was recrystallized from chloroform-hexane to produce pure 4-chloro-3,5-diphenyl-1-methyl-pyridinium iodide, m.p. 200°–205° C. with decomposition.

A portion of the above intermediate product was dissolved in methanol, and the solution was made basic with aqueous sodium hydroxide solution. The basic mixture was then heated at reflux for one hour, cooled, and the solids were separated by filtration. The product was 3,5-diphenyl-1-methyl-4(1H)-pyridone, m.p. 187°–188° C.

The following compound was also made by the general process of Example 248.

EXAMPLE 249

1-ethyl-3-(3-methylphenyl)-5-phenyl-4(1H)-pyridone, m.p. 87°–89° C., yield 2%

The following example demonstrates a synthesis starting with a ketone, wherein the starting compound is first formylated, then aminoformylated, and finally exchanged with an amine to form the pyridone.

EXAMPLE 250

3,5-diphenyl-1-methyl-4(1H)-pyridone

A 12 g. portion of sodium methoxide was suspended in 150 ml. of ethyl ether. The suspension was chilled in an ice bath, and 21 g. of 1,3-diphenyl-2-propanone was added. A 14 g. portion of ethyl formate was then added dropwise to the stirred mixture. While the reaction mixture was stirred constantly, it was allowed to warm slowly to room temperature overnight. In the morning, the mixture was extracted with water, and the water layer was made acid with dilute hydrochloric acid and was extracted with methylene chloride. The organic layer was then extracted with dilute aqueous sodium hydroxide, and the water layer was made acid with dilute hydrochloric acid and was then extracted with methylene chloride. The organic extract was dried, and was evaporated to dryness under vacuum to produce 22 g. of oil which was predominantly 2,4-diphenyl-1-hydroxy-1-butene-3-one.

An 11 g. portion of the above intermediate product was heated on the steam bath with 20 ml. of dimethylformamide dimethyl acetal for 16 hours. The reaction mixture was then evaporated to dryness under vacuum, and the residue was taken up in 150 ml. of ethanol. Ten g. of methylamine hydrochloride and 20 ml. of 40% aqueous methylamine was added, and the mixture was stirred at reflux temperature overnight. The reaction mixture was then evaporated under vacuum to produce an oil. The oil was taken up in chloroform, and the solution was washed with water and dried over sodium sulfate. The solvent was then removed under vacuum, and the residue was triturated with ethyl ether. The ether was filtered to produce 5 g. of 3,5-diphenyl-1-methyl-4(1H)-pyridone, m.p. 187°–188° C.

The example next below shows the synthesis of a pyridone of this invention by the formylation of a ketone, followed by exchange with an amine and aminoformylation.

EXAMPLE 251

3,5-diphenyl-1-methyl-4(1H)-pyridone

The formylation of 1,3-diphenyl-2-propanone was carried out according to the method of Example 250. A 5 g. portion of the product was dissolved in 50 ml. of ethanol, and 20 ml. of 40% aqueous methylamine was added. The mixture was allowed to stand overnight at room temperature. The mixture was then evaporated to dryness under vacuum, leaving a heavy viscous oil. The oil was mixed with 10 ml. of dimethylformamide dimethyl acetal, and was heated on the steam bath overnight under a trap which removed ethanol as it was formed. The next day, the reaction mixture was evaporated to dryness under vacuum, and the residue was triturated with ether. The ether solution was filtered, and the solids were recrystallized from acetone-ethyl ether to produce 0.45 g. of 3,5-diphenyl-1-methyl-4(1H)-pyridone. The filtrate was retreated with methylamine to produce 0.4 g. of additional product, m.p. 187°–188° C.

The next example below shows the synthesis of a pyridone, starting from a ketone, by successive aminoformylation, formylation, and exchange with an amine.

EXAMPLE 252

3,5-diphenyl-1-methyl-4(1H)-pyridone

A 21 g. portion of 1,3-diphenyl-2-propanone was mixed with 12 g. of dimethylformamide dimethyl acetal, and heated on the steam bath under a trap which removed ethanol as it was formed. Heating was continued overnight, after which the reaction mixture was evaporated to produce 22 g. of an oil which was primarily 1-dimethylamino-2,4-diphenyl-1-buten-3-one.

A 5 g. portion of the above intermediate was formylated with ethyl formate in the presence of sodium methoxide according to the process of Example 250. The product of the formylation was dissolved in ethanol, and treated with 5 g. of methylamine hydrochloride and 20 ml. of 40% aqueous methylamine. The mixture was stirred overnight at reflux temperature, after which the solvent was removed under vacuum, 100 ml. of water was added to the residue and the mixture was extracted with ethyl ether. The ether solution was dried over sodium sulfate and evaporated to dryness to give 0.8 g. of 3,5-diphenyl-1-methyl-4(1H)-pyridone, m.p. 187°–188° C.

The following example illustrates the synthesis of a 1-unsubstituted pyridone by reaction of a ketone with a tris(formylamino)methane.

EXAMPLE 253

3,5-diphenyl-4(1H)-pyridone

A 1.4 g. portion of 1,3-diphenyl-2-propanone was mixed with 1.0 g. of tris(formylamino)methane in 20 ml. of dimethylformamide. The reaction mixture was stirred at reflux temperature for 3 hours. The mixture was then cooled to approximately room temperature, and poured into water. The precipitated solids were separated by filtration, and the solids were suspended in chloroform. The chloroform was then filtered, and the solids remaining were washed first with water, and then with chloroform. The yield was about 100 mg. of 3,5-diphenyl-4(1H)-pyridone, m.p. greater than 335° C.

The following example illustrates the 1-alkylation of a 1-unsubstituted pyridone by reaction with a methylating agent.

EXAMPLE 254

3,5-diphenyl-1-methyl-4(1H)-pyridone

A 6 g. portion of 3,5-diphenyl-4(1H)-pyridone was suspended in 30 ml. of chloroform, and 6 g. of methyl trifluoromethanesulfonate was added. The reaction mixture was stirred for 3 hours, 10 g. more of the sulfonate was added, and the mixture was stirred overnight. In the morning, the reaction mixture was poured into aqueous sodium carbonate solution. The aqueous mixture was filtered, and the precipitate was washed with additional chloroform. The organic layer of the filtrate was separated, dried over magnesium sulfate and evaporated to dryness. The residue was an oily gum which was identified by NMR analysis as essentially pure 3,5-diphenyl-1-methyl-4-methoxypyridine, trifluoromethanesulfonate.

The residue was mixed with 30 ml. of ethanol and 3 ml. of concentrated hydrochloric acid, and the mixture was stirred at reflux for 2 hours. The reaction mixture was then concentrated under vacuum to an oil, which was taken up in methylene chloride. The mixture was washed with aqueous sodium carbonate solution, and the organic layer was again evaporated to dryness under vacuum. The residue was triturated with ethyl acetate, leaving 0.15 g. of a precipitate, which was held and combined with the later-separated product. The ethyl acetate solution was concentrated under vacuum, the residue was mixed with 30 ml. of ethanol and 10 ml. of 10% sodium hydroxide solution, and the mixture was stirred at reflux temperature for 2 hours. The reaction mixture was then poured into water, the insoluble product was removed by filtration, and the solids were recrystallized from acetone. The product was 1.49 g. of 3,5-diphenyl-1-methyl-4(1H)-pyridone, m.p. 187°–188° C.

The following example illustrates the use of a formate ester aminal as an aminoformylating agent in the process.

EXAMPLE 255

1-methyl-3-phenyl-5-(3-trifluoromethylphenyl)-4(1H)-pyridone

A 15 g. portion of 1-phenyl-3-(3-trifluoromethylphenyl)-2-propanone was added to an ethyl ether solution, at ice bath temperature, of 70 g. of (t-butoxy)-di(-dimethylamino)methane. The mixture was warmed to evaporate the ether, and was then heated on the steam bath for 2 hours. The volatiles were then evaporated under vacuum, and the residue combined with 15 g. of methylamine hydrochloride, 40 ml. of 40% aqueous methylamine and 200 ml. of ethanol. The reaction mixture was then heated on the steam bath for 6 hours, and evaporated to dryness. The residue was taken up in water, and extracted with methylene chloride. The organic layer was washed with water, dried, and chromatographed on a silica gel column with ethyl acetate:-benzene. Collection and evaporation of the product-containing fractions gave about 0.9 g. of 1-methyl-3-phenyl-5-(3-trifluoromethylphenyl)-4(1H)-pyridone, m.p. 152°–156° C.

The next example shows the use of a formiminium halide for aminoformylating the starting propanone.

EXAMPLE 256

3,5-bis(3-chlorophenyl)-1-methyl-4(1H)-pyridone

The aminoformylating reagent was made by adding 30 g. of dimethylformamide dropwise to 20 g. of phosgene in 150 ml. of chloroform at 0° C. A 10 g. portion of 1,3-bis(3-chlorophenyl)-2-propanone in 50 ml. of chloroform was then added. The mixture was stirred for 3 hours, after which 50 ml. of 40% aqueous methylamine was added. Chloroform was then evaporated from the mixture, and 200 ml. of ethanol and 50 ml. of additional 40% aqueous methylamine were added. The mixture was then stirred under reflux overnight. In the morning, the product was extracted as described in the example above, and chromatographed on a silica gel column with ethyl acetate containing successively larger quantities of methanol. The product, 3,5-bis(3-chlorophenyl)-1-methyl-4(1H)-pyridone, 0.85 g., melted at 164°–167° C.

Continued elution of the column with methanol removed a compound identified by NMR as 4-chloro-3,5-bis(3-chlorophenyl)-1-methylpyridinium chloride. Hydrolysis of the compound with aqueous ethanolic sodium hydroxide solution at reflux temperature yielded additional pyridone upon dilution with water, filtration, and recrystallization from acetone-ethyl ether.

The compounds described above have been tested in a number of herbicidal test systems to determine the range of their herbicidal efficacy. The outstanding results produced by the compounds in the representative tests reported below are exemplary of the outstanding activity of the compounds.

Compound application rates are expressed in kilograms of the compound per hectare of land (kg./ha.) throughout this specification and claims.

Blank spaces in the tables below indicate that the compound was not tested against the named species. In some instances, the results of testing a compound repeatedly against a plant species have been averaged.

Untreated control plants or plots were included in all tests. Ratings of the control produced by the compounds were made by comparison of the treated plants or plots with the controls.

In the tests of Examples 257–261, plants were rated on a 1–5 scale, on which 1 indicates normal plants and 5 indicates dead plants or no emergence. A 0–10 rating scale, on which 0 indicates normal plants and 10 indicates dead plants or no emergence, was used in the tests of Examples 262–264 and 267–269, and the tests of Examples 265–266 and 271 were rated as percent control of the plants. Rating scales used in the tests of Example 270 are indicated in the description of the example.

EXAMPLE 257 broad spectrum greenhouse test

Square plastic pots were filled with a sterilized sandy loam soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test.

The table below reports results of testing typical compounds of the invention. The compounds are identified by their example numbers above.

Table 1

| Compound of Example No. | Preemergence | | | Postemergence | | |
|---|---|---|---|---|---|---|
| | Tomato | Large Crabgrass | Pigweed | Tomato | Large Crabgrass | Pigweed |
| 1 | 5 | 5 | 5 | 4 | 4 | 4 |
| 2 | 4 | 4 | 4 | 4 | 4 | 3 |
| 3 | 4 | 4 | 4 | 5 | 4 | 3 |
| 6 | 5 | 5 | 5 | 5 | 5 | 3 |
| 7 | 4 | 4 | 4 | 3 | 4 | 4 |
| 11 | 4 | 4 | 4 | 3 | 4 | 3 |
| 12 | 1 | 1 | 1 | 1 | 2 | 2 |
| 16 | 4 | 4 | 4 | 4 | 4 | 4 |
| 18 | 3 | 3 | 4 | 3 | 3 | 3 |
| 19 | 5 | 5 | 4 | 4 | 3 | 3 |
| 20 | 2 | 4 | 3 | 2 | 3 | 2 |
| 21 | 2 | 2 | 2 | 2 | 2 | 2 |
| 22 | 1 | 4 | 3 | 1 | 1 | 1 |
| 23 | 1 | 1 | 1 | 1 | 1 | 1 |
| 24 | 5 | 5 | 5 | 3 | 4 | 3 |
| 25 | 5 | 5 | 5 | 5 | 5 | 4 |
| 26 | 5 | 5 | 5 | 5 | 4 | 4 |
| 27 | 3 | 4 | 3 | 2 | 2 | 2 |
| 29 | 4 | 5 | 5 | 5 | 4 | 4 |
| 30 | 5 | 5 | 5 | 5 | 4 | 4 |
| 31 | 5 | 5 | 5 | 5 | 5 | 4 |
| 32 | 5 | 5 | 5 | 5 | 5 | 4 |
| 33 | 4 | 4 | 3 | 4 | 4 | 4 |
| 34 | 5 | 5 | 5 | 5 | 5 | 4 |
| 35 | 5 | 5 | 5 | 5 | 5 | 5 |
| 37 | 5 | 5 | 5 | 5 | 4 | 4 |
| 38 | 5 | 5 | 5 | 4 | 4 | 4 |
| 39 | 5 | 5 | 5 | 5 | 5 | 5 |
| 40 | 5 | 5 | 5 | 4 | 4 | 4 |
| 41 | 5 | 5 | 5 | 5 | 5 | 5 |
| 42 | 5 | 5 | 5 | 5 | 5 | 5 |
| 43 | 4 | 5 | 5 | 5 | 5 | 5 |
| 44 | 4 | 5 | 5 | 3 | 4 | 4 |
| 45 | 5 | 5 | 5 | 4 | 4 | 4 |
| 46 | 4 | 5 | 5 | 4 | 4 | 4 |
| 47 | 4 | 4 | 4 | 4 | 4 | 3 |
| 49 | 1 | 1 | 1 | 3 | 2 | 3 |
| 50 | 2 | 3 | 2 | 3 | 2 | 2 |
| 51 | 4 | 4 | 4 | 3 | 4 | 3 |
| 52 | 2 | 4 | 3 | 2 | 3 | 3 |
| 53 | 5 | 5 | 5 | 3 | 3 | 2 |
| 55 | 1 | 1 | 1 | 1 | 1 | 1 |
| 58 | 4 | 4 | 4 | 3 | 3 | 3 |
| 59 | 3 | 4 | 4 | 3 | 3 | 3 |
| 60 | 3 | 4 | 3 | 3 | 3 | 3 |
| 62 | 4 | 4 | 4 | 3 | 2 | 3 |
| 63 | 2 | 4 | 3 | 3 | 3 | 3 |
| 72 | 5 | 5 | 5 | 4 | 4 | 4 |
| 108 | 4 | 4 | 4 | 5 | 5 | 4 |
| 113 | 5 | 5 | 5 | 5 | 5 | 5 |
| 119 | 2 | 3 | 3 | 2 | 2 | 2 |
| 121 | 1 | 4 | 3 | 3 | 2 | 3 |
| 122 | 2 | 2 | 2 | 2 | 2 | 2 |
| 124 | 2 | 3 | 2 | 2 | 2 | 2 |
| 140 | 5 | 5 | 5 | 4 | 4 | 4 |
| 157 | 1 | 1 | 1 | 1 | 1 | 1 |
| 205 | 5 | 4 | 4 | 4 | 4 | 5 |
| 206 | 3 | 3 | 4 | 3 | 3 | 2 |
| 207 | 2 | 2 | 2 | 2 | 1 | 3 |
| 209 | 3 | 4 | 2 | 3 | 3 | 2 |
| 211 | 5 | 5 | 5 | 4 | 4 | 4 |
| 217 | 4 | 4 | 3 | 3 | 4 | 3 |
| 218 | 1 | 1 | 2 | 2 | 2 | 2 |
| 232 | 1 | 1 | 2 | 2 | 2 | 2 |
| 236 | 4 | 4 | 3 | 3 | 3 | 3 |
| 237 | 3 | 4 | 4 | 4 | 4 | 3 |
| 238 | 4 | 4 | 4 | 4 | 4 | 3 |
| 239 | 4 | 4 | 4 | 3 | 4 | 3 |

EXAMPLE 258 seven-species greenhouse test

The test was conducted in general like the test described in Example 257. In this test, the seeds were planted in flat metal trays, rather than in pots. The compounds were formulated according to the procedure above, except that about 6 g./100 ml. of the compound was dissolved in the surfactant-containing solvent, and about 1 part of the organic solution was diluted with 12 parts of water before application to the trays. The compounds were applied at the rate of 9.0 kg./ha., and the results of testing against the species named below were as follows.

Table 2

| Compound of Example No. | Preemergence | | | | | | | Postemergence | | | | | | |
|---|---|---|---|---|---|---|---|---|---|---|---|---|---|---|
| | Corn | Large Crab-grass | Pigweed | Foxtail | Vel-vet-leaf | Morning-glory | Zinnia | Corn | Large Crab-grass | Pigweed | Foxtail | Vel-vet-leaf | Morning-glory | Zinnia |
| 1 | 5 | 5 | 5 | 5 | 5 | 5 | 5 | 3 | 4 | 3 | 4 | 3 | 2 | 2 |
| 2 | 2 | 5 | 4 | 5 | 3 | 2 | 3 | 3 | 4 | 4 | 4 | 3 | 2 | |
| 3 | 4 | 5 | 5 | 5 | 5 | 3 | 3 | 3 | 3 | 3 | 2 | 3 | 2 | 3 |
| 4 | 1 | 5 | 1 | 1 | 2 | 3 | 2 | 1 | 1 | 1 | 1 | 1 | 1 | 1 |
| 5 | 3 | 5 | 5 | 5 | 5 | 5 | 5 | 2 | 3 | 3 | 2 | 2 | 3 | 2 |
| 6 | 3 | 5 | 5 | 5 | 5 | 5 | 4 | 2 | 3 | 3 | 3 | 3 | 2 | 2 |
| 7 | 5 | 5 | 5 | 5 | 5 | 5 | 5 | 3 | 2 | 2 | 3 | 3 | 2 | 2 |
| 8 | 5 | 5 | 5 | 5 | 5 | 5 | 5 | 3 | 4 | 3 | 4 | 4 | 3 | 3 |
| 9 | 4 | 5 | 5 | 5 | 5 | 5 | 5 | 3 | 3 | 2 | 3 | 3 | 3 | 2 |
| 10 | 3 | 5 | 5 | 5 | 5 | 5 | 4 | 3 | 3 | 2 | 2 | 2 | 2 | 2 |
| 11 | 4 | 5 | 5 | 5 | 5 | 4 | 3 | 4 | 3 | 3 | 3 | 3 | 2 | 3 |
| 12 | 1 | 2 | 2 | 2 | 2 | 1 | 1 | 2 | 2 | 2 | 3 | 1 | 1 | 1 |
| 13 | 5 | 5 | 5 | 5 | 5 | 5 | 5 | 4 | 4 | 3 | 4 | 3 | 3 | 3 |
| 14 | 5 | 5 | 5 | 5 | 5 | 5 | 5 | 4 | 4 | 2 | 4 | 3 | 3 | 3 |
| 15 | 4 | 5 | 5 | 5 | 5 | 5 | 5 | 3 | 2 | 2 | 2 | 1 | 2 | 2 |
| 16 | 3 | 5 | 5 | 5 | 5 | 5 | 5 | 2 | 2 | 2 | 2 | 2 | 2 | 2 |
| 17 | 3 | 5 | 5 | 4 | 4 | 3 | 2 | 2 | 1 | 2 | 2 | 2 | 2 | 2 |
| 18 | 1 | 4 | 4 | 2 | 2 | 1 | 1 | 1 | 1 | 1 | 1 | 1 | 1 | |
| 19 | 1 | 3 | 2 | 2 | 2 | 1 | 2 | 2 | 2 | 3 | 2 | 2 | 2 | 2 |
| 20 | 1 | 3 | 2 | 2 | 2 | 1 | 2 | 1 | 1 | 1 | 1 | 1 | 1 | 1 |
| 21 | 1 | 1 | 1 | 1 | 1 | 1 | 1 | 2 | 1 | 2 | 3 | 2 | 2 | 2 |
| 22 | 2 | 3 | 3 | 2 | 2 | 1 | 2 | 1 | 1 | 1 | 1 | 1 | 1 | 1 |
| 23 | 1 | 1 | 1 | 1 | 1 | 1 | 1 | 1 | 1 | 2 | 2 | 1 | 1 | 1 |
| 27 | 1 | 1 | 1 | 1 | 1 | 1 | 1 | 1 | 1 | 2 | 1 | 1 | 2 | 1 |
| 28 | 3 | 4 | 4 | 4 | 4 | 2 | 3 | 3 | 4 | 3 | 4 | 3 | 3 | 3 |
| 29 | 1 | 3 | 3 | 2 | 2 | 1 | 1 | 2 | 2 | 2 | 2 | 2 | 2 | 2 |
| 30 | 2 | 4 | 4 | 2 | 2 | 1 | 1 | 3 | 3 | 4 | 4 | 3 | 3 | 3 |
| 31 | 3 | 4 | 5 | 5 | 4 | 2 | 3 | 3 | 4 | 3 | 3 | 3 | 3 | 3 |
| 32 | 4 | 5 | 3 | 5 | 3 | 3 | 3 | 4 | 4 | 3 | 3 | 4 | 3 | 3 |
| 33 | 1 | 3 | 3 | 3 | 2 | 1 | 1 | 2 | 2 | 2 | 2 | 1 | 2 | 1 |
| 34 | 2 | 4 | 3 | 4 | 3 | 2 | 2 | 3 | 3 | 4 | 3 | 4 | 3 | 3 |
| 35 | 4 | 4 | 4 | 5 | 4 | 2 | 2 | 4 | 4 | 3 | 4 | 3 | 3 | 3 |
| 37 | 4 | 5 | 5 | 4 | 3 | 3 | 2 | 3 | 4 | 3 | 4 | 3 | 3 | 3 |
| 38 | 3 | 4 | 2 | 2 | 2 | 2 | 2 | 3 | 4 | 5 | 3 | 3 | 3 | 3 |
| 40 | 1 | 3 | 2 | 2 | 2 | 1 | 2 | 3 | 4 | 4 | 3 | 3 | 3 | 3 |
| 41 | 3 | 4 | 2 | 3 | 4 | 2 | 3 | 4 | 5 | 5 | 5 | 5 | 4 | 4 |
| 42 | 3 | 5 | 4 | 4 | 3 | 3 | 3 | 4 | 5 | 5 | 5 | 5 | 4 | 4 |
| 43 | 3 | 5 | 4 | 4 | 2 | 2 | 1 | 2 | 3 | 3 | 2 | 3 | 3 | 3 |
| 44 | 1 | 4 | 4 | 3 | 2 | 1 | 1 | 2 | 3 | 3 | 3 | 3 | 2 | 3 |
| 45 | 3 | 5 | 5 | 4 | 4 | 4 | 2 | 4 | 3 | 3 | 3 | 3 | 3 | 3 |
| 46 | 2 | 5 | 4 | 4 | 3 | 2 | 2 | 2 | 2 | 2 | 2 | 2 | 2 | 2 |
| 47 | 3 | 5 | 5 | 5 | 5 | 4 | 5 | 2 | 2 | 2 | 2 | 2 | 2 | 2 |
| 48 | 3 | 5 | 5 | 5 | 5 | 4 | 3 | 2 | 2 | 2 | 2 | 2 | 2 | 2 |
| 50 | 1 | 1 | 1 | 1 | 1 | 1 | 1 | 1 | 1 | 1 | 1 | 1 | 1 | 1 |
| 51 | 5 | 5 | 5 | 5 | 5 | 4 | 4 | 3 | 4 | 2 | 3 | 3 | 2 | 2 |
| 52 | 2 | 4 | 2 | 2 | 2 | 1 | 1 | 2 | 2 | 2 | 2 | 2 | 2 | 2 |
| 53 | 3 | 5 | 4 | 4 | 4 | 4 | 3 | 3 | 3 | 2 | 2 | 2 | 2 | 2 |
| 54 | 5 | 5 | 5 | 5 | 5 | 5 | 5 | 3 | 2 | 2 | 2 | 2 | 2 | |
| 55 | 1 | 1 | 1 | 1 | 1 | 1 | 1 | 1 | 1 | 1 | 2 | 1 | 2 | 1 |
| 56 | 2 | 5 | 4 | 4 | 4 | 3 | 3 | 3 | 4 | 4 | 4 | 3 | 3 | 3 |
| 57 | 2 | 3 | 3 | 3 | 2 | 2 | 1 | 1 | 1 | 1 | 1 | 1 | 1 | 1 |
| 58 | 1 | 5 | 3 | 4 | 3 | 2 | 2 | 3 | 3 | 3 | 3 | 3 | 3 | 2 |
| 59 | 3 | 4 | 4 | 4 | 3 | 3 | 2 | 4 | 3 | 3 | 3 | 3 | 2 | 2 |
| 60 | 2 | 3 | 2 | 3 | 3 | 2 | 2 | 1 | 2 | 2 | 2 | 2 | 2 | 2 |
| 61 | 3 | 3 | 4 | 3 | 2 | 3 | 2 | 3 | 2 | 2 | 2 | 2 | 2 | 2 |
| 62 | 1 | 2 | 2 | 2 | 2 | 2 | 2 | 2 | 2 | 2 | 2 | 2 | 2 | 2 |
| 63 | 2 | 5 | 5 | 4 | 5 | 4 | 5 | 2 | 2 | 2 | 2 | 2 | 2 | 2 |
| 64 | 5 | 5 | 5 | 5 | 5 | 4 | 5 | 3 | 3 | 2 | 3 | 3 | 3 | 3 |
| 65 | 5 | 5 | 5 | 5 | 5 | 4 | 5 | 3 | 3 | 3 | 3 | 3 | 3 | 3 |
| 66 | 5 | 5 | 5 | 5 | 5 | 5 | 5 | 4 | 4 | 3 | 3 | 3 | 3 | 3 |
| 67 | 1 | 1 | 1 | 1 | 1 | 1 | 1 | 2 | 1 | 2 | 1 | 2 | 2 | 1 |
| 68 | 5 | 5 | 5 | 5 | 5 | 5 | 5 | 4 | 4 | 4 | 3 | 3 | 3 | 3 |
| 69 | 3 | 5 | 4 | 4 | 5 | 2 | 5 | 2 | 2 | 2 | 2 | 2 | 2 | 2 |
| 70 | 1 | 1 | 1 | 1 | 1 | 1 | 1 | 1 | 1 | 1 | 1 | 1 | 1 | 1 |
| 71 | 3 | 5 | 4 | 4 | 3 | 3 | 3 | 2 | 2 | 2 | 2 | 2 | 2 | 2 |
| 73 | 4 | 5 | 4 | 5 | 4 | 4 | 5 | 3 | 3 | 2 | 3 | 2 | 2 | 2 |
| 74 | 3 | 5 | 4 | 5 | 4 | 2 | 2 | 2 | 2 | 2 | 2 | 1 | 2 | 2 |
| 75 | 2 | 4 | 2 | 4 | 3 | 2 | 2 | 2 | 2 | 2 | 2 | 2 | 2 | 2 |
| 76 | 4 | 4 | 4 | 4 | 4 | 2 | 3 | 2 | 2 | 2 | 2 | 1 | 2 | 2 |

Table 2-continued

| Compound of Example No. | Preemergence | | | | | | | Postemergence | | | | | |
|---|---|---|---|---|---|---|---|---|---|---|---|---|---|
| | Corn | Large Crab-grass | Pigweed | Foxtail | Vel-vet-leaf | Morning-glory | Zinnia | Corn | Large Crab-grass | Pigweed | Foxtail | Vel-vet-leaf | Morning-glory | Zinnia |
| 77 | 5 | 5 | 5 | 5 | 4 | 4 | 5 | 3 | 3 | 3 | 3 | 3 | 3 | 2 |
| 78 | 2 | 4 | 2 | 3 | 3 | 2 | 1 | 2 | 2 | 2 | 2 | 2 | 1 | 1 |
| 79 | 4 | 5 | 5 | 5 | 5 | 5 | 5 | 3 | 4 | 3 | 3 | 3 | 2 | 3 |
| 80 | 1 | 1 | 1 | 1 | 1 | 1 | 1 | 1 | 1 | 1 | 1 | 1 | 1 | 1 |
| 81 | 2 | 4 | 4 | 4 | 4 | 2 | 2 | 3 | 2 | 3 | 2 | 2 | 2 | 2 |
| 82 | 1 | 3 | 3 | 2 | 2 | 1 | 1 | 2 | 2 | 2 | 2 | 2 | 2 | 2 |
| 83 | 4 | 5 | 5 | 5 | 5 | 5 | 5 | 3 | 2 | 2 | 2 | 2 | 2 | 2 |
| 84 | 3 | 5 | 5 | 4 | 3 | 2 | 2 | 2 | 2 | 2 | 2 | 2 | 2 | 2 |
| 85 | 1 | 1 | 1 | 1 | 1 | 2 | 1 | 2 | 1 | 2 | 1 | 1 | 2 | 2 |
| 86 | 4 | 5 | 5 | 5 | 5 | 5 | 5 | 2 | 2 | 2 | 2 | 2 | 2 | 2 |
| 87 | 1 | 4 | 2 | 3 | 3 | 3 | 2 | 2 | 2 | 2 | 2 | 2 | 2 | 2 |
| 88 | 2 | 5 | 5 | 5 | 5 | 4 | 3 | 1 | 2 | 2 | 2 | 1 | 2 | 1 |
| 89 | 1 | 4 | 3 | 3 | 1 | 1 | 2 | 2 | 2 | 2 | 2 | 2 | 2 | 2 |
| 90 | 1 | 3 | 3 | 2 | 3 | 1 | 1 | 1 | 2 | 2 | 2 | 2 | 2 | 2 |
| 91 | 3 | 5 | 5 | 5 | 4 | 4 | 3 | 2 | 3 | 4 | 3 | 3 | 3 | 2 |
| 92 | 5 | 5 | 5 | 5 | 5 | 5 | 5 | 2 | 3 | 3 | 3 | 2 | 2 | 2 |
| 93 | | 5 | 5 | 5 | 4 | 4 | 3 | 2 | 2 | 3 | 2 | 2 | 2 | 2 |
| 94 | 2 | 5 | 5 | 3 | 3 | 3 | 2 | 2 | 2 | 3 | 2 | 2 | 2 | 2 |
| 95 | 3 | 5 | 1 | 5 | 3 | 3 | 3 | 3 | 3 | 3 | 3 | 2 | 2 | 2 |
| 96 | 4 | 5 | 5 | 5 | 5 | 4 | 5 | 2 | 3 | 2 | 2 | 2 | 2 | 2 |
| 97 | 4 | 5 | 5 | 4 | 5 | 2 | 4 | 3 | 3 | 3 | 3 | 2 | 2 | 2 |
| 98 | 3 | 5 | 4 | 5 | 5 | 3 | 2 | 2 | 2 | 2 | 2 | 2 | 2 | 2 |
| 99 | 5 | 5 | 5 | 5 | 5 | 5 | 5 | 2 | 2 | 2 | 2 | 2 | 2 | 2 |
| 100 | 5 | 5 | 5 | 5 | 5 | 5 | 5 | 3 | 3 | 3 | 2 | 2 | 2 | 2 |
| 101 | 5 | 5 | 5 | 5 | 5 | 5 | 5 | 3 | 3 | 3 | 3 | 3 | 3 | 3 |
| 102 | 3 | 5 | 5 | 5 | 5 | 5 | 5 | 2 | 2 | 2 | 2 | 2 | 2 | 2 |
| 103 | 5 | 5 | 5 | 5 | 5 | 5 | 5 | 3 | 3 | 3 | 2 | 2 | 2 | 2 |
| 104 | 5 | 5 | 5 | 5 | 5 | 5 | 5 | 3 | 3 | 4 | 3 | 3 | 2 | 2 |
| 105 | 2 | 5 | 5 | 4 | 4 | 3 | 4 | 2 | 2 | 2 | 2 | 2 | 2 | 2 |
| 106 | 3 | 5 | 5 | 4 | 3 | 1 | 2 | 2 | 2 | 3 | 2 | 2 | 2 | 2 |
| 107 | 2 | 3 | 3 | 2 | 3 | 3 | 2 | 2 | 2 | 2 | 2 | 2 | 2 | 2 |
| 108 | 5 | 5 | 5 | 5 | 5 | 5 | 5 | 3 | 3 | 2 | 3 | 2 | 3 | 2 |
| 109 | 1 | 4 | 5 | 3 | 3 | 4 | 3 | 2 | 3 | 4 | 2 | 2 | 2 | 2 |
| 110 | 5 | 5 | 5 | 5 | 5 | 5 | 5 | 3 | 4 | 4 | 3 | 3 | 3 | 3 |
| 111 | 5 | 5 | 5 | 5 | 5 | 5 | 5 | 4 | 3 | 3 | 3 | 2 | 3 | 3 |
| 112 | 3 | 5 | 5 | 5 | 5 | 4 | 4 | 2 | 2 | 2 | 2 | 1 | 2 | 2 |
| 113 | 5 | 5 | 5 | 5 | 5 | 5 | 5 | 4 | 4 | 3 | 4 | 3 | 3 | 3 |
| 114 | 2 | 5 | 5 | 3 | 4 | 3 | 1 | 2 | 2 | 2 | 2 | 2 | 2 | 2 |
| 115 | 3 | 5 | 5 | 5 | 5 | 4 | 5 | 2 | 4 | 3 | 3 | 2 | 2 | 2 |
| 116 | 5 | 5 | 5 | 5 | 5 | 5 | 5 | 4 | 4 | 3 | 3 | 3 | 3 | 3 |
| 117 | 3 | 5 | 4 | 4 | 5 | 4 | 3 | 2 | 3 | 3 | 3 | 2 | 2 | 2 |
| 118 | 5 | 5 | 5 | 5 | 5 | 5 | 5 | 3 | 4 | 3 | 4 | 3 | 3 | 3 |
| 119 | 1 | 3 | 2 | 2 | 2 | 1 | 1 | 1 | 1 | 1 | 1 | 1 | 1 | 1 |
| 120 | 1 | 1 | 1 | 1 | 1 | 1 | 1 | 1 | 1 | 1 | 1 | 1 | 1 | 1 |
| 121 | 2 | 4 | 3 | 2 | 2 | 1 | 2 | 2 | 2 | 2 | 2 | 2 | 2 | 2 |
| 122 | 1 | 3 | 3 | 2 | 2 | 2 | 1 | 1 | 1 | 1 | 1 | 1 | 1 | |
| 123 | 4 | 5 | 5 | 5 | 5 | 5 | 5 | 2 | 2 | 2 | 2 | 2 | 3 | 2 |
| 124 | 1 | 1 | 1 | 1 | 1 | 1 | 1 | 1 | 1 | 1 | 1 | 1 | 1 | 1 |
| 125 | 1 | 1 | 1 | 1 | 1 | 1 | 1 | 1 | 2 | 1 | 1 | 3 | 1 | 1 |
| 126 | 4 | 5 | 5 | 5 | 5 | 5 | 5 | 3 | 4 | 3 | 3 | 3 | 2 | 2 |
| 127 | 5 | 5 | 5 | 5 | 5 | 5 | 5 | 4 | 4 | 3 | 3 | 2 | 3 | 3 |
| 128 | 1 | 4 | 5 | 3 | 2 | 1 | 1 | 2 | 2 | 3 | 2 | 2 | 2 | 2 |
| 129 | 2 | 4 | 2 | 3 | 1 | 2 | 2 | 1 | 1 | 2 | 1 | 2 | 2 | 2 |
| 130 | 1 | 3 | 4 | 3 | 3 | 2 | 1 | 2 | 2 | 3 | 2 | 2 | 3 | 2 |
| 131 | 1 | 1 | 1 | 1 | 1 | 1 | 1 | 1 | 2 | 2 | 1 | 1 | 3 | 1 |
| 132 | 3 | 5 | 3 | 4 | 4 | 3 | 4 | 2 | 1 | 2 | 1 | 1 | 2 | 1 |
| 133 | 3 | 4 | 3 | 3 | 2 | 2 | 3 | 2 | 3 | 2 | 2 | 2 | 2 | 2 |
| 134 | 1 | 1 | 2 | 1 | 1 | 1 | 1 | 2 | 2 | 2 | 1 | 1 | 2 | 2 |
| 135 | 2 | 4 | 2 | 4 | 3 | 1 | 2 | 1 | 1 | 1 | 1 | 1 | 1 | 1 |
| 136 | 3 | 5 | 3 | 4 | 4 | 2 | 3 | 2 | 1 | 2 | 2 | 1 | 2 | 2 |
| 137 | 4 | 5 | 5 | 4 | 4 | 4 | 3 | 2 | 2 | 2 | 2 | 2 | 2 | 2 |
| 138 | 2 | 5 | 5 | 4 | 4 | 4 | 4 | 2 | 2 | 2 | 2 | 2 | 2 | 2 |
| 139 | 1 | 4 | 4 | 3 | 4 | 3 | 2 | 2 | 2 | 3 | 3 | 1 | 2 | 2 |
| 140 | 5 | 5 | 5 | 5 | 5 | 5 | 4 | 3 | 2 | 2 | 2 | 2 | 2 | 2 |
| 141 | 2 | 4 | 2 | 3 | 1 | 1 | 1 | 2 | 2 | 2 | 2 | 1 | 1 | 2 |
| 142 | 4 | 5 | 3 | 5 | 5 | 2 | 2 | 2 | 2 | 2 | 2 | 2 | 2 | 2 |
| 143 | 2 | 4 | 2 | 3 | 2 | 1 | 1 | 2 | 3 | 3 | 2 | 3 | 2 | 2 |
| 144 | 1 | 4 | 2 | 2 | 2 | 1 | 1 | 1 | 1 | 2 | 1 | 1 | 1 | 2 |
| 145 | 1 | 4 | 1 | 2 | 1 | 1 | 1 | 1 | 1 | 2 | 1 | 1 | 1 | 1 |
| 146 | 5 | 5 | 5 | 5 | 5 | 5 | 5 | 3 | 2 | 2 | 2 | 2 | 2 | 2 |
| 147 | 4 | 5 | 5 | 5 | 5 | 2 | 4 | 3 | 2 | 2 | 2 | 2 | 2 | 2 |
| 148 | 3 | 5 | 5 | 4 | 4 | 3 | 2 | 1 | 2 | 2 | 2 | 1 | 2 | 2 |
| 149 | 3 | 5 | 5 | 4 | 3 | 2 | 2 | 2 | 3 | 3 | 2 | 2 | 2 | 2 |
| 150 | 3 | 5 | 5 | 4 | 4 | 3 | 4 | 3 | 3 | 2 | 2 | 2 | 2 | 3 |
| 151 | 4 | 4 | 4 | 4 | 4 | 4 | 4 | 1 | 1 | 2 | 1 | 2 | 2 | 2 |
| 152 | 4 | 5 | 5 | 5 | 5 | 5 | 5 | 3 | 2 | 2 | 2 | 2 | 2 | 2 |
| 153 | 3 | 4 | 4 | 3 | 4 | 2 | 2 | 1 | 1 | 1 | 1 | 1 | 1 | 1 |
| 154 | 5 | 5 | 5 | 5 | 5 | 5 | 5 | 2 | 2 | 2 | 2 | 2 | 2 | 2 |

Table 2-continued

| Compound of Example No. | Preemergence | | | | | | | Postemergence | | | | | | |
|---|---|---|---|---|---|---|---|---|---|---|---|---|---|---|
| | Corn | Large Crab-grass | Pigweed | Foxtail | Vel-vet-leaf | Morning-glory | Zinnia | Corn | Large Crab-grass | Pigweed | Foxtail | Vel-vet-leaf | Morning-glory | Zinnia |
| 155 | 4 | 5 | 4 | 5 | 5 | 4 | 4 | 2 | 1 | 1 | 2 | 1 | 2 | 2 |
| 156 | 2 | 3 | 3 | 2 | 3 | 1 | 1 | 2 | 1 | 1 | 1 | 1 | 1 | 1 |
| 158 | 1 | 1 | 1 | 1 | 1 | 1 | 1 | 1 | 1 | 1 | 1 | 1 | 1 | 1 |
| 159 | 2 | 4 | 3 | 2 | 2 | 1 | 2 | 2 | 2 | 2 | 2 | 1 | 2 | 2 |
| 160 | 4 | 5 | 5 | 5 | 4 | 4 | 4 | 3 | 2 | 2 | 3 | 2 | 2 | 3 |
| 161 | 3 | 5 | 3 | 4 | 2 | 1 | 1 | 3 | 2 | 2 | 2 | 2 | 2 | 2 |
| 162 | 5 | 5 | 4 | 5 | 4 | 5 | 5 | 2 | 2 | 2 | 2 | 1 | 2 | 2 |
| 163 | 3 | 5 | 5 | 4 | 4 | 2 | 2 | 2 | 2 | 2 | 2 | 2 | 2 | 2 |
| 164 | 5 | 5 | 5 | 5 | 5 | 5 | 5 | 4 | 4 | 4 | 3 | 3 | 3 | 3 |
| 165 | 1 | 3 | 4 | 2 | 3 | 2 | 1 | 1 | 1 | 2 | 1 | 1 | 3 | 1 |
| 166 | 2 | 4 | 3 | 3 | 4 | 3 | 2 | 2 | 2 | 2 | 2 | 1 | 2 | 2 |
| 167 | 2 | 5 | 4 | 2 | 3 | 1 | 1 | 2 | 2 | 2 | 1 | 1 | 2 | 1 |
| 168 | 3 | 5 | 5 | 4 | 4 | 4 | 4 | 3 | 3 | 3 | 3 | 3 | 2 | 2 |
| 169 | 4 | 5 | 5 | 5 | 5 | 5 | 5 | 3 | 3 | 3 | 3 | 2 | 2 | 3 |
| 170 | 2 | 5 | 5 | 4 | 3 | 2 | 2 | 2 | 2 | 3 | 2 | 3 | 2 | 2 |
| 171 | 5 | 5 | 4 | 5 | 5 | 5 | 5 | 3 | 3 | 2 | 3 | 2 | 2 | 2 |
| 172 | 5 | 5 | 5 | 5 | 5 | 5 | 5 | 3 | 4 | 3 | 3 | 2 | 2 | 2 |
| 173 | 3 | 5 | 5 | 5 | 4 | 5 | 5 | 2 | 3 | 3 | 3 | 2 | 2 | 2 |
| 174 | 4 | 5 | 5 | 5 | 5 | 5 | 5 | 3 | 3 | 3 | 3 | 2 | 2 | 2 |
| 175 | 4 | 5 | 5 | 5 | 5 | 5 | 5 | 4 | 3 | 3 | 3 | 2 | 2 | 2 |
| 176 | 3 | 5 | 5 | 5 | 5 | 5 | 5 | 3 | 3 | 3 | 3 | 2 | 2 | 2 |
| 177 | 3 | 5 | 5 | 5 | 5 | 5 | 5 | 2 | 3 | 2 | 3 | 2 | 2 | 2 |
| 178 | 3 | 3 | 2 | 3 | 3 | 2 | 2 | 1 | 1 | 1 | 1 | 1 | 1 | 1 |
| 179 | 5 | 5 | 5 | 5 | 5 | 5 | 5 | 3 | 4 | 3 | 3 | 3 | 2 | 2 |
| 180 | 3 | 5 | 5 | 5 | 4 | 4 | 3 | 1 | 2 | 2 | 2 | 2 | 2 | 2 |
| 181 | 4 | 5 | 5 | 5 | 5 | 5 | 5 | 2 | 2 | 3 | 2 | 3 | 2 | 2 |
| 182 | 4 | 5 | 5 | 5 | 4 | 2 | 2 | 2 | 3 | 3 | 2 | 3 | 2 | 2 |
| 183 | 4 | 5 | 5 | 5 | 5 | 4 | 4 | 2 | 3 | 2 | 3 | 3 | 2 | 2 |
| 184 | 2 | 3 | 4 | 3 | 3 | 2 | 1 | 1 | 2 | 2 | 1 | 1 | 2 | 1 |
| 185 | | | | | | | | 3 | 4 | 3 | 3 | 2 | 2 | 2 |
| 187 | 4 | 5 | 5 | 5 | 5 | 1 | 1 | 3 | 3 | 2 | 3 | 2 | 2 | 2 |
| 188 | 2 | 5 | 5 | 5 | 5 | 1 | 3 | 2 | 2 | 2 | 2 | 2 | 2 | 2 |
| 189 | 3 | 5 | 5 | 5 | 4 | 4 | 3 | 2 | 2 | 2 | 2 | 2 | 2 | 2 |
| 190 | 2 | 3 | 3 | 3 | 2 | 1 | 1 | 2 | 2 | 2 | 2 | 2 | 2 | 2 |
| 191 | 4 | 5 | 5 | 5 | 5 | 3 | 3 | 3 | 3 | 3 | 3 | 3 | 2 | 3 |
| 192 | 3 | 5 | 5 | 5 | 4 | 2 | 2 | 2 | 2 | 3 | 2 | 2 | 2 | 2 |
| 193 | 4 | 5 | 5 | 5 | 5 | 5 | 5 | 3 | 3 | 3 | 3 | 2 | 2 | 3 |
| 194 | 3 | 5 | 5 | 4 | 3 | 2 | 2 | 2 | 2 | 2 | 2 | 2 | 2 | 2 |
| 195 | 4 | 5 | 5 | 4 | 5 | 3 | 3 | 2 | 3 | 3 | 2 | 2 | 2 | 2 |
| 196 | 1 | 5 | 5 | 5 | 5 | 1 | 2 | 2 | 2 | 2 | 2 | 2 | 2 | 2 |
| 197 | 3 | 5 | 5 | 5 | 5 | 4 | 4 | 3 | 3 | 3 | 3 | 3 | 3 | 2 |
| 198 | 3 | 5 | 5 | 5 | 5 | 4 | 2 | 1 | 2 | 2 | 2 | 2 | 2 | 3 |
| 199 | 3 | | 5 | 5 | 3 | 4 | 3 | 2 | 2 | 2 | 2 | 2 | 2 | 2 |
| 200 | 1 | 4 | 5 | 4 | 2 | 1 | 1 | 2 | | 2 | 2 | 2 | 3 | 2 |
| 201 | 2 | 4 | 4 | 4 | 3 | 2 | 1 | 2 | | 2 | 2 | 3 | 2 | 2 |
| 202 | 4 | 5 | 5 | 5 | 4 | 3 | 2 | 3 | | 2 | 3 | 3 | 2 | 2 |
| 203 | 4 | 5 | 5 | 5 | 5 | 5 | 5 | 3 | 3 | 3 | 3 | 3 | 2 | 2 |
| 204 | 3 | 5 | 5 | 5 | 5 | 5 | 5 | 3 | 3 | 2 | 3 | 2 | 2 | 2 |
| 205 | 4 | 5 | 5 | 5 | 4 | 5 | 5 | 2 | 2 | 2 | 3 | 2 | 2 | 2 |
| 207 | 2 | 2 | 1 | 2 | 2 | 1 | 1 | 1 | 1 | 1 | 1 | 1 | 1 | 1 |
| 208 | 3 | 5 | 5 | 4 | 5 | 1 | 2 | 2 | 2 | 2 | 2 | 2 | 2 | 2 |
| 209 | 2 | 4 | 2 | 2 | 1 | 1 | 1 | 1 | 1 | 1 | 1 | 1 | 1 | 1 |
| 210 | 4 | 5 | 5 | 5 | 5 | 4 | 3 | 4 | 4 | 3 | 3 | 3 | 3 | 3 |
| 211 | 3 | 4 | 2 | 2 | 3 | 2 | 2 | 2 | 2 | 2 | 2 | 2 | 2 | 2 |
| 212 | 5 | 5 | 5 | 5 | 5 | 5 | 5 | 3 | 3 | 3 | 3 | 2 | 2 | 2 |
| 213 | 4 | 5 | 5 | 5 | 5 | 5 | 5 | 3 | 3 | 3 | 2 | 2 | 2 | 2 |
| 214 | 2 | 4 | 4 | 4 | 3 | 2 | 3 | 1 | 1 | 2 | 1 | 1 | 1 | 1 |
| 215 | 1 | 3 | 4 | 3 | 5 | 4 | 5 | 2 | 2 | 4 | 2 | 4 | 3 | 3 |
| 216 | 5 | 5 | 5 | 5 | 5 | 5 | 5 | 3 | 3 | 3 | 3 | 3 | 3 | 3 |
| 217 | 2 | 5 | 5 | 3 | 4 | 2 | 4 | 2 | 2 | 2 | 2 | 2 | 1 | 1 |
| 218 | 1 | 1 | 1 | 1 | 1 | 1 | 1 | 1 | 1 | 1 | 1 | 1 | 1 | 1 |
| 219 | 4 | 5 | 4 | 5 | 5 | 4 | 4 | 3 | 3 | 3 | 3 | 3 | 3 | 3 |
| 220 | 5 | 5 | 5 | 5 | 5 | 5 | 5 | 3 | 2 | 2 | 2 | 2 | 3 | 2 |
| 221 | 3 | 5 | 5 | 4 | 4 | 4 | 3 | 3 | 2 | 2 | 3 | 3 | 3 | 3 |
| 222 | 5 | 5 | 5 | 5 | 5 | 5 | 5 | 4 | 4 | 3 | 3 | 2 | 4 | 3 |
| 223 | 4 | 5 | 4 | 4 | 5 | 3 | 4 | 3 | 3 | 3 | 2 | 2 | 2 | 2 |
| 224 | 1 | 1 | 4 | 1 | 1 | 1 | 1 | 2 | 2 | 3 | 2 | 1 | 2 | 2 |
| 225 | 2 | 4 | 4 | 3 | 4 | 2 | 2 | 2 | 2 | 3 | 2 | 2 | 2 | 2 |
| 226 | 5 | 4 | 5 | 4 | 4 | 3 | 2 | 2 | 2 | 2 | 2 | 2 | 2 | 2 |
| 227 | 5 | 5 | 5 | 5 | 5 | 5 | 5 | 4 | 4 | 3 | 3 | 3 | 2 | 2 |
| 228 | 1 | 3 | 2 | 2 | 2 | 2 | 4 | 2 | 2 | 2 | 1 | 1 | 1 | 1 |
| 229 | 1 | 5 | 5 | 3 | 2 | 1 | 1 | 2 | 3 | 3 | 2 | 2 | 2 | 2 |
| 230 | 1 | 2 | 3 | 1 | 1 | 2 | 2 | 2 | 2 | 2 | 2 | 2 | 2 | 2 |
| 231 | 4 | 5 | 5 | 4 | 5 | 3 | 4 | 3 | 2 | 2 | 3 | 2 | 3 | 1 |
| 232 | 1 | 1 | 1 | 1 | 1 | 1 | 1 | 1 | 1 | 1 | 1 | 1 | 1 | 1 |
| 233 | 1 | 1 | 1 | 1 | 1 | 1 | 1 | 2 | 2 | 2 | 2 | 2 | 2 | 2 |
| 234 | 1 | 1 | 1 | 1 | 1 | 1 | 1 | 2 | 2 | 2 | 2 | 2 | 2 | 2 |
| 235 | 4 | 5 | 5 | 5 | 5 | 3 | 4 | 3 | 4 | 3 | 3 | 3 | 2 | 3 |

Table 2-continued

| | Preemergence | | | | | | | Postemergence | | | | | | |
|---|---|---|---|---|---|---|---|---|---|---|---|---|---|---|
| Compound of Example No. | Corn | Large Crab-grass | Pigweed | Foxtail | Vel-vet-leaf | Morning-glory | Zinnia | Corn | Large Crab-grass | Pigweed | Foxtail | Vel-vet-leaf | Morning-glory | Zinnia |
| 236 | 1 | 2 | 2 | 2 | 1 | 1 | 1 | 2 | 2 | 2 | 2 | 2 | 3 | 2 |
| 237 | 4 | 5 | 5 | 5 | 4 | 4 | 4 | 2 | 2 | 2 | 2 | 2 | 2 | 2 |
| 238 | 4 | 5 | 5 | 5 | 5 | 4 | 4 | 2 | 2 | 2 | 2 | 2 | 2 | 2 |
| 239 | 3 | 5 | 3 | 5 | 3 | 3 | 2 | 3 | 4 | 3 | 3 | 3 | 2 | 2 |
| 240 | 4 | 5 | 5 | 5 | 4 | 4 | 4 | 2 | 3 | 3 | 2 | 2 | 2 | 2 |
| 241 | 3 | 4 | 4 | 4 | 2 | 1 | 1 | 2 | 2 | 2 | 2 | 2 | 2 | 2 |
| 242 | 3 | 5 | 5 | 5 | 3 | 3 | 2 | 2 | 2 | 2 | 2 | 1 | 2 | 2 |
| 243 | 4 | 5 | 5 | 5 | 5 | 4 | 3 | 3 | 3 | 2 | 2 | 3 | 2 | 2 |
| 244 | 5 | 5 | 5 | 5 | 5 | 5 | 5 | 4 | 4 | 3 | 3 | 3 | 3 | 3 |
| 245 | 4 | 5 | 5 | 4 | 5 | 5 | 4 | 3 | 2 | 3 | 2 | 1 | 2 | 2 |
| 246 | 3 | 5 | 5 | 4 | 4 | 4 | 4 | 2 | 3 | 3 | 2 | 2 | 3 | 2 |
| 247 | 3 | 5 | 2 | 4 | 2 | 3 | 2 | 2 | 2 | 3 | 1 | 2 | 3 | 2 |
| 249 | 4 | 5 | 5 | 5 | 5 | 4 | 3 | 3 | 3 | 2 | 2 | 2 | 2 | 2 |

EXAMPLE 259 multiple-species greenhouse test

In general, the test method was the same as the method of the test above. Various compounds were tested preemergence and postemergence at different application rates which are indicated in the tables below. A number of additional weed and crop species were used in the preemergence tests as is shown in the table. Typical results were as follows.

Table 3

| | | Preemergence | | | | | | | | | |
|---|---|---|---|---|---|---|---|---|---|---|---|
| Compound of Example No. | Rate of Appln. kg./ha. | Corn | Cot-ton | Soy-bean | Wheat | Al-fal-fa | Su-gar Beet | Rice | Cu-cum-ber | To-ma-to | Barn-yard Grass |
| 1 | 1.1 | 4 | 1 | 4 | 3 | 2 | 5 | 2 | 4 | 4 | 4 |
| 2 | 2.2 | 3 | 1 | 2 | 2 | 2 | 4 | 2 | 2 | 3 | 3 |
| 3 | 0.14 | 2 | 1 | 1 | 3 | 3 | 3 | 1 | 1 | 3 | 4 |
| 3 | 1.1 | 4 | 1 | 3 | 4 | 4 | 4 | 2 | 4 | 4 | 4 |
| 4 | 1.1 | 1 | 1 | 1 | 1 | 1 | 1 | 1 | 1 | 1 | 1 |
| 5 | 0.28 | 3 | 1 | 2 | 3 | 3 | 4 | 2 | 2 | 3 | 4 |
| 6 | 0.14 | 1 | 1 | 1 | 1 | 2 | 2 | 1 | 1 | 2 | 3 |
| 7 | 0.035 | 2 | 1 | 2 | 3 | 2 | 3 | 1 | 2 | 3 | 3 |
| 8 | 1.1 | 4 | 2 | 4 | 4 | 5 | 5 | 2 | 4 | 5 | 5 |
| 9 | 0.56 | 4 | 1 | 4 | 3 | 5 | 5 | 2 | 5 | 5 | 5 |
| 10 | 0.28 | 3 | 1 | 2 | 2 | 3 | 4 | 2 | 2 | 3 | 4 |
| 11 | 0.56 | 3 | 1 | 2 | 3 | 2 | 2 | 2 | 2 | 3 | 4 |
| 13 | 0.14 | 2 | 1 | 3 | 3 | 3 | 4 | 1 | 2 | 2 | 3 |
| 13 | 1.1 | 5 | 3 | 4 | 5 | 5 | 5 | 3 | 5 | 5 | 5 |
| 14 | 0.035 | 2 | 1 | 2 | 3 | 3 | 4 | 1 | 2 | 3 | 3 |
| 14 | 4.5 | 2 | 4 | 5 | 5 | 5 | 4 | 5 | 5 | 5 | 5 |
| 15 | 0.018 | 2 | 1 | 2 | 2 | 2 | 4 | 1 | 2 | 3 | 3 |
| 16 | 0.28 | 1 | 1 | 1 | 2 | 2 | 3 | 1 | 1 | 3 | 3 |
| 18 | 1.1 | 2 | 1 | 2 | 2 | 4 | 4 | 2 | 2 | 2 | 2 |
| 25 | 0.56 | 2 | 1 | 3 | 2 | 4 | 3 | 1 | 2 | 3 | 2 |
| 26 | 2.2 | 1 | 1 | 1 | 1 | 2 | 2 | 1 | | 2 | 2 |
| 28 | 2.2 | 4 | 1 | 4 | 3 | 3 | 4 | 2 | 2 | 4 | 3 |
| 30 | 2.2 | 1 | 1 | 1 | 2 | 1 | 1 | 1 | 1 | 1 | 1 |
| 31 | 1.1 | 2 | 1 | 1 | 2 | 2 | 3 | 2 | 2 | 3 | 3 |
| 32 | 1.1 | 3 | 1 | 3 | 3 | 3 | 4 | 2 | 2 | 3 | 4 |
| 34 | 1.1 | 1 | 1 | 2 | 2 | 2 | 3 | 1 | 2 | 2 | 1 |
| 35 | 2.2 | 2 | 1 | 2 | 2 | 2 | 2 | 1 | 2 | 3 | 3 |
| 37 | 2.2 | 4 | 1 | 3 | 3 | 2 | 4 | 2 | 3 | 2 | 4 |
| 41 | 1.1 | 4 | 2 | 4 | 3 | 5 | 5 | 3 | 5 | 5 | 5 |
| 42 | 1.1 | 4 | 2 | 4 | 4 | 5 | 5 | 3 | 5 | 5 | 5 |
| 43 | 0.56 | 2 | 1 | 1 | 3 | 2 | 3 | 1 | 2 | 2 | 3 |
| 44 | 0.14 | 2 | 1 | 1 | 2 | 3 | 2 | 1 | 1 | 2 | 3 |
| 45 | 0.14 | 3 | 1 | 2 | 3 | 4 | 5 | 2 | 1 | 4 | 5 |
| 46 | 2.2 | 3 | 1 | 3 | 3 | 3 | 5 | 1 | 2 | 2 | 3 |
| 47 | 0.07 | 2 | 1 | 2 | 2 | 3 | 4 | 1 | 2 | 2 | 4 |
| 48 | 2.2 | 1 | 1 | 1 | 2 | 4 | 4 | 1 | 1 | 2 | 2 |
| 51 | 0.14 | 3 | 1 | 2 | 3 | 2 | 4 | 1 | 2 | 4 | 5 |
| 53 | 2.2 | 2 | 1 | 1 | 2 | 1 | 1 | 1 | 1 | 1 | 2 |
| 54 | 0.28 | 3 | 2 | 3 | 2 | 3 | 4 | 2 | 2 | 4 | 4 |
| 58 | 0.56 | 1 | 1 | 2 | 2 | 3 | 3 | 1 | 2 | 1 | 1 |
| 59 | 0.56 | 2 | 1 | 2 | 3 | 3 | 4 | 1 | 2 | 2 | 3 |
| 63 | 2.2 | 1 | 1 | 3 | 3 | 3 | 3 | 1 | 3 | 2 | 2 |
| 64 | 0.07 | 2 | 1 | 3 | 3 | 3 | 3 | 1 | 2 | 2 | 3 |
| 65 | 0.14 | 3 | 1 | 4 | 4 | 5 | 5 | 2 | 5 | 4 | 5 |
| 66 | 0.07 | 2 | 1 | 3 | 4 | 5 | 4 | 2 | 3 | 3 | 4 |
| 68 | 1.1 | 5 | 1 | 4 | 5 | 5 | 5 | 2 | 4 | 4 | 5 |
| 69 | 4.5 | 2 | 1 | 2 | 2 | 1 | 3 | 2 | 1 | 1 | 1 |
| 108 | 0.14 | 3 | 1 | 4 | 4 | 3 | 2 | 2 | 4 | 4 | 4 |
| 109 | 1.1 | 1 | 1 | 2 | 2 | 2 | 2 | 1 | 2 | 1 | 1 |
| 110 | 0.28 | 1 | 1 | 2 | 2 | 2 | 2 | 1 | 2 | 1 | 1 |

Table 3-continued

| | | | | | | | | | | | |
|---|---|---|---|---|---|---|---|---|---|---|---|
| 111 | 0.018 | 2 | 1 | 1 | 3 | 2 | 1 | 2 | 2 | 2 | 4 |
| 113 | 0.56 | 4 | 1 | 4 | 5 | 5 | 5 | 3 | 4 | 5 | 5 |
| 114 | 1.1 | 1 | 1 | 1 | 1 | 2 | 2 | 1 | 1 | 1 | 2 |
| 115 | 1.1 | 2 | 1 | 2 | 4 | 4 | 4 | 1 | 1 | 2 | 4 |
| 116 | 0.14 | 4 | 2 | 2 | 3 | 3 | 5 | 2 | 3 | 4 | 3 |
| 118 | 1.1 | 5 | 2 | 4 | 5 | 5 | 4 | 5 | 5 | 5 | 5 |
| 123 | 0.28 | 3 | 1 | 3 | 3 | 4 | 4 | 1 | 4 | 3 | 4 |
| 186 | 2.2 | 4 | 1 | 1 | 3 | 4 | 5 | 2 | 2 | 3 | 4 |
| 204 | 0.56 | 1 | 1 | 2 | 2 | 2 | 3 | 1 | 2 | 2 | 3 |
| 205 | 1.1 | 1 | 1 | 2 | 1 | 2 | 4 | 2 | 2 | 2 | 4 |
| 208 | 0.56 | 1 | 1 | 2 | 1 | 4 | 4 | 1 | 2 | 2 | 3 |
| 217 | 2.2 | 1 | 1 | 1 | 1 | 2 | 3 | 1 | 1 | 2 | 2 |
| 219 | 0.14 | 1 | 1 | 3 | 4 | 4 | 4 | 1 | 1 | 2 | 4 |
| 220 | 0.56 | 3 | 1 | 3 | 5 | 5 | 5 | 1 | 3 | 5 | 5 |
| 221 | 0.28 | 2 | 1 | 2 | 2 | 4 | 4 | 2 | 2 | 2 | 4 |
| 222 | 1.1 | 4 | 2 | 4 | 4 | 5 | 5 | 3 | 5 | 5 | 5 |
| 225 | 1.1 | 1 | 1 | 1 | 2 | 2 | 2 | 1 | 1 | 2 | 2 |
| 226 | 1.1 | 2 | 1 | 2 | 2 | 4 | 4 | 1 | 2 | 3 | 2 |
| 227 | 1.1 | 4 | 1 | 4 | 4 | 5 | 5 | 3 | 5 | 5 | 4 |
| 229 | 4.5 | 1 | 1 | 1 | 1 | 2 | 4 | 3 | 1 | 2 | 1 | 3 |
| 231 | 0.14 | 2 | 1 | 2 | 4 | 4 | 5 | 1 | 2 | 2 | 3 |
| 237 | 0.14 | 1 | 1 | 1 | 2 | 3 | 3 | 1 | 1 | 2 | 3 |
| 238 | 0.56 | 1 | 1 | 2 | 2 | 3 | 4 | 1 | 1 | 2 | 2 |
| 239 | 0.28 | 2 | 1 | 2 | 2 | 2 | 4 | 1 | 2 | 2 | 4 |

| Compound of Example No. | Rate of Appln. kg./ha. | Preemergence | | | | | | | | |
|---|---|---|---|---|---|---|---|---|---|---|
| | | Lambs-quarter | Large Crabgrass | Mustard | Pigweed | Foxtail | Wild Oat | Velvetleaf | Jimsonweed | Morning-glory | Zinnia |
| 1 | 1.1 | 5 | 5 | 3 | 5 | 5 | 4 | 5 | 4 | 5 | 3 |
| 2 | 2.2 | 3 | 4 | 2 | 3 | 4 | 2 | 3 | 2 | 2 | 1 |
| 3 | 0.14 | 4 | 4 | 5 | 4 | 4 | 2 | 2 | 3 | 2 | 2 |
| 3 | 1.1 | 4 | 5 | 5 | 5 | 4 | 4 | 4 | 4 | 4 | 4 |
| 4 | 1.1 | 1 | 1 | 1 | 1 | 1 | 1 | 1 | 1 | 1 | 1 |
| 5 | 0.28 | 4 | 5 | 5 | 4 | 4 | 2 | 5 | 3 | 5 | 4 |
| 6 | 0.14 | 4 | 5 | 3 | 5 | 3 | 2 | 2 | 2 | 1 | 2 |
| 7 | 0.035 | 4 | 5 | 5 | 4 | 4 | 2 | 2 | 2 | 2 | 2 |
| 8 | 1.1 | 4 | 5 | 5 | 5 | 5 | 4 | 5 | 4 | 4 | 5 |
| 9 | 0.56 | 5 | 5 | 3 | 4 | 4 | 5 | 5 | 3 | 4 | 4 |
| 10 | 0.28 | 4 | 4 | 3 | 4 | 4 | 2 | 2 | 3 | 3 | 2 |
| 11 | 0.56 | 4 | 5 | 3 | 4 | 3 | 3 | 3 | 3 | 2 | 2 |
| 13 | 0.14 | 3 | 5 | 2 | 5 | 3 | 2 | 2 | 2 | 4 | 2 |
| 13 | 1.1 | 5 | 5 | 5 | 5 | 5 | 5 | 5 | 5 | 5 | 5 |
| 14 | 0.035 | 3 | 4 | 4 | 4 | 4 | 2 | 2 | 3 | 3 | 3 |
| 14 | 4.5 | 5 | 5 | 5 | 4 | 5 | 4 | 4 | 4 | 4 | 5 |
| 15 | 0.018 | 4 | 5 | 4 | 4 | 4 | 2 | 2 | 4 | 2 | 2 |
| 16 | 0.28 | 3 | 3 | 3 | 2 | 3 | 1 | 2 | 2 | 1 | 1 |
| 18 | 1.1 | 4 | 4 | 2 | 3 | 3 | 2 | 3 | 2 | 2 | 2 |
| 25 | 0.56 | 4 | 4 | 3 | 4 | 4 | 3 | 5 | 2 | 4 | 2 |
| 26 | 2.2 | 2 | 3 | 2 | 3 | 2 | 2 | 2 | 2 | 1 | 1 |
| 28 | 2.2 | 5 | 4 | 3 | 3 | 3 | 3 | 2 | 2 | 2 | 2 |
| 30 | 2.2 | 2 | 3 | 1 | 2 | 2 | 1 | 1 | 1 | 1 | 1 |
| 31 | 1.1 | 4 | 4 | 2 | 4 | 3 | 2 | 2 | 3 | 1 | 2 |
| 32 | 1.1 | 4 | 4 | 2 | 3 | 4 | 2 | 2 | 2 | 2 | 2 |
| 34 | 1.1 | 3 | 2 | 2 | 2 | 3 | 1 | 2 | 2 | 1 | |
| 35 | 2.2 | 4 | 4 | 3 | 5 | 3 | 2 | 2 | 2 | 2 | 2 |
| 37 | 2.2 | 4 | 5 | 2 | 3 | 3 | 2 | 4 | 2 | 3 | 2 |
| 41 | 1.1 | 5 | 5 | 4 | 5 | 3 | 4 | 5 | 5 | 5 | 4 |
| 42 | 1.1 | 5 | 5 | 5 | 5 | 5 | 5 | 5 | 4 | 5 | 5 |
| 43 | 0.56 | 4 | 5 | 3 | 3 | 4 | 2 | 3 | 2 | 2 | 2 |
| 44 | 0.14 | 4 | 4 | 2 | 4 | 3 | 2 | 1 | 2 | 2 | 3 |
| 45 | 0.14 | 5 | 5 | 3 | 5 | 5 | 3 | 2 | 4 | 4 | 3 |
| 46 | 2.2 | 5 | 4 | 3 | | 4 | 2 | 4 | 2 | 3 | 2 |
| 47 | 0.07 | 4 | 5 | 5 | 4 | 4 | 2 | 3 | 2 | 2 | 2 |
| 48 | 2.2 | 4 | 5 | 3 | 4 | 4 | 1 | 4 | 2 | 2 | 1 |
| 51 | 0.14 | 5 | 5 | 3 | 5 | 4 | 2 | 3 | 3 | 2 | 2 |
| 53 | 2.2 | 4 | 4 | 2 | 3 | 3 | 2 | 3 | 1 | 1 | |
| 54 | 0.28 | 4 | 5 | 4 | 4 | 4 | 2 | 4 | 3 | 4 | 2 |
| 58 | 0.56 | 4 | 3 | 2 | 3 | 3 | 2 | 3 | 1 | 2 | 2 |
| 59 | 0.56 | 3 | 4 | 3 | 4 | 4 | 2 | 2 | 2 | 2 | 2 |
| 63 | 2.2 | 3 | 4 | 3 | 3 | 2 | 2 | 2 | 2 | 3 | 2 |
| 64 | 0.07 | 3 | 5 | 3 | 1 | 4 | 2 | 2 | 2 | 2 | 2 |
| 65 | 0.14 | 4 | 5 | 4 | 2 | 5 | 4 | 2 | 4 | 4 | 4 |
| 66 | 0.07 | 3 | 5 | 4 | 2 | 4 | 3 | 3 | 3 | 3 | 2 |
| 68 | 1.1 | 5 | 5 | 5 | 5 | 5 | 3 | 5 | 4 | 4 | 5 |
| 69 | 4.5 | 2 | 2 | 2 | 4 | 3 | 1 | 4 | 2 | 2 | 2 |
| 108 | 0.14 | 4 | 5 | 4 | 4 | 4 | 4 | 4 | 3 | 4 | 4 |
| 109 | 1.1 | 4 | 1 | 2 | 2 | 1 | 2 | 1 | 2 | 1 | 1 |
| 110 | 0.28 | 4 | 5 | 2 | 2 | 3 | 2 | 2 | 3 | 2 | 3 |
| 111 | 0.018 | 3 | 5 | 5 | 3 | 4 | 2 | 2 | 2 | 2 | 2 |
| 113 | 0.56 | 5 | 5 | 5 | 5 | 5 | 5 | 5 | 5 | 5 | 5 |
| 114 | 1.1 | 4 | 4 | 3 | 3 | 3 | 1 | 2 | 2 | 1 | 1 |

Table 3-continued

| | | | | | | | | | | |
|---|---|---|---|---|---|---|---|---|---|---|
| 115 | 1.1 | 4 | 5 | 5 | 5 | 4 | 1 | 3 | 2 | 2 | 2 |
| 116 | 0.14 | 4 | 5 | 5 | 4 | 4 | 4 | 3 | 4 | 2 | 2 |
| 118 | 1.1 | 5 | 5 | 5 | 5 | 5 | 5 | 5 | 5 | 5 | 5 |
| 123 | 0.28 | 4 | 5 | 3 | 4 | 4 | 2 | 3 | 3 | 3 | 3 |
| 186 | 2.2 | 4 | 5 | 3 | 5 | 5 | | 5 | 4 | 1 | 3 |
| 204 | 0.56 | 4 | 4 | 2 | 3 | 3 | 1 | 2 | 2 | 4 | 2 |
| 205 | 1.1 | 4 | 4 | 3 | 4 | 4 | 2 | 2 | 2 | 2 | 2 |
| 208 | 0.56 | 4 | 3 | 3 | 5 | 3 | 2 | 2 | 2 | 2 | 1 |
| 217 | 2.2 | 4 | 4 | 3 | 5 | 3 | 1 | 2 | 2 | 2 | 3 |
| 219 | 0.14 | 3 | 3 | 3 | 3 | 4 | 1 | 2 | 2 | 2 | 2 |
| 220 | 0.56 | 5 | 5 | 5 | 5 | 5 | 2 | 4 | 4 | 4 | 3 |
| 221 | 0.28 | 5 | 5 | 4 | 5 | 4 | 2 | 4 | 4 | 4 | 2 |
| 222 | 1.1 | 5 | 5 | 5 | 5 | 5 | 5 | 5 | 5 | 5 | 5 |
| 225 | 1.1 | 4 | 4 | 4 | 4 | 2 | 2 | 2 | 2 | 2 | 2 |
| 226 | 1.1 | 4 | 4 | 4 | 4 | 3 | 2 | 2 | 3 | 2 | 2 |
| 227 | 1.1 | 5 | 5 | 5 | 5 | 5 | 4 | 4 | 4 | 4 | 5 |
| 229 | 4.5 | 4 | 5 | 5 | 5 | 3 | 1 | 2 | 1 | 2 | 2 |
| 231 | 0.14 | 3 | 4 | 4 | 4 | 5 | 2 | 2 | 3 | 1 | 2 |
| 237 | 0.14 | 3 | 4 | 5 | 5 | 3 | 2 | 3 | 2 | 2 | 2 |
| 238 | 0.56 | 4 | 5 | 3 | 2 | 5 | 2 | 2 | 2 | 2 | 2 |
| 239 | 0.28 | 4 | 4 | 3 | 5 | 4 | 2 | 2 | 2 | 2 | 2 |

Table 4

| Compound of Example No. | Rate of Appln. kg./ha. | Postemergence | | | | | | |
|---|---|---|---|---|---|---|---|---|
| | | Corn | Large Crabgrass | Pigweed | Foxtail | Velvetleaf | Morningglory | Zinnia |
| 1 | 2.2 | 3 | 4 | 3 | 4 | 3 | 3 | 3 |
| 2 | 2.2 | 2 | 2 | 2 | 2 | 2 | 2 | 2 |
| 3 | 1.1 | 3 | 3 | 2 | 2 | 2 | 2 | 3 |
| 8 | 1.1 | 3 | 2 | 2 | 2 | 2 | 2 | 2 |
| 13 | 1.1 | 4 | 3 | 2 | 2 | 3 | 3 | 3 |
| 14 | 1.1 | 4 | 3 | 2 | 3 | 3 | 3 | 2 |
| 25 | 2.2 | 2 | 3 | 3 | 3 | 3 | 3 | 3 |
| 26 | 2.2 | 2 | 2 | 2 | 2 | 2 | 2 | 2 |
| 28 | 2.2 | 3 | 3 | 3 | 3 | 3 | 3 | 3 |
| 30 | 2.2 | 2 | 2 | 3 | 2 | 3 | 2 | 3 |
| 32 | 1.1 | 2 | 3 | 3 | 3 | 3 | 2 | 3 |
| 34 | 1.1 | 2 | 2 | 2 | 2 | 2 | 2 | 2 |
| 35 | 2.2 | 3 | 2 | 2 | 2 | 2 | 2 | 2 |
| 37 | 2.2 | 3 | 4 | 3 | 4 | 3 | 3 | 3 |
| 38 | 1.1 | 2 | 2 | 3 | 3 | 3 | 3 | 3 |
| 39 | 1.1 | 2 | 2 | 3 | 2 | 3 | 3 | 2 |
| 40 | 1.1 | 2 | 2 | 2 | 2 | 3 | 2 | 2 |
| 41 | 1.1 | 3 | 4 | 2 | 3 | 3 | 2 | 3 |
| 42 | 1.1 | 3 | 3 | 3 | 3 | 3 | 3 | 3 |
| 66 | 1.1 | 3 | 3 | 2 | 3 | 2 | 2 | 2 |
| 110 | 1.1 | 2 | 2 | 3 | 2 | 2 | 3 | 2 |
| 113 | 0.56 | 3 | 4 | 3 | 3 | 3 | 2 | 3 |
| 222 | 1.1 | 3 | 4 | 3 | 3 | 3 | 3 | 3 |
| 227 | 1.1 | 3 | 3 | 3 | 3 | 2 | 2 | 3 |

EXAMPLE 260 yellow nutsedge test

Typical compounds were evaluated in the greenhouse against yellow nutsedge in a test method which followed in general the method of Example 257, except that the acetone-ethanol solution contained about 1.5 g./100 ml. of the test compound, and one part of the organic solution was diluted with 9 parts of water before application. Both preemergence and postemergence tests of the compounds were made, at the rate of 9.0 kg./ha. The results of testing typical compounds are presented in the table below.

Table 5

| Compound of Example No. | Preemergence 9 kg./ha. | Postemergence 9 kg./ha. |
|---|---|---|
| 1 | 5 | 5 |
| 2 | 4 | 1 |
| 3 | 4 | 4 |
| 5 | 3 | 3 |
| 6 | 3 | 3 |
| 7 | 5 | 5 |
| 8 | 5 | 5 |
| 9 | 5 | 5 |
| 10 | 5 | 4 |
| 11 | 5 | 4 |
| 12 | 2 | 1 |
| 15 | 5 | 5 |
| 16 | 4 | 3 |
| 18 | 2 | 1 |
| 19 | 2 | 1 |
| 20 | 1 | 1 |
| 21 | 1 | 1 |
| 22 | 1 | |
| 23 | 1 | |
| 24 | 3 | |
| 25 | 4 | |
| 26 | 1 | |
| 27 | 1 | |
| 28 | 4 | |
| 29 | 3 | |
| 30 | 3 | |
| 31 | 5 | 4 |
| 32 | 5 | 4 |

Table 5-continued

| Compound of Example No. | Preemergence 9 kg./ha. | Postemergence 9 kg./ha. |
|---|---|---|
| 33 | 1 | 1 |
| 35 | 5 | 4 |
| 37 | 5 | 4 |
| 38 | 3 | 2 |
| 39 | 3 | 2 |
| 40 | 4 | 2 |
| 41 | 5 | 4 |
| 42 | 5 | 4 |
| 43 | 3 | 3 |
| 44 | 4 | 4 |
| 45 | 5 | 5 |
| 46 | 3 | 1 |
| 47 | 4 | 4 |
| 48 | 3 | 3 |
| 49 | 4 | |
| 50 | 1 | |
| 51 | 5 | 4 |
| 52 | 1 | 2 |
| 53 | 3 | 3 |
| 54 | 5 | 5 |
| 55 | 1 | 1 |
| 58 | 4 | 4 |
| 59 | 3 | 4 |
| 60 | 1 | |
| 62 | 2 | |
| 63 | 1 | 2 |
| 64 | 5 | 4 |
| 65 | 5 | 4 |
| 66 | 5 | 5 |
| 67 | 1 | 1 |
| 68 | 4 | 4 |
| 69 | 2 | 2 |
| 108 | 5 | 4 |
| 109 | 1 | 1 |
| 112 | 3 | 3 |
| 113 | 5 | 4 |
| 114 | 1 | 2 |
| 115 | 3 | 2 |
| 119 | 2 | 1 |
| 121 | 5 | 2 |
| 123 | 5 | 4 |
| 124 | 1 | 1 |
| 205 | 2 | 1 |
| 206 | 2 | 1 |
| 207 | 1 | 1 |
| 208 | 2 | 2 |
| 211 | 3 | 3 |
| 217 | 1 | 1 |
| 218 | 1 | 1 |
| 220 | 4 | 3 |
| 221 | 3 | 3 |
| 222 | 5 | 4 |
| 224 | 1 | 1 |
| 225 | 1 | 2 |
| 226 | 2 | 1 |
| 227 | 4 | 4 |
| 228 | 1 | 2 |
| 229 | 1 | 2 |
| 231 | 4 | 4 |
| 236 | 2 | 1 |
| 237 | 3 | 3 |
| 238 | 4 | 3 |
| 239 | 5 | 4 |

EXAMPLE 261 broadleaf weed test

A number of typical compounds were tested in the greenhouse against broadleaf weeds which are representative of families of weeds which exhibit resistance to many known herbicides. The test method was generally the same as the method of Example 260, except that only preemergence applications of the compounds were made. All compounds were tested at 9.0 kg./ha.

Table 6

| Compound of Example No. | Garden Huckleberry | Sicklepod | Common Ragweed | Prickly Sida | Black Night shade |
|---|---|---|---|---|---|
| 1 | 5 | 5 | 5 | | |
| 2 | 5 | 5 | 5 | | |
| 3 | 5 | 4 | 4 | | |
| 5 | 5 | 2 | 4 | | |
| 6 | 5 | 5 | 4 | | |
| 7 | 5 | 5 | 5 | | |
| 8 | 5 | 5 | 5 | | |
| 9 | 5 | 5 | 5 | | |
| 10 | 5 | 5 | 5 | | |
| 11 | 5 | 5 | 5 | | |
| 12 | 4 | 3 | 4 | | |
| 15 | 5 | 5 | 5 | | |
| 16 | 5 | 3 | 3 | | |
| 18 | 3 | 2 | 4 | | |
| 19 | 4 | 3 | 5 | | |
| 20 | 2 | 2 | 3 | | |
| 21 | 2 | 1 | 2 | | |
| 22 | 3 | 1 | | 2 | |
| 23 | 2 | 2 | 2 | | |
| 24 | 3 | 3 | 4 | | |
| 25 | 5 | 5 | 5 | | |
| 26 | 2 | 5 | 4 | | |
| 27 | 2 | 3 | 2 | | |
| 28 | 5 | 5 | 5 | | |
| 29 | 5 | 3 | 4 | | |
| 30 | 5 | 2 | 4 | | |
| 31 | 5 | 4 | 5 | | |
| 32 | 5 | 5 | 5 | | |
| 33 | 3 | 2 | 3 | | |
| 35 | 5 | 5 | 5 | | |
| 37 | 5 | 5 | 5 | | |
| 38 | 3 | 3 | 4 | | |
| 39 | 5 | 4 | 5 | | |
| 40 | 5 | 4 | 5 | | |
| 41 | 5 | 5 | 5 | | |
| 42 | 5 | 5 | 5 | | |
| 43 | 4 | 3 | 4 | | |
| 44 | 4 | 3 | 3 | | |
| 45 | 5 | 5 | 5 | | |
| 46 | 3 | 4 | 5 | | |
| 47 | 5 | 4 | 4 | | |
| 48 | 5 | 2 | 3 | | |
| 49 | 1 | 1 | 1 | | |
| 50 | 1 | 1 | 1 | | |
| 51 | 5 | 5 | 5 | | |
| 52 | 3 | 2 | 5 | | |
| 54 | 5 | 5 | 5 | | |
| 55 | 1 | 1 | 1 | | |
| 58 | 5 | 5 | 5 | | |
| 59 | 5 | 5 | 5 | | |
| 60 | 1 | 1 | 1 | | |
| 62 | 3 | 3 | | 3 | |
| 63 | 5 | 4 | 3 | | |
| 64 | 5 | 5 | 5 | | |
| 65 | 5 | 5 | 5 | | |
| 67 | 2 | 1 | 2 | | |
| 68 | | 5 | | 5 | 5 |
| 69 | 3 | 1 | 1 | | |
| 108 | 5 | 5 | 5 | | |
| 109 | 4 | 3 | 4 | | |
| 112 | 4 | 2 | 4 | | |
| 114 | | 2 | | 2 | 3 |
| 115 | | 4 | | 4 | 4 |
| 119 | 2 | 1 | 2 | | |
| 121 | 2 | 2 | 5 | | |
| 123 | 5 | 5 | 5 | | |
| 124 | 2 | 2 | 2 | | |
| 205 | 5 | 5 | 5 | | |
| 206 | 2 | 2 | 2 | | |
| 207 | 1 | 1 | 1 | | |
| 208 | 5 | 3 | 3 | | |
| 209 | 2 | 2 | 2 | | |
| 211 | 5 | 2 | 5 | | |
| 217 | 3 | 1 | 2 | | |
| 218 | 1 | 1 | 1 | | |
| 220 | 5 | 5 | 5 | | |
| 221 | 5 | 3 | 5 | | |
| 222 | 5 | 5 | 5 | | |

Table 6-continued

| Compound of Example No. | Garden Huckleberry | Sickle-pod | Common Ragweed | Prickly Sida | Black Night shade |
|---|---|---|---|---|---|
| 224 | 2 | 1 | 2 | | |
| 225 | 3 | 2 | 2 | | |
| 226 | 5 | 5 | | 5 | |
| 227 | 5 | 5 | | 5 | |
| 228 | | 1 | | 4 | 4 |
| 229 | | 1 | | 3 | 3 |
| 231 | 5 | 5 | 5 | | |
| 236 | 3 | 3 | 3 | | |
| 237 | 4 | 2 | 3 | | |
| 238 | 5 | 2 | 4 | | |
| 239 | 5 | 5 | 5 | | | house at various rates as indicated in the table below. In all cases, the compounds were applied preemergence to the test plants and were incorporated in the soil before the seeds were planted. In general, the formulation of the compounds and planting and observation of the test plants proceeded according to the method of Example 260, except that the compounds were dissolved in acetone-ethanol at 1 g./100 ml. concentration before dilution with water for application.

EXAMPLE 263

14-species greenhouse test

In this test, the test compounds were applied to the

Table 7

| Compound of Example No. | Rate of Appln. | Corn | Foxtail Millet | Grain Sorghum | Wild Oat | Rice | Barnyard Grass | Wheat | Morning-glory | Soybean | Prickly Sida | Cotton | Pigweed | Cucumber | Jimsonweed |
|---|---|---|---|---|---|---|---|---|---|---|---|---|---|---|---|
| 1 | 0.14 | 10 | 9 | 9.5 | 10 | 8.5 | 10 | 10 | 9 | 10 | 10 | 0 | 10 | 10 | 10 |
| 2 | 0.56 | 7 | 8 | 6 | 5 | 0 | 7 | 7 | 5 | 5 | 4 | 0 | 5 | 5 | 4 |
| 3 | 0.14 | 7 | 5 | 6 | 9 | 8 | 8 | 9 | 2 | 2 | 4 | 0 | 10 | 9.5 | 9 |
| 5 | 0.28 | 9 | 8 | 9 | 9 | 7 | 9 | 9 | 5 | 5 | 2 | 0 | 8 | 2 | 7 |
| 6 | 0.28 | 5 | 3 | 3 | 5 | 0 | 6 | 5 | 0 | 0 | 0 | 0 | 7 | 0 | 1 |
| 7 | 0.14 | 10 | 10 | 9.5 | 10 | 10 | 10 | 10 | 9.8 | 10 | 10 | 0 | 8 | 10 | 10 |
| 8 | 0.14 | 9.5 | 7 | 7 | 9.5 | 4 | 8 | 9 | 4 | 6 | 8 | 0 | 3 | 0 | 2 |
| 9 | 0.14 | 9 | 6 | 6 | 10 | 8 | 9 | 9 | 5 | 5 | 0 | 0 | 0 | 9 | 8 |
| 10 | 0.28 | 9 | 6 | 8 | 9.5 | 7 | 8 | 9 | 2 | 2 | 1 | 0 | 6 | 6 | 5 |
| 11 | 0.28 | 6 | 3 | 5 | 6 | 2 | 5 | 7 | 0 | 0 | 0 | 0 | 7 | 0 | 0 |
| 13 | 0.14 | 10 | 9.5 | 9.5 | 10 | 9.5 | 9.5 | 9.5 | 8.5 | 9.5 | 10 | 0 | 8 | 9.5 | 10 |
| 14 | 0.14 | 10 | 8.5 | 9.5 | 10 | 9.5 | 10 | 10 | 10 | 8.5 | 10 | 0 | 9.5 | 10 | 10 |
| 15 | 0.28 | 10 | 10 | 10 | 10 | 10 | 10 | 10 | 10 | 9.5 | 10 | | 10 | 10 | 10 |
| 16 | 0.56 | 6 | 5 | 4 | 7 | 2 | 7 | 7 | 0 | 0 | 0 | 0 | 5 | 5 | 5 |
| 28 | 0.28 | 10 | 9.5 | 10 | 10 | 9.8 | 10 | 10 | 9.8 | 9 | 9.5 | 0 | 10 | 2 | 7.5 |
| 31 | 0.14 | 8 | 5 | 6 | 8 | 6 | 7 | 8 | 2 | 2 | 1 | 0 | 8 | 0 | 4 |
| 37 | 0.28 | 9 | 9 | 9 | 10 | 6 | 10 | 10 | 8.5 | 8.5 | 6 | 0 | 0 | 3 | 5 |
| 41 | 0.14 | 10 | 9.5 | 9.5 | 10 | 9.8 | 10 | 10 | 10 | 10 | 6 | 0 | 0 | 8 | 8 |
| 42 | 0.28 | 10 | 10 | 10 | 10 | 10 | 10 | 10 | 9.5 | 10 | 10 | 0 | 10 | 10 | 10 |
| 43 | 0.56 | 8 | 5 | 7 | 9 | 4 | 8 | 9 | 1 | 1 | 0 | 0 | 0 | 0 | 0 |
| 44 | 0.56 | 8.5 | 5 | 7 | 9.5 | 9.5 | 9.5 | 9.5 | 3 | 2 | 1 | 0 | 8 | 0 | 4 |
| 45 | 0.28 | 10 | 9.5 | 9.5 | 10 | 9.5 | 10 | 10 | 7 | 7 | 6 | 0 | 10 | 9 | 10 |
| 46 | 1.1 | 9.8 | 9.5 | 7 | 7 | 1 | 9 | 9 | 8 | 9.5 | 4 | 0 | 4 | 3 | 3 |
| 47 | 0.28 | 9 | 9 | 8 | 9 | 8 | 9 | 9 | 5 | 5 | 3 | 0 | 9 | 4 | 7 |
| 51 | 0.28 | 10 | 9.5 | 9.5 | 10 | 9.5 | 10 | 10 | 8.5 | 9.5 | 10 | 0 | 10 | 10 | 10 |
| 53 | 0.56 | 6 | 2 | 1 | 3 | 1 | 2 | 7 | 0 | 2 | 0 | 0 | 2 | 1 | 0 |
| 54 | 0.28 | 9 | 9 | 8.5 | 10 | 9 | 9.5 | 9.5 | 8 | 6.5 | 6 | 0 | 9.5 | 8 | 8 |
| 58 | 1.1 | 10 | 9.8 | 7 | 9.5 | 1 | 9 | 9.5 | 9.8 | 8 | 10 | | 9.5 | 3 | 2 |
| 59 | 0.56 | 4 | 5 | 3 | 4 | 1 | 4 | 4 | 5 | 6 | 2 | 1 | 2 | 3 | 1 |
| 64 | 0.14 | 10 | 9.5 | 9 | 9 | 6 | 9.5 | 9.5 | 8 | 10 | 8 | 0 | 0 | 10 | 8 |
| 65 | 0.14 | 9.5 | 10 | 9 | 9.5 | 9 | 10 | 9 | 9 | 10 | 9 | 0 | 0 | 10 | 10 |
| 66 | 0.14 | 10 | 10 | 10 | 10 | 9 | 10 | 10 | 9 | 10 | 9 | 0 | 0 | 10 | 10 |
| 108 | 0.14 | 10 | 10 | 9 | 10 | 8 | 10 | 9.5 | 9 | 10 | 8 | 0 | 2 | 10 | 10 |
| 110 | 0.28 | 3 | 3 | 0 | 0 | 0 | 3 | 2 | 5 | 5 | 5 | 0 | 5 | 6 | 7 |
| 111 | 0.14 | 10 | 10 | 10 | 10 | 9 | 10 | 10 | 9 | 9 | 8 | 0 | 5 | 10 | 9 |
| 112 | 0.56 | 5 | 5 | 3 | 2 | 0 | 3 | 8 | 0 | 0 | 0 | 0 | 0 | 0 | 2 |
| 113 | 0.14 | 10 | 10 | 10 | 10 | 8 | 10 | 10 | 9 | 8 | 10 | 0 | 4 | 6 | 7 |
| 114 | 0.28 | 0 | 0 | 0 | 0 | 0 | 0 | 0 | 0 | 0 | 0 | 0 | 0 | 0 | 0 |
| 123 | 0.14 | 6 | 9 | 2 | 2 | 0 | 3 | 3 | 5 | 5 | 8 | 0 | 4 | 5 | 7 |
| 204 | 1.1 | 2 | 4 | 1 | 0 | 0 | 8 | 1 | 6 | 5 | 3 | 0 | 1 | 5 | 5 |
| 205 | 1.1 | 1 | 3 | 0 | 0 | 2 | 7 | 1 | 5 | 5 | 3 | 0 | 1 | 5 | 4 |
| 206 | 1.1 | 0 | 1 | 0 | 0 | 0 | 0 | 0 | 1 | 2 | 1 | 0 | 1 | 2 | 2 |
| 208 | 0.56 | 5 | 3 | 2 | 6 | 4 | 7 | 7 | 0 | 0 | 0 | 0 | 6 | 0 | 2 |
| 219 | 0.28 | 9.5 | 9 | 9.5 | 10 | 9 | 10 | 10 | 8 | 10 | 7 | 0 | 7 | 8 | 8 |
| 220 | 0.28 | 8.5 | 9 | 8 | 8 | 7 | 9 | 10 | 6 | 6 | 7 | 0 | 4 | 9 | 9 |
| 221 | 0.28 | 9 | 9 | 8.5 | 9 | 8 | 9 | 9 | 4 | 4 | 7 | 0 | 8 | 6 | 9 |
| 222 | 0.28 | 10 | 9 | 9.5 | 10 | 9 | 10 | 10 | 10 | 9 | 9.5 | 2 | 9 | 10 | 9 |
| 227 | 0.28 | 10 | 9.5 | 9.5 | 10 | 9.5 | 9.5 | 10 | 9 | 8 | 10 | 0 | 10 | 10 | 10 |
| 231 | 0.28 | 9 | 8 | 8 | 8 | 8 | 9.5 | 10 | 2 | 7 | 5 | 0 | 10 | 10 | 10 |
| 237 | 0.28 | 5 | 5 | 4 | 6 | 5 | 7 | 7 | 2 | 0 | 0 | 0 | 3 | 0 | 3 |
| 238 | 0.56 | 9.5 | 8 | 7 | 7 | 3 | 8 | 8 | 3 | 3 | 2 | 0 | 2 | 0 | 3 |
| 239 | 0.14 | 5 | 4 | 3 | 5 | 2 | 6 | 4 | 0 | 2 | 0 | 0 | 3 | 0 | 3 |

EXAMPLE 262 soil-incorporated fourteen-species test

This test was performed to evaluate typical compounds of the invention against a number of crop and weed species. The compounds were tested in the greenhouse at various rates as indicated in the table below. In all cases, the compounds were applied preemergence to the test plants and were incorporated in the soil before the seeds were planted. In general, the formulation of the compounds and planting and observation of the test plants proceeded according to the method of Example 260, except that the compounds were dissolved in acetone-ethanol at 1 g./100 ml. concentration before dilution with water for application.

surface of the soil preemergence to the test plants. Again, the test method was in general the method of Example 260. Various application rates were used as indicated below, and typical results were as follows. Different plant species were used in testing different compounds.

Table 8

| Compound of Example No. | Rate of Appln. kg./ha. | Sickle-pod | Garden Huckle-berry | Cotton | Rag-weed | Soy-bean | Venice Mallow | Morn-ing-glory | Jim-son-weed | Fox-tail Mil-let | Pig-weed | Corn | Lambs-quarter | Crab-grass | Velvet-leaf | Prickly Sida | Grain Sorghum | Wild Oat | Rice | Barn-yard-grass | Wheat | Sugar Beet | Yellow Nut-sedge | Cu-cum-ber |
|---|---|---|---|---|---|---|---|---|---|---|---|---|---|---|---|---|---|---|---|---|---|---|---|---|
| 1 | 0.28 | | | 0 | | 8 | | 10 | 10 | 10 | 10 | 9.5 | | | | 10 | 9.5 | 10 | 9.5 | 10 | 10 | | | 10 |
| 2 | 1.1 | | | 0 | | 3 | | 4 | 3 | 4 | 10 | 4 | | | | | 2 | 2 | 2 | 3 | 2 | 2 | | 2 |
| 3 | 0.28 | | | 0 | | 4 | | 4 | 5 | 10 | 9 | 9 | | | | 10 | 8 | 8 | 5 | 9.5 | 7 | | | 7 |
| 5 | 0.28 | | | 0 | | 4 | | 4 | 6 | 9 | 3 | 3 | | | | 7 | 3 | 4 | 3 | 9 | 5 | | | 2 |
| 6 | 2.2 | | | 0 | | 0 | | 2 | 3 | 7 | 3 | 4 | | | | 5 | 5 | 4 | 2 | 9.5 | 4 | | | 2 |
| 7 | 0.28 | | | 0 | | 8 | | 8 | 10 | 10 | 10 | 10 | | | | 10 | 8 | 8.5 | 8 | 10 | 8 | | | 10 |
| 8 | 1.1 | | | 0 | | 7 | | 8 | 9.5 | 10 | 10 | 6 | | | | 10 | 7 | 10 | 6 | 10 | 5 | | | 8 |
| 9 | 0.56 | | | 0 | | 3 | | 6 | 5 | 9 | 10 | 8 | | | | 9 | 9 | 10 | 9 | 10 | 4 | | | 5 |
| 10 | 1.1 | | | 0 | | 3 | | 9 | 7 | 10 | 10 | 7 | | | | 5 | 7 | 7 | 3 | 10 | 4 | | | 5 |
| 11 | 1.1 | | | 0 | | 3 | | 4 | 9 | 9 | 9 | 8 | | | | 5 | 5 | 7 | 6 | 10 | 5 | | | 5 |
| 13 | 0.28 | | | 0 | | 6 | | 5 | 10 | 10 | 10 | 9 | | | | 8 | 7 | 8 | 7 | 10 | 6 | | | 4 |
| 14 | 0.28 | | | 0 | | 8 | | 10 | 10 | 10 | 10 | 9 | | | | 9 | 5 | 9 | 6 | 10 | 9 | | | 7 |
| 15 | 0.28 | | | 2 | | 8 | | 10 | 10 | 10 | 10 | 9 | | | | 10 | 8.5 | 8 | 9 | 10 | 8 | | | 10 |
| 16 | 2.2 | | | 0 | | 2 | | 3 | 8 | 10 | 10 | 4 | | | | 5 | 2 | 9 | 2 | 9 | 7 | | | 2 |
| 19 | 1.1 | 3 | 3 | 0 | 3 | 3 | 3 | 3 | 4 | 4 | 5 | 0 | 5 | 9 | 3 | | | | | | | | | |
| 25 | 0.56 | 5 | 3 | 0 | | 4 | 8 | 4 | 5 | 7 | 10 | 6 | 8 | 10 | 3 | | | | | | | | | |
| 28 | 1.1 | 6 | 8 | 2 | 10 | 4 | | 10 | 9 | 10 | 10 | 10 | 10 | 10 | 10 | 10 | | | | | | | | |
| 31 | 0.28 | | | 0 | | 4 | | 10 | 8 | 9.5 | 3 | 9.5 | | | | 10 | 8 | 9.5 | 8.5 | 9.5 | 8.5 | | | 3 |
| 32 | 1.1 | 5 | 5 | 0 | | 5 | 10 | 10 | 5 | 10 | 7 | 7 | 10 | 10 | 10 | 10 | | | | | | | | |
| 35 | 1.1 | 5 | 3 | 0 | | 4 | 10 | 7 | 8 | 10 | 7 | 7 | 10 | 10 | 4 | | | | | | | | | |
| 37 | 0.56 | | | 0 | | 3 | | 4 | 0 | 10 | 3 | 5 | | | | 6 | 4 | 5 | 2 | 9 | 2 | | | 2 |
| 41 | 0.28 | | | 0 | | 8 | | 9 | 10 | 10 | 10 | 9.5 | | | | 9 | 9.5 | 9.5 | 8.5 | 10 | 9 | | | 10 |
| 42 | 0.28 | | | 0 | | 4 | | 4 | 7 | 10 | 4 | 2 | | | | 10 | 9 | 5 | 6 | 10 | 9.5 | | | 6 |
| 43 | 1.1 | | | 0 | | 0 | | 2 | 2 | 10 | 5 | 2 | | | | 2 | 4 | 2 | 0 | 5 | 0 | | | 0 |
| 44 | 1.1 | | | 0 | | 4 | | 4 | 9 | 10 | 10 | 2 | | | | 9 | 0 | 9 | 0 | 10 | 7 | | | 0 |
| 45 | 0.56 | | | 0 | | 3 | | 7 | 3 | 7 | 4 | 2 | | | | 10 | 8 | 4 | 5 | 9 | 0 | | | 5 |
| 46 | 2.2 | | | 0 | | 2 | | 2 | 4 | 10 | 10 | 2 | | | | 4 | 0 | 7 | 2 | 9 | 3 | | | 3 |
| 47 | 0.28 | | | 0 | | 6 | | 4 | 3 | 10 | 7 | 9 | | | | 9 | 3 | 9 | 7 | 10 | 2 | | | 2 |
| 51 | 2.2 | | | 0 | | 0 | | 3 | 10 | 10 | 10 | 0 | | | | 8 | 8.5 | 5 | 2 | 9 | 7 | | | 10 |
| 53 | 2.2 | | | 0 | | 7 | | 8 | 2 | 7 | 10 | 6 | | | | 4 | 3 | 10 | 5 | 10 | 5 | | | 0 |
| 54 | 0.56 | | | 0 | | 3 | | 9 | 5 | 10 | 4 | 5 | | | | 9 | 7 | 5 | 5 | 9 | 3 | | | 3 |
| 58 | 1.1 | | | 2 | | 3 | | 2 | 4 | 10 | 3 | 3 | | | | 3 | 0 | 10 | 2 | 6 | 2 | | | 2 |
| 59 | 1.1 | | | 0 | | 4 | | 4 | 5 | 9.5 | 7 | 10 | | | | 9 | 2 | 4 | 0 | 5 | 4 | | | 2 |
| 64 | 0.56 | | | 0 | | 10 | | 10 | 7 | 10 | 10 | 4 | | | | 10 | 9 | 8 | 4 | 10 | 4 | | | 10 |
| 65 | 0.28 | | | 0 | | 7 | | 8 | 8 | 10 | 3 | 9.5 | | | | 9 | 4 | 6 | 8 | 10 | 4 | | | 10 |
| 66 | 0.56 | | | 0 | | 10 | | 10 | 10 | 10 | 3 | 4 | | | | 8 | 2 | 9 | 5 | 10 | 8 | | | 10 |
| 108 | 0.28 | | | 0 | | 8 | | 9 | 9 | 10 | 10 | 10 | | | | 10 | 8 | 4 | 8 | 10 | 7.5 | | | 10 |
| 110 | 0.56 | | | 0 | | 5 | | 9 | 5 | 10 | 3 | 5 | | | | 4 | 3 | 3 | 6 | 10 | 2 | | | 5 |
| 111 | 0.28 | | | 0 | | 6 | | 9 | 8 | 10 | 10 | 7 | | | | 10 | 9 | 8 | 7 | 10 | 9.5 | | | 5 |
| 112 | 2.2 | | | 0 | | 2 | | 2 | 4 | 9 | 5 | 2 | | | | 8 | 4 | 4 | 3 | 9 | 3 | | | 7 |
| 113 | 0.56 | | | 0 | | 8 | | 7 | 7 | 10 | 10 | 7 | | | | 10 | 5 | 5 | 4 | 7 | 9 | | | 0 |
| 114 | 0.28 | | | 0 | | 10 | | 9 | 2 | 10 | 5 | 0 | | | | 2 | 0 | 3 | 0 | 9 | 3 | | | 5 |
| 123 | 0.56 | | | 0 | | 2 | | 3 | 6 | 4 | 5 | 8 | | | | 10 | 4 | 2 | 4 | 7 | 2 | | | 6 |
| 204 | 2.2 | | | 0 | | 2 | | 4 | 5 | 10 | 2 | 4 | | | | 2 | 3 | 5 | 0 | 10 | 2 | | | 3 |
| 205 | 2.2 | | | 0 | | 2 | | 7 | 7 | 8 | 2 | 2 | | | | 5 | 2 | 2 | 0 | 7 | 2 | | | 3 |
| 206 | 2.2 | | | 0 | | 0 | | 0 | 5 | 5 | 2 | 4 | | | | 5 | 0 | 2 | 0 | 5 | 2 | | | 3 |
| 208 | 4.4 | | | 0 | | 0 | | 7 | 4 | 8 | 5 | 5 | | | | 0 | 2 | 2 | 2 | 7 | 2 | | | 3 |
| 219 | 1.1 | | | 0 | | 10 | | 7 | 10 | 8 | 10 | 5 | | | | 6 | 5 | 5 | 5 | 10 | 8 | | | 10 |
| 220 | 0.28 | | | 0 | | 3 | | 2 | 7 | 9 | 5 | 2 | | | | 8 | 3 | 0 | 3 | 9.5 | 2 | | | 2 |

Table 8-continued

| Compound of Example No. | Rate of Appln. kg./ha. | Sickle- pod | Garden Huckle- berry | Cot- ton | Rag- weed | Soy- bean | Venice Mallow | Morn- ing- glory | Jim- son- weed | Fox- tail Mil- let | Pig- weed | Corn | Lambs- quarter | Crab- grass | Velvet- leaf | Prickly Sida | Grain Sorghum | Wild Oat | Rice | Barn- yard- grass | Wheat | Sugar Beet | Yel- low Nut- sedge | Cu- cum- ber |
|---|---|---|---|---|---|---|---|---|---|---|---|---|---|---|---|---|---|---|---|---|---|---|---|---|
| 221 | 1.1 | | | 0 | | 5 | | 6 | 10 | 9.8 | 9 | 7 | | | | 10 | 7 | 6 | 4 | 9.8 | 7 | | | 7 |
| 222 | 1.1 | | | 0 | | 10 | | 9 | 10 | 10 | 10 | 10 | | | | 10 | 4 | 4 | 6 | 10 | 9 | | | 10 |
| 227 | 0.56 | | | 0 | | 7 | | 7.5 | 10 | 10 | 10 | 8 | | | | 10 | 7 | 8 | 5 | 10 | 9 | | 10 | |
| 231 | 1.1 | | | 0 | | 7 | | 6 | 9 | 9 | 9 | 7 | | | | 3 | 7 | 5 | 6 | 10 | 6 | | | 9 |
| 237 | 2.2 | | | 0 | | 4 | | 4 | 9.5 | 10 | 10 | 5 | | | | 4 | 4 | 4 | 4 | 9 | 7 | | | 0 |
| 238 | 2.2 | | | 0 | | 6 | | 4 | 4 | 9 | 9 | 9 | | | | 6 | 5 | 5 | 3 | 8 | 7 | | | 0 |
| 239 | 0.56 | | | 0 | | 3 | | 4 | 5 | 10 | 9 | 2 | | | | 3 | 3 | 5 | 2 | 9 | 2 | | | 2 |

EXAMPLE 264 soil-incorporated test

In this test, the compounds were incorporated in the soil before the seeds were planted. Again, the method of Example 260 was followed in general. Various compounds in this test were applied at a number of different application rates, and the various compounds were tested against various plant species.

Table 9

| Compound of Example No. | Appln. Rate kg./ha. | Jimson-weed | Garden Huckle-berry | Pig-weed | Cotton | Prickly Sida | Lambs-quarter | Morning-glory | Crab-grass | Yellow Nutsedge | Foxtail Millet | Velvet-leaf | Barnyard-grass | Hollyhock | Venice Mallow | Okra | Cocklebur |
|---|---|---|---|---|---|---|---|---|---|---|---|---|---|---|---|---|---|
| 1 | 0.21 | 8 | | 10 | 0 | 10 | | 10 | 10 | | 10 | 9 | | 10 | 10 | 4 | |
|   | 0.56 | 9 | | 10 | 0 | 10 | | 10 | 10 | | 10 | 10 | | 10 | 10 | 7 | |
| 2 | 0.28 | 2 | 3 | 3 | 0 | 5 | 6 | 3 | 5 | 0 | 3 | 3 | 3 | | | | 2 |
|   | 0.56 | 4 | 6 | 6 | 2 | 10 | 10 | 5 | 5 | 0 | 10 | 6 | 9 | | | | 4 |
|   | 1.1 | 6 | 10 | 9 | 2 | 10 | 10 | 10 | 10 | 4 | 10 | 10 | 10 | | | | 6 |
|   | 2.2 | 10 | 10 | 10 | 4 | 10 | 10 | 10 | 10 | 8 | 10 | 10 | 10 | | | | 8 |
| 3 | 0.21 | 5 | | 8 | 0 | 7 | | 6 | 8 | | 7 | | | | | | |
|   | 0.42 | 7 | | 10 | 0 | 8 | | 7 | 10 | | 10 | | | | | | |
|   | 0.56 | 7 | | 10 | 3 | 8 | | 7 | 10 | | 10 | | | | | | |
| 25 | 0.28 | 8 | 10 | 4 | 0 | 10 | 10 | 10 | 10 | 5 | 10 | 10 | 10 | | | | 7 |
|   | 0.56 | 10 | 10 | 7 | 3 | 10 | 10 | 10 | 10 | 8 | 10 | 10 | 10 | | | | 9 |
|   | 1.1 | 10 | 10 | 10 | 4 | 10 | 10 | 10 | 10 | 10 | 10 | 10 | 10 | | | | 10 |
|   | 2.2 | 10 | 10 | 10 | 8 | 10 | 10 | 10 | 10 | 10 | 10 | 10 | 10 | | | | 10 |
| 28 | 0.21 | 10 | 10 | 10 | 0 | 9 | 10 | 9 | 10 | 8 | 10 | 8 | 10 | 10 | 8 | 0 | 8 |
|   | 0.28 | 10 | 10 | 10 | 0 | 10 | 10 | 10 | 10 | 10 | 10 | 10 | 10 | 10 | 10 | 0 | 9 |
|   | 0.56 | 10 | 10 | 10 | 0 | 10 | 10 | 10 | 10 | 8 | 10 | 10 | 10 | 10 | 10 | 2 | 9 |
| 31 | 0.28 | 10 | 10 | 10 | 0 | 10 | 10 | 10 | 10 | 10 | 10 | 10 | 10 | | | | 10 |
|   | 0.56 | 10 | 10 | 10 | 0 | 10 | 9 | 8 | 10 | 3 | 10 | 10 | 10 | | | | 5 |
| 32 | 0.28 | 7 | 8 | 2 | 0 | 10 | | 10 | 10 | 5 | 10 | 10 | 10 | | | | 8 |
|   | 0.56 | 10 | 10 | 4 | 3 | 10 | 10 | 10 | 10 | 8 | 10 | 10 | 10 | | | | 10 |
|   | 1.1 | 10 | 10 | 7 | 3 | 10 | | | 10 | | 10 | 10 | 10 | | | | |
| 42 | 0.21 | 7 | | 9 | 0 | 7 | | 10 | 10 | | 10 | 10 | 10 | | | | |
|   | 0.56 | 8 | | 9 | 0 | 8 | | 10 | 10 | | 10 | 10 | 10 | | | | |

EXAMPLE 265 surface-applied multiple-crop test

Representative compounds of the invention were tested against a number of representative crop plants in a field screen test wherein the test plots were artificially seeded with weeds. Seeds of the crops shown in the table below were planted in rows in a medium-heavy midwestern soil. The compounds identified below were applied in bands across the rows of crop seeds, and were applied immediately after the seeds were planted. The bands were about 1 meter wide, so that each test plot included a 1-meter length of a row of each crop shown below. The compounds were sprayed on the surface of the soil in the form of an aqueous dispersion similar to those described above in Example 258.

All of the test plots were overseeded with pigweed and foxtail immediately before the plots were planted and treated with the compounds. Untreated control plots were provided for comparison with the treated plots.

A skilled plant scientist observed the plots 39 days after they were planted and treated, and estimated the percent control of the weeds and the percent injury to the crops. The results are shown in the table below.

EXAMPLE 266 soil-incorporated multiple-crop test

The procedure of Example 265 was followed, except that the compounds were incorporated with a rotary tiller immediately after application. Crop and weed seeds were planted immediately after application and incorporation of the compounds.

Table 11

| Compound of Example No. | Appln. Rate kg./ha. | Cotton | Peanuts | Sorghum | Rice | Wheat | Foxtail | Pigweed | Soybean |
|---|---|---|---|---|---|---|---|---|---|
| 1 | 0.56 | 0 | 53 | 50 | 83 | 93 | 98 | 78 | 70 |
| 2 | 0.28 | 0 | 0 | 7 | 17 | 7 | 10 | 0 | 7 |
|  | 0.56 | 0 | 13 | 10 | 20 | 3 | 0 | 0 | 7 |
|  | 1.1 | 0 | 17 | 10 | 13 | 20 | 13 | 27 | 7 |
|  | 2.2 | 13 | 23 | 17 | 33 | 30 | 78 | 0 | 23 |
| 25 | 0.28 | 10 | 0 | 3 | 25 | 17 | 13 | 30 | 3 |
|  | 0.56 | 20 | 27 | 23 | 23 | 47 | 83 | 10 | 33 |
|  | 1.1 | 0 | 63 | 57 | 63 | 80 | 97 | 20 | 50 |
|  | 2.2 | 0 | 63 | 85 | 90 | 100 | 99 | 32 | 73 |
| 28 | 0.28 | 0 | 30 | 27 | 30 | 37 | 55 | 10 | 23 |
|  | 0.56 | 7 | 7 | 37 | 60 | 83 | 96 | 17 | 27 |
|  | 1.1 | 0 | 50 | 73 | 83 | 100 | 99 | 78 | 83 |
|  | 2.2 | 0 | 50 | 92 | 93 | 100 | 100 | 94 | 80 |
| 31 | 0.28 | 0 | 0 | 17 | 40 | 33 | 37 | 0 | 13 |
|  | 0.56 | 10 | 7 | 33 | 70 | 50 | 72 | 10 | 30 |
|  | 1.1 | 0 | 17 | 33 | 77 | 93 | 95 | 67 | 47 |
|  | 2.2 | 17 | 30 | 60 | 87 | 97 | 100 | 94 | 70 |
| 32 | 0.28 | 0 | 0 | 20 | 30 | 13 | 0 | 0 | 7 |
|  | 0.56 | 13 | 20 | 23 | 43 | 47 | 60 | 10 | 20 |
|  | 1.1 | 20 | 10 | 33 | 57 | 63 | 94 | 0 | 30 |
|  | 2.2 | 0 | 33 | 67 | 95 | 90 | 98 | 7 | 57 |

EXAMPLE 267 perennial weed test

The compound of Example 1 was tested against typical perennial weeds. The compound was formulated according to the procedure of Example 257. Applications of the formulated compound were made to plastic pots of greenhouse soil which had been planted with bindweed, bermuda-grass, johnsongrass and quackgrass. Bindweed root stocks and johnsongrass and quackgrass rhizomes were obtained from field-growing plants, and bermudagrass stolons were rooted from greenhouse-grown bermudagrass flats.

The compound, in its formulated form, was sprayed evenly over the pots immediately after the weeds were planted, and was lightly watered into the soil. The pots were individually fertilized a few days after treatment.

Table 10

| Compound of Example No. | Appln. Rate kg./ha. | Cotton | Peanuts | Sorghum | Rice | Wheat | Foxtail | Pigweed | Soybean |
|---|---|---|---|---|---|---|---|---|---|
| 1 | 0.56 | 35 | 33 | 37 | 10 | 3 | 97 | 98 | 63 |
| 2 | 1.1 | 0 | 0 | 10 | 7 | 7 | 93 | 96 | 0 |
|  | 2.2 | 10 | 15 | 20 | 10 | 13 | 87 | 88 | 3 |
|  | 4.5 | 0 | 23 | 37 | 17 | 17 | 99 | 99 | 27 |
| 25 | 1.1 | 7 | 7 | 13 | 20 | 23 | 92 | 78 | 3 |
|  | 2.2 | 0 | 17 | 50 | 43 | 27 | 99 | 94 | 52 |
|  | 4.5 | 30 | 30 | 90 | 57 | 62 | 99 | 99 | 100 |
| 28 | 1.1 | 7 | 7 | 27 | 20 | 3 | 99 | 98 | 30 |
|  | 2.2 | 10 | 43 | 80 | 57 | 43 | 99 | 96 | 67 |
|  | 4.5 | 25 | 47 | 93 | 77 | 77 | 100 | 98 | 90 |
| 31 | 1.1 | 15 | 3 | 20 | 17 | 13 | 99 | 97 | 40 |
|  | 2.2 | 27 | 10 | 47 | 17 | 13 | 99 | 99 | 50 |
|  | 4.5 | 70 | 30 | 67 | 50 | 53 | 99 | 99 | 89 |
| 32 | 1.1 | 3 | 0 | 7 | 27 | 10 | 87 | 68 | 0 |
|  | 2.2 | 10 | 3 | 33 | 13 | 7 | 95 | 83 | 23 |
|  | 4.5 | 10 | 27 | 80 | 27 | 67 | 100 | 97 | 73 |

The pots were stored in the greenhouse, and the plants were observed five weeks after application of the compound. Weed control was rated on the 0-10 scale.

| Appln. Rate kg./ha. | Bind-weed | Bermuda-grass | Johnson-grass | Quack-grass |
|---|---|---|---|---|
| 0.28 | 10 | 5 | 1 | 8 |
| 0.56 | 10 | 7 | 3 | 10 |
| 1.1 | 10 | 7 | 5 | 9 |
| 2.2 | 10 | 8 | 5 | 9 |

The same compound was also tested against the same weeds in a postemergence test, wherein the weeds were allowed to grow for 30-60 days after planting before the compound was applied. Before application of the compound, the plants were trimmed back to a height of 4-8 inches, and the bindweed runners were trimmed back to the edge of the pot. The plants were observed four weeks after treatment. The results were as follows.

| Appln. Rate kg./ha. | Bind-weed | Bermuda-grass | Johnson-grass | Quack-grass |
|---|---|---|---|---|
| 0.28 | 8 | 8 | 8 | 5 |
| 0.56 | 8 | 8 | 8 | 10 |
| 1.1 | 8 | 8 | 8 | 10 |
| 2.2 | 8 | 7 | 8 | 10 |

EXAMPLE 268 perennial weed tests

In this typical experiment, the weeds and conditions were similar to those of Example 267. A number of exemplary compounds were used. The weeds were observed about four weeks after application of the compounds. The preemergence results were as follows.

| Compound of Example No. | Appln. Rate kg./ha. | Bind-weed | Bermuda-grass | Johnson-grass | Quack-grass |
|---|---|---|---|---|---|
| 1 | 1.1 | 10 | 9.8 | 10 | 10 |
|  | 0.56 | 10 | 9.8 | 10 | 10 |
|  | 0.28 | 10 | 8 | 10 | 10 |
|  | 0.14 | 10 | 8 | 9.5 | 10 |
| 13 | 1.1 | 10 | 9.5 | 9.5 | 10 |
|  | 0.56 | 10 | 8 | 9 | 10 |
|  | 0.28 | 10 | 8 | 8 | 8 |
|  | 0.14 | 10 | 6 |  | 8 |
| 15 | 1.1 | 10 | 9.5 | 10 | 10 |
|  | 0.56 | 10 | 9 | 10 | 10 |
|  | 0.28 | 10 | 9 | 7 | 9 |
|  | 0.14 | 10 | 7 | 7 | 7 |
| 45 | 1.1 | 10 | 9.5 | 10 | 10 |
|  | 0.56 | 10 | 9 | 10 | 10 |
|  | 0.28 | 10 | 5 | 7 | 6 |
|  | 0.14 | 10 | 4 |  | 7 |
| 51 | 1.1 | 10 | 9.5 | 10 |  |
|  | 0.56 | 10 | 9 | 9.5 | 10 |
|  | 0.28 | 10 | 7 | 10 | 9 |
|  | 0.14 | 10 | 5 | 7 | 7 |

The results of the postemergence experiments were as follows.

| Compound of Example No. | Appln. Rate kg./ha. | Bind-weed | Bermuda-grass | Johnson-grass | Quack-grass |
|---|---|---|---|---|---|
| 1 | 1.1 |  | 9.5 |  | 9.5 |
|  | 0.56 | 9 | 9.5 | 8 | 9 |
|  | 0.28 |  | 8 |  | 9.5 |
|  | 0.14 |  | 3 |  | 9 |
| 13 | 1.1 |  | 9 |  | 9 |
|  | 0.56 | 9.5 | 9 | 8 | 7 |
|  | 0.28 |  | 8 |  | 5 |
|  | 0.14 |  | 7 |  | 4 |
| 15 | 1.1 |  | 9 |  | 9 |
|  | 0.56 | 9.8 | 9 | 8 | 9 |
|  | 0.28 |  | 8 |  | 8 |
|  | 0.14 |  | 7 |  | 6 |
| 45 | 1.1 |  | 9 |  | 9 |
|  | 0.56 | 9 | 8 | 7 | 9 |
|  | 0.28 |  | 7 |  | 5 |
|  | 0.14 |  | 5 |  | 4 |
| 51 | 1.1 |  | 9 |  | 9 |
|  | 0.56 | 9.5 | 9 | 7 | 8 |
|  | 0.28 |  | 5 |  | 6 |
|  | 0.14 |  | 4 |  | 3 |

EXAMPLE 269 mesquite test

Typical compounds were tested against mesquite trees growing in the greenhouse. The trees were transplanted, when 5-12 inches tall, into 1-gallon metal pots. After the trees had begun to grow vigorously in the pots, the compounds were applied as a soil drench. The compounds were formulated for application by dissolving them in acetone:ethanol as described in Example 257, and dispersing the proper amount of the solution in 25 ml. of water for application to each pot. The mesquite trees were observed approximately 90 days after application of the compounds, and control was rated on the 0-10 scale.

| Compound of Example No. | Appln. Rate kg./ha. | Ratings |
|---|---|---|
| 1 | 1.1 | 9.8 |
|  | 2.2 | 9.9 |
|  | 4.5 | 9.9 |
| 7 | 1.1 | 10 |
|  | 2.2 | 9.5 |
|  | 4.5 | 9.9 |
| 8 | 1.1 | 2 |
|  | 2.2 | 7.5 |
|  | 4.5 | 4 |
| 9 | 1.1 | 6 |
|  | 2.2 | 7 |
|  | 4.5 | 9.9 |
| 13 | 1.1 | 3 |
|  | 2.2 | 9 |
|  | 4.5 | 6 |
| 14 | 1.1 | 10 |
|  | 2.2 | 10 |
|  | 4.5 | 10 |

| Compound of Example No. | Appln. Rate kg./ha. | Ratings |
|---|---|---|
| 28 | 1.1 | 6 |
|  | 2.2 | 6 |
|  | 4.5 | 7.5 |
| 31 | 1.1 | 7 |
|  | 2.2 | 4 |

-continued

| Compound of Example No. | Appln. Rate kg./ha. | Ratings |
|---|---|---|
|  | 4.5 | 8.5 |
| 41 | 1.1 | 9 |
|  | 2.2 | 9.5 |
|  | 4.5 | 9.9 |
| 42 | 1.1 | 10 |
|  | 2.2 | 9.9 |
|  | 4.5 | 10 |
| 45 | 1.1 | 0 |
|  | 2.2 | 4 |
|  | 4.5 | 7 |
| 51 | 1.1 | 0 |
|  | 2.2 | 0 |
|  | 4.5 | 4 |

EXAMPLE 270 grapefruit test

The compound of Example 1 was tested in a grapefruit grove in a tropical climate. The soil was sandy and the trees were grown with sprinkler irrigation in bedded culture. The trees were approximately two years old when the compound was applied.

The compound was formulated according to the method of Example 257, and was applied as a surface spray to a 1 meter square plot around the base of each tree.

Crop injury to the trees was rated on the 0-10 scale about 14 weeks after application of the compounds, with the following results.

| Rate kg./ha. | 0.14 | 0.21 | 0.28 | 0.42 | 0.56 | 1.1 | 2.2 | 4.5 |
|---|---|---|---|---|---|---|---|---|
|  | 0.0 | 0.0 | 0.0 | 0.0 | 0.0 | 0.7 | 0.0 | 0.0 |

Weed control was also observed about 14 weeks after application of the compound. The following results were observed, expressed as percent control based on the weed population of untreated control plots.

| Appln. Rate kg./ha. | Bahia-grass | Bermuda-grass | Purple Cud-weed | Cutleaf Evening-primrose | Florida Pusley | Black Night-shade |
|---|---|---|---|---|---|---|
| 0.14 | 0 | 0 | 83 | 100 | 63 | 97 |
| 0.21 | 0 | 40 | 100 | 100 | 53 | 97 |
| 0.28 | 13 | 13 | 100 | 100 | 62 | 100 |
| 0.42 | 80 | 73 | 98 | 100 | 100 | 100 |
| 0.56 | 87 | 88 | 100 | 100 | 100 | 100 |
| 1.1 | 90 | 73 | 100 | 100 | 95 | 100 |
| 2.2 | 100 | 80 | 100 | 100 | 90 | 100 |
| 4.5 | 98 | 98 | 100 | 100 | 100 | 100 |

EXAMPLE 271 purple nutsedge control in cotton tests

The compound of Example 1 was tested in field-growing cotton infested with purple nutsedge. The cotton was grown in a clay soil in flat culture, with no irrigation, in a sub-tropical climate. The compound was applied as a water-dispersed 80% wettable powder, and was incorporated into the soil immediately before the cotton was planted. Crop injury and weed control observations were made, in percent injury or control, approximately eight weeks after the compound was applied. The results were as follows.

| Appln. Rate kg./ha. | Crop Injury | Bristly Starbur Control | Purple Nutsedge Control | Red Tasselflower Control |
|---|---|---|---|---|
| 0.56 | 0 | 27 | 20 | 33 |
| 0.84 | 0 | 60 | 67 | 80 |
| 1.1 | 0 | 68 | 73 | 90 |
| 1.7 | 0 | 90 | 90 | 100 |
| 2.2 | 0 | 99 | 99 | 100 |
| 3.4 | 0 | 99 | 99 | 100 |

EXAMPLE 272 weed control in coffee tests

The compound of Example 1 was also applied to established coffee in experiments much like those of the example immediately above, except that the compound was surface applied. Application of the compound at rates up to 2 kg./ha. showed no injury to the coffee when the crop was observed approximately six weeks and approximately four months after application of the compound. Excellent control of annual grasses, annual broadleaves, Paraguay starbur, bristly starbur, hairy beggarticks, southern sandbur, and purple nutsedge was observed in the experment.

EXAMPLE 273 weed-control in rice tests

NATO rice and barnyard grass were seeded in large metal pots, and pyridone compounds were applied, according to three different methods. In all of the test methods, the compounds were formulated as 50 percent wettable powders.

A. The test compounds named below were incorporated into the top 8 cm. of soil in the pots according to the application rates named in the table below. The rice and barnyard grass seed were then planted 1.8-2.5 cm. deep. The pots were watered daily until the rice plants were 5-8 cm. tall, and then 5-8 cm. of flood water was added to the pots and maintained throughout the test.

B. The pots were filled with soil, and barnyard grass seeds were planted as above. From 5 to 8 cm. of flood water was added to the pots, and rice seedlings were transplanted into the pots. The test compounds were sprayed over the water three days after the rice plants were transplanted.

C. The test compounds were incorporated into the top 8 cm. of soil, and barnyard grass seeds were planted 1.8-2.5 cm. deep. From 5 to 8 cm. of flood water was then added to the pots, and rice seedlings were transplanted into the pots 5 days after treatment.

About 3 weeks after the tests were established, injury to the rice and control of the barnyard grass were measured on the 0-10 scale. The results are shown in the table below.

| Compound of Example No. | Appln. Rate kg./ha. | Test A Crop Injury | Test A Weed Control | Test B Crop Injury | Test B Weed Control | Test C Crop Injury | Test C Weed Control |
|---|---|---|---|---|---|---|---|
| 1 | 0.07 | 4 | 7.5 | 0 | 10 | 4 | 6 |
| 1 | 0.14 | 7.5 | 8 | 0 | 10 | 5 | 7 |

-continued

| Compound of Example No. | Appln. Rate kg./ha. | Test A | | Test B | | Test C | |
|---|---|---|---|---|---|---|---|
| | | Crop Injury | Weed Control | Crop Injury | Weed Control | Crop Injury | Weed Control |
| 152 | 0.28 | 0 | 7 | 0 | 7 | 0 | 6 |
| 152 | 0.42 | 0 | 7.5 | 0 | 8 | 0 | 7 |
| 152 | 0.56 | 0 | 8 | 0 | 10 | 0 | 8 |
| 152 | 0.75 | 0 | 8 | 0 | 9.5 | 0 | 8.5 |
| 152 | 0.84 | 0 | 10 | 0 | 10 | 0 | 9 |
| 160 | 0.28 | 0 | 6 | 0 | 9.5 | 0 | 4 |
| 160 | 0.42 | 0 | 7 | 0 | 10 | 0 | 7 |
| 160 | 0.56 | 0 | 9 | 0 | 10 | 0 | 8 |
| 160 | 0.75 | 0 | 10 | 0 | 10 | 0 | 9.5 |
| 160 | 0.84 | 0 | 10 | 0 | 10 | 0 | 10 |

EXAMPLE 274 aquatic herbicide tests

Field tests against representative aquatic weeds were carried out in artificial ponds about 1 meter in diameter and ½ meter deep. The ponds contained a layer of earth at the bottom, and were filled with water. Representative aquatic weeds were planted in the ponds, and compounds of this invention were added at application rates named in the table below. The application rates were calculated as parts per million by weight of the total amount of water in each pond. Three weeks, 7 weeks and 12 weeks after the ponds were treated with the test compounds, the percent weed control of each species was measured, and the control is reported in the table below as a mean of the three evaluations of each weed.

A preferred embodiment of the herbicidal method, however, is the use of the method to selectively kill herbaceous weeds.

Most unusually, the compounds are herbicidally effective when applied both preemergence and postemergence. Thus, they can be applied to the soil to kill weeds by soil contact when the weed seeds are germinating and emerging, and can also be used to kill emerged weeds by direct contact with the exposed portions of the weed. When the compounds are applied preemergence, the weeds are killed either during germination or shortly after emergence.

The compounds are effectively brought into contact with aquatic weeds by either suspending or dissolving the compound in the water in which the weeds grow, or by applying the compound to the sub-aqueous soil in which the weeds are rooted.

| Compound of Example No. | ppm | Hydrilla | Myriophyllum | Potamogeton | Najas | Ceratophyllum | Lemna |
|---|---|---|---|---|---|---|---|
| 1 | .03 | 65 | 100 | 100 | 100 | 95 | 85 |
| 1 | .1 | 83 | 100 | 97 | 98 | 95 | 85 |
| 1 | .3 | 100 | 100 | 100 | 100 | 100 | 100 |
| 72 | .03 | 98 | 100 | 100 | 100 | 100 | 50 |
| 72 | .1 | 100 | 100 | 100 | 100 | 100 | 90 |
| 72 | .3 | 100 | 100 | 100 | 100 | 100 | 99 |
| 118 | .03 | 82 | 100 | 100 | 100 | 100 | 60 |
| 118 | .1 | 100 | 100 | 100 | 100 | 100 | 100 |
| 118 | .3 | 58 | 50 | 50 | 58 | 85 | 70 |
| 146 | .03 | 25 | 65 | 22 | 32 | 45 | 0 |
| 146 | .1 | 53 | 92 | 58 | 81 | 85 | 75 |
| 146 | .3 | 78 | 100 | 100 | 100 | 100 | 99 |
| 172 | .03 | 21 | 5 | 3 | 10 | 25 | 0 |
| 172 | .1 | 13 | 13 | 5 | 20 | 50 | 30 |
| 172 | .3 | 65 | 62 | 58 | 63 | 85 | 65 |

The outstanding broad-spectrum activity of the compounds of this invention is clearly illustrated by the above examples. The examples point up the efficacy of the compounds against annual grasses, the relatively easily-controlled broadleaves such as pigweed, and the more difficult to kill broadleaves such as the nightshades, ragweed and sicklepod. Further, the compounds control such perennial weeds as johnsongrass, quackgrass, bindweed, bermudagrass and nutsedge, which are very difficult to control. The compounds also control algae and aquatic weeds, such as coontail, hydrilla and the like. Still further, the compounds kill such woody plants as mesquite, which is an economically harmful weed in arid climates. Thus, plant scientists will recognize that the compounds can be used to control undesirable woody plants where such plants are not wanted. Plant scientists will recognize that the exemplified activity of the compounds shows that the compounds are effective against all types of weeds.

Because of the oustanding efficacy of the compounds, a method of using the compounds for killing weeds is an important embodiment of the present invention. This embodiment is a method of selectively killing weeds which comprises contacting the weeds with an herbicidally-effective amount of one of the compounds described above. In the context of this invention, weed seeds, which are contacted with the compounds through preemergence applications of the compounds, are regarded as weeds.

Preemergence applications of the compounds are effective, as the examples show, whether the compounds are applied to the surface of the soil or are incorporated in the soil.

As the examples above illustrate, many of the compounds are acceptably safe to a number of crops, such as peanuts, soybean, surghum, wheat and tree crops when applied at proper rates and at appropriate times. It will be noted that the compounds are particularly and notably harmless to cotton in the exemplified experiments.

Because of the safety with which this crop may be treated with the compounds, the use of the method to kill weeds in cotton cropland is a preferred embodiment of the invention.

Observation of the data above shows that the compounds are also notably safe to rice. Accordingly, use of the method to kill weeds in rice cropland, and particularly in rice cropland in flooded transplant culture, is a preferred embodiment of the invention.

The compounds can also be used, at appropriate application rates, for the total control of vegetation. Such control is often desired, as for keeping cropland fallow for a time, or on industrial property and rights-of-way. The compounds' ability to control perennial weeds and woody plants makes them particularly valuable total vegetation control agents.

The method is notable for its ability selectively to kill weeds. The term weeds is not used here in a restrictive sense, but is used to refer broadly to undesired and undesirable plants. For example, the method may be used in cotton cropland to kill not only plants which are undesirable per se, such as johnsongrass and ragweed, but also volunteer crop plants which are undesirable in a cotton field. It will be understood that the proper application rates must be used to achieve selective control of weeds, as plant scientists are well aware.

The proportion of the weed population which is killed by an application of one of the compounds depends upon the species of the weed and the identity and amount of the compound applied. In many instances, of course, the whole population is killed. In other instances, part of the weeds are killed and part are injured, as some of the examples above illustrate. It will be understood that an application of one of the compounds is effective and beneficial, even though only part of the weed population is killed and another part of the population is injured. The mere injury of a weed is beneficial, because the surrounding crop, growing normally, shades out the slow-growing injured weed.

The best application rate of a given compound of the invention for the control of a given weed varies, of course, depending upon the method of compound application, climate, soil type, water and organic matter contents of the soil and other factors known to those skilled in plant science. It will be found, however, that the optimum application rate is in the range of from about 0.1 to about 20 kg./ha. in virtually every case. The optimum rates will usually be found to be within the preferred range of from about 0.1 to about 5 kg./ha. Another preferred range, for flooded transplant rice cropland, is from about 0.025 to about 2 kg./ha.

The time when the compounds should be applied to the soil or the weeds is widely variable, since the compounds are effective both preemergence and postemergence. At least some control of weeds will result from application of the compounds at any time when weeds are growing or germinating. They may also be applied to the soil during a dormant season to kill weeds germinating during the following warm season.

The compounds' efficacy against aquatic weeds is analogous to the efficacy against terrestrial weeds. The compounds are effective at the same rates of application described above in the general description of the herbicidal method. Accordingly, the herbicidal method of this invention is effective against aquatic weeds, and is carried out in killing aquatic weeds in the same manner that it is used to kill weeds in general.

When the compounds are used for weed control in an annual crop, it is usually best to apply a preemergence application of the compound to the soil at the time the crop is being planted. If the compound is to be soil incorporated, it will usually be applied and incorporated immediately before planting. It if is to be surface applied, it is usually simplest to apply the compound immediately after planting.

The compounds are applied to the soil or to emerged weeds in the manners usual in agriculture. They may be applied to the soil in the form of either water-dispersed or granular formulations, the preparation of which will be discussed below. Usually, water-dispersed formulations will be used for the application of the compounds to emerged weeds. The formulations are applied with any of the many types of sprayers and granular applicators which are in wide use for the distribution of agricultural chemicals over soil or standing vegetation. When a compound is to be soil-incorporated, any of the usual soil incorporation equipment, such as the disc harrow, the power-driven rotary hoe and the like, are effective.

The compounds are normally used in the practice of the method of this invention in the form of the herbicidal compositions which are an important embodiment of the invention. An herbicidal composition of this invention comprises a compound of the invention and an inert carrier. In general, the compositions are formulated in the manners usual in agricultural chemistry, and are novel only because of the vital presence of the novel herbicidal compound.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier and surfactants. The concentration of the compound is usually from about 10 percent to about 90 percent. The inert carrier is usually chosen from among the attapulgite clays, the kaolin clays, the montmorillonite clays, the diatomaceous earths or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

A special type of emulsifiable concentrate composition is used to form invert emulsions. Such emulsions have the aqueous phase dispersed in the oil phase, and have been used for some years in the agricultural chemical industry. They are particularly useful in postemergent and aquatic applications of the compounds, since they adhere very well to foliage, and do not rapidly disperse in water. Thus, by simple adjustment of the density, an invert emulsion can be accurately placed at the top or bottom of a body of water. Invert emulsion compositions usually include an inverting oil, a mixture of solvents and surfactants specially balanced to make invert emulsions when combined with water. See U.S. Pat. No. 3,197,229.

Another special type of composition which can be useful for application to water, as for flooded rice or aquatic weed applications, is one which forms a hydrophobic film. Such a composition, when applied to water, tends to spread itself evenly over the water surface, thereby achieving even application of the herbicide, despite any inaccuracy in applying the composition. Such compositions are usually based on a hydrophobic liquid, such as xylene, for example, in which the herbicide is dissolved or suspended.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product. Granules are also particularly useful in aquatic weed applications.

It has been customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable and convenient.

Certain of the compounds have other biological activities, as well as herbicidal activity. For example, some of the pyridones of this invention control viruses which cause diseases of humans and domestic animals. Insecticidal and arachnicidal activity has also been shown by certain of the compounds, which control, for example, mosquitoes, houseflies, two-spotted spider mites, Mexican bean beetles and like pests.

I claim:
1. A compound of the formula

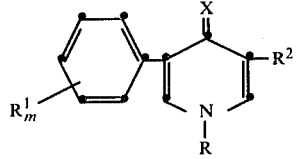

wherein
X represents oxygen or sulfur;
R represents $C_1$-$C_3$ alkyl,
$C_1$-$C_3$ alkyl substituted with halo, cyano, carboxy or methoxycarbonyl,
$C_2$-$C_3$ alkenyl,
$C_2$-$C_3$ alkynyl,
$C_1$-$C_3$ alkoxy,
acetoxy or
dimethylamino,
provided that R comprises no more than 3 carbon atoms;
the $R^1$ groups independently represent halo,
$C_1$-$C_8$ alkyl,
$C_1$-$C_8$ alkyl substituted with halo,
$C_1$-$C_8$ alkyl monosubstituted with phenyl, cyano or $C_1$-$C_3$ alkoxy,
$C_2$-$C_8$ alkenyl,
$C_2$-$C_8$ alkenyl substituted with halo,
$C_2$-$C_8$ alkynyl,
$C_2$-$C_8$ alkynyl substituted with halo,
$C_3$-$C_6$ cycloalkyl,
$C_4$-$C_6$ cycloalkenyl,
$C_4$-$C_8$ cycloalkylalkyl,
$C_1$-$C_3$ alkanoyloxy,
$C_1$-$C_3$ alkylsulfonyloxy,
phenyl,
phenyl monosubstituted with halo, $C_1$-$C_3$ alkyl, $C_1$-$C_3$ alkoxy or nitro,
nitro,
cyano,
carboxy,
hydroxy,
$C_1$-$C_3$ alkoxycarbonyl,
—O—$R^3$,
—S—$R^3$,
—SO—$R^3$ or
—$SO_2$—$R^3$;
$R^3$ represents $C_1$-$C_{12}$ alkyl,
$C_1$-$C_{12}$ alkyl substituted with halo,
$C_1$-$C_{12}$ alkyl monosubstituted with phenyl, cyano or $C_1$-$C_3$ alkoxy,
phenyl,
phenyl monosubstituted with halo, $C_1$-$C_3$ alkyl, $C_1$-$C_3$ alkoxy or nitro,
$C_3$-$C_6$ cycloalkyl,
$C_4$-$C_8$ cycloalkylalkyl,
$C_2$-$C_{12}$ alkenyl,
$C_2$-$C_{12}$ alkenyl substituted with halo,
$C_2$-$C_{12}$ alkynyl or
$C_2$-$C_{12}$ alkynyl substituted with halo,
provided that $R^3$ comprises no more than 12 carbon atoms;
$R^2$ represents halo,
hydrogen,
cyano,
$C_1$-$C_3$ alkoxycarbonyl,
$C_1$-$C_6$ alkyl,
$C_1$-$C_6$ alkyl substituted with halo or $C_1$-$C_3$ alkoxy,
$C_2$-$C_6$ alkenyl,
$C_2$-$C_6$ alkenyl substituted with halo or $C_1$-$C_3$ alkoxy,
$C_2$-$C_6$ alkynyl,
$C_3$-$C_6$ cycloalkyl,
$C_3$-$C_6$ cycloalkyl substituted with halo, $C_1$-$C_3$ alkyl or $C_1$-$C_3$ alkoxy,
$C_4$-$C_6$ cycloalkenyl,
$C_4$-$C_8$ cycloalkylalkyl,
phenyl-$C_1$-$C_3$ alkyl,
furyl,
naphthyl,
thienyl,
—O—$R^4$,
—S—$R^4$, —SO—$R^4$,
—$SO_2$—$R^4$ or

$R^4$ represents $C_1$-$C_3$ alkyl,
$C_1$-$C_3$ alkyl substituted with halo,
$C_2$-$C_3$ alkenyl,
$C_2$-$C_3$ alkenyl substituted with halo,
benzyl,
phenyl or
phenyl substituted with halo, $C_1$-$C_3$ alkyl or $C_1$-$C_3$ alkoxy;
the $R^5$ groups independently represent halo,
$C_1$-$C_8$ alkyl,
$C_1$-$C_8$ alkyl substituted with halo,
$C_1$-$C_8$ alkyl monosubstituted with phenyl, cyano or $C_1$-$C_3$ alkoxy,
$C_2$-$C_8$ alkenyl,
$C_2$-$C_8$ alkenyl substituted with halo,
$C_2$-$C_8$ alkynyl,
$C_2$-$C_8$ alkynyl substituted with halo,
$C_3$-$C_6$ cycloalkyl,
$C_4$-$C_6$ cycloalkenyl,
$C_4$-$C_8$ cycloalkylalkyl,
$C_1$-$C_3$ alkanoyloxy,
$C_1$-$C_3$ alkylsulfonyloxy,
phenyl,
phenyl monosubstituted with halo, $C_1$-$C_3$ alkyl, $C_1$-$C_3$ alkoxy or nitro,
nitro,
cyano,
carboxy,
hydroxy,
$C_1$-$C_3$ alkoxycarbonyl,
—O—$R^6$,
—S—$R^6$,
—SO—$R^6$ or
—$SO_2$—$R^6$;
$R^6$ represents $C_1$-$C_{12}$ alkyl,
$C_1$-$C_{12}$ alkyl substituted with halo,
$C_1$-$C_{12}$ alkyl monosubstituted with phenyl, cyano or $C_1$-$C_3$ alkoxy,
phenyl,
phenyl monosubstituted with halo, $C_1$-$C_3$ alkyl, $C_1$-$C_3$ alkoxy or nitro,
$C_3$-$C_6$ cycloalkyl,
$C_4$-$C_8$ cycloalkylalkyl,
$C_2$-$C_{12}$ alkenyl,
$C_2$-$C_{12}$ alkenyl substituted with halo,
$C_2$-$C_{12}$ alkynyl or
$C_2$-$C_{12}$ alkynyl substituted with halo, provided that $R^6$ comprises no more than 12 carbon atoms;
m and n independently represent 0-2; and the acid addition salts thereof.

2. The compound of claim 1 which is 3-(4-chloro-3-trifluoromethylphenyl)-5-ethoxy-1-methyl-4(1H)-pyridone.

3. The compound of claim 1 which is 1-methyl-3-(4-chloro-3-trifluoromethylphenyl)-5-propyl-4(1H)-pyridone.

4. The compound of claim 1 which is 3-ethyl-1-methyl-5-(4-chloro-3-trifluoromethylphenyl)-4(1H)-pyridone.

5. A compound of claim 1 wherein R represents methyl or ethyl.

6. A compound of claim 5 wherein R represents methyl.

7. A compound of claim 1 of the formula

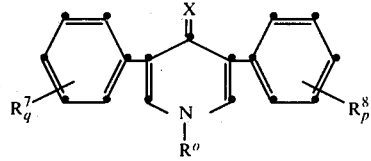

wherein X represents oxygen or sulfur;
$R^o$ represents $C_1$-$C_3$ alkyl, $C_2$-$C_3$ alkenyl, acetoxy or methoxy;
q and p indepdendently represent 0-2; the $R^7$ groups independently represent halo, $C_1$-$C_3$ alkyl, trifluoromethyl or $C_1$-$C_3$ alkoxy;
the $R^8$ groups independently represent halo, $C_1$-$C_3$ alkyl, trifluoromethyl or $C_1$-$C_3$ alkoxy, or two $R^8$ groups occupying adjacent o and m positions combine with the phenyl ring to which they are attached to form a 1-naphthyl group.

8. The compound of claim 7 which is 1-methyl-3-phenyl-5-(3-trifluoromethylphenyl)-4(1H)-pyridone.

9. The compound of claim 7 which is 3-(3-fluorophenyl)-1-methyl-5-phenyl-4(1H)-pyridone.

10. The compound of claim 7 which is 3-(3chlorophenyl)-1-methyl-5-phenyl-4(1H)-pyridone.

11. The compound of claim 7 which is 3,5-bis(3-chlorophenyl)-1-methyl-4(1H)-pyridone.

12. The compound of claim 7 which is 3-(3-chlorophenyl)-5-(3-fluorophenyl)-1-methyl-4(1H)-pyridone.

13. The compound of claim 7 which is 1-methyl-3-(3-methylphenyl)-5-phenyl-4(1H)-pyridone.

14. The compound of claim 7 which is 3,5-diphenyl-1-methyl-4(1H)-pyridone.

15. The compound of claim 7 which is 1-methyl-3,5-bis(3-trifluoromethylphenyl)-4(1H)-pyridone.

16. The compound of claim 7 which is 3-(3-bromophenyl)-1-methyl-5-phenyl-4(1H)-pyridone.

17. The compound of claim 7 which is 3-(3-methoxyphenyl)-1-methyl-5-phenyl-4(1H)-pyridone.

18. The compound of claim 7 which is 3-(3-ethoxyphenyl)-1-methyl-5-phenyl-4(1H)-pyridone.

19. The compound of claim 7 which is 1-methyl-3-phenyl-5-(3-propoxyphenyl)-4(1H)-pyridone.

20. The compound of claim 7 which is 3-(3-isopropoxyphenyl)-1-methyl-5-phenyl-4(1H)-pyridone.

21. The compound of claim 7 which is 3,5-bis(3-fluorophenyl)-1-methyl-4(1H)-pyridone.

22. The compound of claim 7 which is 3-(2-chlorophenyl)-1-methyl-5-(3-trifluoromethylphenyl)-4(1H)-pyridone.

23. The compound of claim 7 which is 3-(3-chlorophenyl)-1-methyl-5-(3-trifluoromethylphenyl)-4(1H)-pyridone.

24. The compound of claim 7 which is 3-(4-chlorophenyl)-1-methyl-5-(3-trifluoromethylphenyl)-4(1H)-pyridone.

25. The compound of claim 7 which is 3-(2-fluorophenyl)-1-methyl-5-(3-trifluoromethylphenyl)-4(1H)-pyridone.

26. The compound of claim 7 which is 3-(3-fluorophenyl)-1-methyl-5-(3-trifluoromethylphenyl)-4(1H)-pyridone.

27. The compound of claim 7 which is 3-(4-fluorophenyl)-1-methyl-5-(3-trifluoromethylphenyl)-4(1H)-pyridone.

28. The compound of claim 7 which is 3-(3-chlorophenyl)-5-(4-chlorophenyl)-1-methyl-4(1H)-pyridone.

29. The compound of claim 7 which is 1-ethyl-3-phenyl-5-(3-trifluoromethylphenyl)-4(1H)-pyridone.

30. The compound of claim 7 which is 1-methyl-3-phenyl-5-(3-trifluoromethylphenyl)-4(1H)-pyridinethione.

31. The compound of claim 7 which is 3-(4-chloro-3-trifluoromethylphenyl)-1-methyl-5-phenyl-4(1H)-pyridone.

32. The compound of claim 7 which is 3-(2-chlorophenyl)-5-(3-chlorophenyl)-1-methyl-4(1H)-pyridone.

33. The compound of claim 7 which is 3-(3-bromophenyl)-5-(3-chlorophenyl)-1-methyl-4(1H)-pyridione.

34. The compound of claim 7 which is 3-(3-bromophenyl)-1-methyl-5-(2-methylphenyl)-4(1H)-pyridone.

35. The compound of claim 7 which is 3-(3-chlorophenyl)-1-methyl-5-(2-methylphenyl)-4(1H)-pyridone.

36. The compound of claim 7 which is 1-methyl-3,5-bis(3-methylphenyl)-4(1H)-pyridone.

37. A compound of claim 7 wherein $R^0$ represents methyl.

38. A compound of claim 37 wherein $R^0$ represents methyl.

39. A compound of claim 1 wherein m represents 1, and the $R^1$ group is located at the meta position.

40. A compound of claim 39 wherein R represents methyl or ethyl.

41. A compound of claim 40 wherein R represents methyl.

42. A compound of claim 39 wherein X represents oxygen.

43. The compound of claim 42 which is 1-methyl-3-phenyl-5-[3-(1,1,2,2-tetrafluoroethoxy)phenyl]-4(1H)pyridone.

44. The compound of claim 42 which is 3-(3-isobutylphenyl)-1-methyl-5-phenyl-4(1H)-pyridone.

45. A compound of claim 42 wherein $R^1$ represents trifluoromethyl.

46. The compound of claim 45 which is 1-methyl-3-(3-trifluoromethylphenyl)-4(1H)-pyridone.

47. The compound of claim 45 which is 3-chloro-1-methyl-5-(3-trifluoromethylphenyl)-4(1H)-pyridone.

48. The compound of claim 45 which is 3-bromo-1-methyl-5-(3-trifluoromethylphenyl)-4(1H)-pyridone.

49. The compound of claim 45 which is 1,3-dimethyl-5-(3-trifluoromethylphenyl)-4(1H)-pyridone.

50. The compound of claim 45 which is 3-ethyl-1-methyl-5-(3-trifluoromethylphenyl)-4(1H)-pyridine.

51. The compound of claim 45 which is 3-isopropyl-1-methyl-5-(3-trifluoromethylphenyl)-4(1H)-pyridone.

52. The compound of claim 45 which is 1-methyl-3-allylthio-5-(3-trifluoromethylphenyl)-4(1H)-pyridone.

53. The compound of claim 45 which is 3-ethylsulfinyl-1-methyl-5-(3-trifluoromethylphenyl)-4(1H)-pyridone.

54. The compound of claim 45 which is 1-methyl-3-(3-trifluoromethylphenyl)-5-trifluoromethylthio-4(1H)-pyridone.

55. The compound of claim 45 which is 1-methyl-3-(2-chloro-4-fluorophenyl)-5-(3-trifluoromethylphenyl)-4(1H)-pyridone.

56. The compound of claim 45 which is 3-(2,5-dimethylphenyl)-1-methyl-5-(3-trifluoromethylphenyl)-4(1H)-pyridone.

57. The compound of claim 45 which is 3-(3,4-dimethylphenyl)-1-methyl-5-(3-trifluoromethylphenyl)4(1H)-pyridone.

58. The compound of claim 45 which is 3-(2-bromophenyl)-1-methyl-5-(3-trifluoromethylphenyl)-4(1H)-pyridone.

59. The compound of claim 45 which is 1-methyl-3-(2-methylphenyl)-5-(3-trifluoromethylphenyl)-4(1H)-pyridone.

60. The compound of claim 45 which is 3-(2-ethylphenyl)-1-methyl-5-(3-trifluoromethylphenyl)-4(1H)-pyridone.

61. The compound of claim 45 which is 1-methyl-3-(2-trifluoromethylphenyl)-5-(3-trifluoromethylphenyl)-4(1H)-pyridone.

62. The compound of claim 45 which is 3-(2-methoxyphenyl)-1-methyl-5-(3-trifluoromethylphenyl)-4(1H)-pyridone.

63. The compound of claim 45 which is 3-(3-bromophenyl)-1-methyl-5-(3-trifluoromethylphenyl)-4(1H)-pyridone.

64. The compound of claim 45 which is 1-methyl-3-(3-methylphenyl)-5-(3-trifluoromethylphenyl-4(1H)-pyridone.

65. The compound of claim 45 which is 1-methyl-3-(4-methylphenyl)-5-(3-trifluoromethylphenyl)-4(1H)-pyridone.

66. The compound of claim 45 which is 1-methyl-3-propyl-5-(3-trifluoromethylphenyl)-4(1H)-pyridone.

67. The compound of claim 45 which is 3-methoxy-1-methyl-5-(3-trifluoromethylphenyl)-4(1H)-pyridone.

68. The compound of claim 45 which is 3-ethoxy-1-methyl-5-(3-trifluoromethylphenyl)-4(1H)-pyridone.

69. The compound of claim 45 which is 3-isopropoxy-1-methyl-5-(3-trifluoromethylphenyl)-4(1H)-pyridone.

70. The compound of claim 45 which is 1-methyl-3-phenoxy-5-(3-trifluoromethylphenyl)-4(1H)-pyridone.

71. The compound of claim 45 which is 3-ethylthio-1-methyl-5-(3-trifluoromethylphenyl)-4(1H)-pyridone.

72. The compound of claim 45 which is 1-methyl-3-propylthio-5-(3-trifluoromethylphenyl)-4(1H)-pyridone.

73. The compound of claim 45 which is 1-methyl-3-isopropylthio-5-(3-trifluoromethylphenyl)-4(1H)-pyridone.

74. The compound of claim 45 which is 1-methyl-3-(3-methylthiophenyl)-5-(3-trifluoromethylphenyl)-4(1H)-pyridone.

75. The compound of claim 45 which is 1,3-diethyl-5-(3-trifluoromethylphenyl)-4(1H)-pyridone.

76. The compound of claim 45 which is 1-ethyl-3,5-bis(3-trifluoromethylphenyl)-4(1H)-pyridone.

77. A compound of claim 45 wherein R represents methyl or ethyl.

78. A compound of claim 77 wherein R represents methyl.

79. A compound of claim 1 of the formula

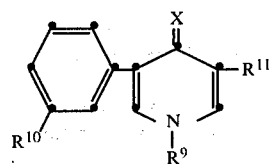

wherein
X represents oxygen or sulfur;

R⁹ represents $C_1-C_3$ alkyl;

R¹⁰ represents hydrogen, trifluoromethyl, $C_1-C_3$ alkyl, halo, methoxy or methylthio;

R¹¹ represents $C_1-C_4$ alkyl, $C_1-C_3$ alkoxy, $C_1-C_3$ alkylthio, phenyl, phenoxy, phenylthio, or phenyl, phenoxy or phenylthio monosubstituted with trifluoromethyl, $C_1-C_3$ alkyl, halo, methoxy or methylthio.

80. A compound of claim 79 wherein R⁹ represents methyl or ethyl.

81. A compound of claim 80 wherein R⁹ represents methyl.

82. A compound of claim 79 wherein X represents oxygen.

83. The compound of claim 82 which is 1-methyl-3-(3-methylthiophenyl)-5-phenyl-4(1H)-pyridone.

84. A compound of claim 79 wherein X represents sulphur.

85. A compound of claim 84 wherein R⁹ represents methyl or ethyl.

86. A compound of claim 85 wherein R⁹ represents methyl.

87. An herbicidal method of selectively killing weeds which comprises contacting the weeds with an herbicidally-effective amount of a compound of claim 1.

88. A method of claim 87 wherein the amount of the compound is from about 0.1 to about 20 kg./ha.

89. A method of claim 88 wherein the compound is 3-(4-chloro-3-trifluoromethylphenyl)-5-ethoxy-1-methyl-4(1H)-pyridone.

90. A method of claim 88 wherein the compound is 1-methyl-3-(4-chloro-3-trifluoromethylphenyl)-5-propyl-4(1H)-pyridone.

91. A method of claim 88 wherein the compound is 3-ethyl-1-methyl-5-(4-chloro-3-trifluoromethylphenyl)-4(1H)-pyridone.

92. A method of claim 88 wherein the amount of the compound is from about 0.1 to about 5 kg./ha.

93. A method of claim 92 wherein the weeds are in the soil of cotton cropland.

94. A method of claim 87 wherein the weeds are in the soil of rice cropland.

95. A method of claim 94 wherein the rice is in flooded transplant culture, and the compound is applied at from the 0.025 to about 2 kg./ha.

96. A method of claim 88 wherein the compound is a compound of the formula

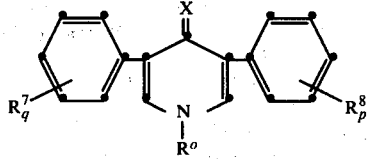

wherein X represents oxygen or sulfur;

R° represents $C_1-C_3$ alkyl, $C_2-C_3$ alkenyl, acetoxy or methoxy;

q and p independently represent 0-2;

the R⁷ groups independently represent halo, $C_1-C_3$ alkyl, trifluoromethyl or $C_1-C_3$ alkoxy; the R⁸ groups independently represent halo, $C_1-C_3$ alkyl, trifluoromethyl or $C_1-C_3$ alkoxy, or two R⁸ groups occupying adjacent o and m positions combine with the phenyl ring to which they are attached to form a 1-naphthyl group.

97. A method of claim 96 wherein the weeds are herbaceous weeds.

98. A method of claim 96 wherein the amount of the compound is from about 0.1 to about 5 kg./ha.

99. A method of claim 98 wherein the weeds are in the soil of cotton cropland.

100. A method of claim 98 wherein the weeds are in the soil of rice cropland.

101. A method of claim 96 wherein the compound is 1-methyl-3-phenyl-5-(3-trifluoromethylphenyl)-4(1H)-pyridone.

102. A method of claim 96 wherein the compound is 3-(3-fluorophenyl)-1-methyl-5-phenyl)-4(1H)-pyridone.

103. A method of claim 96 wherein the compound is 3-(3-chlorophenyl)-1-methyl-5-phenyl-4(1H)-pyridone.

104. A method of claim 96 wherein the compound is 3,5-bis(3-chlorophenyl)-1-methyl-4(1H)-pyridone.

105. A method of claim 96 wherein the compound is 3-(3-chlorophenyl)-5-(3-fluorophenyl)-1-methyl-4(1H)pyridone.

106. A method of claim 96 wherein the compound is 1-methyl-3-(3-methylphenyl)-5-phenyl-4(1H)-pyridone.

107. A method of claim 96 wherein the compound is 3,5-diphenyl-1-methyl-4(1H)-pyridone.

108. A method of claim 96 wherein the compound is 1-methyl-3,5-bis(3-trifluoromethylphenyl)-4(1H)-pyridone.

109. A method of claim 96 wherein the compound is 3-(3-bromophenyl)-1-methyl-5-phenyl-4(1H)-pyridone.

110. A method of claim 96 wherein the compound is 3-(3-methoxyphenyl)-1-methyl-5-phenyl-4(1H)-pyridone.

111. A method of claim 96 wherein the compound is 3-(3-ethoxyphenyl)-1-methyl-5-phenyl-4(1H)-pyridone.

112. A method of claim 96 wherein the compound is 1-methyl-3-phenyl-5-(3-propoxyphenyl)-4(1H)-pyridone.

113. A method of claim 96 wherein the compound is 3-(3-isopropoxyphenyl)-1-methyl-5-phenyl-4(1H)-pyridone.

114. A method of claim 96 wherein the compound is 3,5-bis(3-fluorophenyl)-1-methyl-4(1H)-pyridone.

115. A method of claim 96 wherein the compound is 3-(2-chlorophenyl)-1-methyl-5-(3-trifluoromethylphenyl)-4(1H)-pyridone.

116. A method of claim 96 wherein the compound is 3-(3-chlorophenyl)-1-methyl-5-(3-trifluoromethylphenyl)-4(1H)-pyridone.

117. A method of claim 96 wherein the compound is 3-(4-chlorophenyl)-1-methyl-5-(3-trifluoromethylphenyl)-4(1H)-pyridone.

118. A method of claim 96 wherein the compound is 3-(2-fluorophenyl)-1-methyl-5-(3-trifluoromethylphenyl)-4(1H)-pyridone.

119. A method of claim 96 wherein the compound is 3-(3-fluorophenyl)-1-methyl-5-(3-trifluoromethylphenyl)-4(1H)-pyridone.

120. A method of claim 96 wherein the compound is 3-(4-fluorophenyl)-1-methyl-5-(3-trifluoromethylphenyl)-4(1H)-pyridone.

121. A method of claim 96 wherein the compound is 3-(3-chlorophenyl)-5-(4-chlorophenyl)-1-methyl-4(1H)-pyridone.

122. A method of claim 96 wherein the compound is 1-ethyl-3-phenyl-5-(3-trifluoromethylphenyl)-4(1H)-pyridone.

123. A method of claim 96 wherein the compound is 1-methyl-3-phenyl-5-(3-trifluoromethylphenyl)-4(1H)-pyridinethione.

124. A method of claim 96 wherein the compound is 3-(4-chloro-3-trifluoromethylphenyl)-1-methyl-5-phenyl-4(1H)-pyridone.

125. A method of claim 96 wherein the compound is 3-(2-chlorophenyl)-5-(3-chlorophenyl)-1-methyl-4(1H)-pyridone.

126. A method of claim 96 wherein the compound is 3-(3-bromophenyl)-5-(3-chlorophenyl)-1-methyl-4(1H)-pyridone.

127. A method of claim 96 wherein the compound is 3-(3-bromophenyl)-1-methyl-5-(2-methylphenyl)-4(1H)-pyridone.

128. A method of claim 96 wherein the compound is 3-(3-chlorophenyl)-1-methyl-5-(2-methylphenyl)-4(1H)-pyridone.

129. A method of claim 96 wherein the compound is 1-methyl-3,5-bis(3-methylphenyl)-4(1H)-pyridone.

130. A method of claim 96 wherein the compound is a compound wherein $R^0$ represents methyl or ethyl.

131. A method of claim 88 wherein the compound is a compound wherein m represents 1, and the $R^1$ group is located at the meta position.

132. A method of claim 131 wherein the compound is a compound wherein X represents oxygen.

133. A method of claim 132 wherein the compound is 1-methyl-3-phenyl-5-[3-(1,1,2,2-tetrafluoroethoxy)phenyl]-4(1H)-pyridone.

134. A method of claim 132 wherein the compound is 3-(3-isobutylphenyl)-1-methyl-5-phenyl-4(1H)-pyridone.

135. A method of claim 132 wherein the compound is a compound wherein $R^1$ represents trifluoromethyl.

136. A method of claim 135 wherein the compound is 1-methyl-3-(3-trifluoromethylphenyl)-4(1H)-pyridone.

137. A method of claim 135 wherein the compound is 3-chloro-1-methyl-5-(3-trifluoromethylphenyl)-4(1H)-pyridone.

138. A method of claim 135 wherein the compound is 3-bromo-1-methyl-5-(3-trifluoromethylphenyl)-4(1H)-pyridone.

139. A method of claim 135 wherein the compound is 1,3-dimethyl-5-(3-trifluoromethylphenyl)-4(1H)-pyridone.

140. A method of claim 135 wherein the compound is 3-ethyl-1-methyl-5-(3-trifluoromethylphenyl)-4(1H)-pyridone.

141. A method of claim 135 wherein the compound is 3-isopropyl-1-methyl-5-(3-trifluoromethylphenyl)-4(1H)-pyridone.

142. A method of claim 135 wherein the compound is 1-methyl-3-allylthio-5-(3-trifluoromethylphenyl)-4(1H)-pyridone.

143. A method of claim 135 wherein the compound is 3-ethylsulfinyl-1-methyl-5-(3-trifluoromethylphenyl)-4(1H)-pyridone.

144. A method of claim 135 wherein the compound is 1-methyl-3(3trifluoromethylphenyl)-5;-trifluoromethylthio-4(1H)-pyridone.

145. A method of claim 135 wherein the compound is 1-methyl-3-(2-chloro-4-fluorophenyl)-5-(3-trifluoromethylphenyl)-4(1H)-pyridone.

146. A method of claim 135 wherein the compound is 3-(2,5-dimethylphenyl)-1-methyl-5-(3-trifluoromethylphenyl)-4(1H)-pyridone.

147. A method of claim 135 wherein the compound is 3-(3,4-dimethylphenyl)-1-methyl-5-(3-trifluoromethylphenyl)-4(1H)-pyridone.

148. A method of claim 135 wherein the compound is 3-(2-bromophenyl)-1-methyl-5-(3-trifluoromethylphenyl)-4(1H)-pyridone.

149. A method of claim 135 wherein the compound is 1-methyl-3-(2-methylphenyl)-5-(3-trifluoromethylphenyl)-4(1H)-pyridone.

150. A method of claim 135 wherein the compound is 3-(2-ethylphenyl)-1-methyl-5-(3-trifluoromethylphenyl)-4(1H)-pyridone.

151. A method of claim 135 wherein the compound is 1-methyl-3-(2-trifluoromethylphenyl)-5-(3-trifluoromethylphenyl)-4(1H)-pyridone.

152. A method of claim 135 wherein the compound is 3-(2-methoxyphenyl)-1-methyl-5-(3-trifluoromethylphenyl)-4(1H)-pyridone.

153. A method of claim 135 wherein the compound is 3-(3-bromophenyl)-1-methyl-5-(3-trifluoromethylphenyl)-4(1H)-pyridone.

154. A method of claim 135 wherein the compound is 1-methyl-3-(3-methylphenyl)-5-(3-trifluoromethylphenyl)-4(1H)-pyridone.

155. A method of claim 135 wherein the compound is 1-methyl-3-(4-methylphenyl)-5-(3-trifluoromethylphenyl)-4(1H)-pyridone.

156. A method of claim 135 wherein the compound is 1-methyl-3-propyl-5-(3-trifluoromethylphenyl)-4(1H)-pyridone.

157. A method of claim 135 wherein the compound is 3-methoxy-1-methyl-5-(3-trifluoromethylphenyl)-4(1H)-pyridone.

158. A method of claim 135 wherein the compound is 3-ethoxy-1-methyl-5-(3-trifluoromethylphenyl)-4(1H)-pyridone.

159. A method of claim 135 wherein the compound is 3-isopropoxy-1-methyl-5-(3-trifluoromethylphenyl)-4(1H)-pyridone.

160. A method of claim 135 wherein the compound is 1-methyl-3-phenoxy-5-(3-trifluoromethylphenyl)-4(1H)-pyridone.

161. A method of claim 135 wherein the compound is 3-ethylthio-1-methyl-5-(3-trifluoromethylphenyl)-4(1H)-pyridone.

162. A method of claim 135 wherein the compound is 1-methyl-3-propylthio-5-(3-trifluoromethylphenyl)-4(1H)-pyridone.

163. A method of claim 135 wherein the compound is 1-methyl-3-isopropylthio-5-(3-trifluoromethylphenyl)-4(1H)-pyridone.

164. A method of claim 135 wherein the compound is 1-methyl-3-(3-methylthiophenyl)-5-(3-trifluoromethylphenyl)-4(1H)-pyridone.

165. A method of claim 135 wherein the compound is 1,3-diethyl-5-(3-trifluoromethylphenyl)-4(1H)-pyridone.

166. A method of claim 135 wherein the compound is 1-ethyl-3,5-bis(3-trifluoromethylphenyl)-4(1H)-pyridone.

167. A method of claim 135 wherein the compound is a compound wherein R represents methyl or ethyl.

168. A method of claim 97 wherein the compound is 1-methyl-3-phenyl-5-(3-trifluoromethylphenyl)-4(1H)-pyridone.

169. A method of claim 97 wherein the compound is 3-(3-fluorophenyl)-1-methyl-5-phenyl-4(1H)-pyridone.

170. A method of claim 97 wherein the compound is 3-(3-chlorophenyl)-1-methyl-5-phenyl-4(1H)-pyridone.

171. A method of claim 97 wherein the compound is 3,5-bis(3-chlorophenyl)-1-methyl-4(1H)-pyridone.

172. A method of claim 97 wherein the compound is 3-(3-chlorophenyl)-5-(3-fluorophenyl)-1-methyl-4(1H)-pyridone.

173. A method of claim 97 wherein the compound is 1-methyl-3-(3-methylphenyl)-5-phenyl-4(1H)-pyridone.

174. A method of claim 97 wherein the compound is 3,5-diphenyl-1-methyl-4(1H)-pyridone.

175. A method of claim 97 wherein the compound is 1-methyl-3,5-bis(3-trifluoromethylphenyl)-4(1H)-pyridone.

176. A method of claim 87 wherein the compound is of the formula

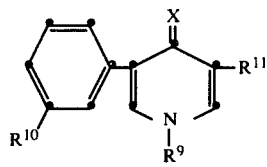

wherein X represents oxygen or sulfur;
$R^9$ represents $C_1$–$C_3$ alkyl;
$R^{10}$ represents hydrogen, trifluoromethyl, $C_1$–$C_3$ alkyl, halo, methoxy or methylthio;
$R^{11}$ represents $C_1$–$C_4$ alkyl, $C_1$–$C_3$ alkoxy, $C_1$–$C_3$ alkylthio, phenyl, phenoxy, phenylthio, or phenyl, phenoxy or phenylthio monosubstituted with trifluoromethyl, $C_1$–$C_3$ alkyl, halo, methoxy or methylthio.

177. A method of claim 176 wherein the weeds are in the soil of cotton cropland.

178. A method of claim 176 wherein the weeds are in the soil of rice cropland.

179. A method of claim 177 wherein the compound is applied at from about 0.1 to about 5 kg./ha.

180. A method of claim 178 wherein the rice is in flooded transplant culture, and the compound is applied at from about 0.025 to about 2 kg./ha.

181. A method of claim 176 wherein the compound is a compound wherein $R^9$ represents methyl or ethyl.

182. A method of claim 181 wherein the compound is a compound wherein X represents oxygen.

183. A method of claim 182 wherein the compound is 1-methyl-3-(3-methylthiophenyl)-5-phenyl-4(1H)-pyridone.

184. A method of claim 176 wherein the compound is a compound wherein X represents sulphur.

185. A method of claim 184 wherein the compound is a compound wherein $R^9$ represents methyl or ethyl.

186. A method of claim 185 wherein the compound is a compound wherein $R^9$ represents methyl.

187. An herbicidal composition which comprises an inert carrier and a compound of claim 1.

188. A composition of claim 187 wherein the compound is 3-(4-chloro-3-trifluoromethylphenyl)-5-ethoxy-1-methyl-4(1H)-pyridone.

189. A composition of claim 187 wherein the compound is 1-methyl-3-(4-chloro-3-trifluoromethylphenyl)-5-propyl-4(1H)-pyridone.

190. A composition of claim 187 wherein the compound is 3-ethyl-1-methyl-5-(4-chloro-3-trifluoromethylphenyl)-4(1H)-pyridone.

191. A composition of claim 187 wherein the compound is a compound wherein R represents methyl or ethyl.

192. The composition of claim 191 wherein the compound is a compound wherein R represents methyl.

193. A composition of claim 187 wherein the compound is a compound of the formula

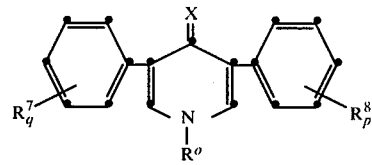

wherein X represents oxygen or sulfur;
$R^o$ represents $C_1$–$C_3$ alkyl, $C_2$–$C_3$ alkenyl, acetoxy or methoxy;
q and p independently represent 0–2;
the $R^7$ groups independently represent halo, $C_1$–$C_3$ alkyl, trifluoromethyl or $C_1$–$C_3$ alkoxy;
the $R^8$ groups independently represent halo, $C_1$–$C_3$ alkyl, trifluoromethyl or $C_1$–$C_3$ alkoxy, or two $R^8$ groups occupying adjacent o and m positions combine with the phenyl ring to which they are attached to form a 1-naphthyl group.

194. A composition of claim 193 wherein the compound is 1-methyl-3-phenyl-5-(3-trifluoromethylphenyl)-4(1H)-pyridone.

195. A composition of claim 193 wherein the compound is 3-(3-fluorophenyl)-1-methyl-5-phenyl-4(1H)-pyridone.

196. A composition of claim 193 wherein the compound is 3-(3-chlorophenyl)-1-methyl-5-phenyl-4(1H)-pyridone.

197. A composition of claim 193 wherein the compound is 3,5-bis(3-chlorophenyl)-1-methyl-4(1H)-pyridone.

198. A composition of claim 193 wherein the compound is 3-(3-chlorophenyl)-5-(3-fluorophenyl)-1-methyl-4(1H)-pyridone.

199. A composition of claim 193 wherein the compound is 1-methyl-3-(3-methylphenyl)-5-phenyl-4(1H)-pyridone.

200. A composition of claim 193 wherein the compound is 3,5-diphenyl-1-methyl-4(1H)-pyridone.

201. A compound of claim 193 wherein the compound is 1-methyl-3,5-bis(3-trifluoromethylphenyl)-4(1H)-pyridone.

202. A composition of claim 193 wherein the compound is 3-(3-bromophenyl)-1-methyl-5-phenyl-4(1H)-pyridone.

203. A composition of claim 193 wherein the compound is 3-(3-methoxyphenyl)-1-methyl-5-phenyl-4(1H)-pyridone.

204. A composition of claim 193 wherein the compound is 3-(3-ethoxyphenyl)-1-methyl-5-phenyl-4(1H)-pyridone.

205. A composition of claim 193 wherein the compound is 1-methyl-3-phenyl-5-(3-propoxyphenyl)-4(1H)-pyridone.

206. A composition of claim 193 wherein the compound is 3-(3-isopropoxyphenyl)-1-methyl-5-phenyl-4(1H)-pyridone.

207. A composition of claim 193 wherein the compound is 3,5-bis(3-fluorophenyl)-1-methyl-4(1H)-pyridone.

208. A composition of claim 193 wherein the compound is 3-(2-chlorophenyl)-1-methyl-5-(3-trifluoromethylphenyl)-4(1H)-pyridone.

209. A composition of claim 193 wherein the compound is 3-(3-chlorophenyl)-1-methyl-5-(3-trifluoromethylphenyl)-4(1H)-pyridone.

210. A composition of claim 193 wherein the compound is 3-(4-chlorophenyl)-1-methyl-5-(3-trifluoromethylphenyl)-4(1H)-pyridone.

211. A composition of claim 193 wherein the compound is 3-(2-fluorophenyl)-1-methyl-5-(3-trifluoromethylphenyl)-4(1H)-pyridone.

212. A composition of claim 193 wherein the compound is 3-(3-fluorophenyl)-1-methyl-5-(3-trifluoromethylphenyl)-4(1H)-pyridone.

213. A composition of claim 193 wherein the compound is 3-(4-fluorophenyl)-1-methyl-5-(3-trifluoromethylphenyl)-4(1H)-pyridone.

214. A composition of claim 193 wherein the compound is 3-(3-chlorophenyl)-5-(4-chlorophenyl)-1-methyl-4(1H)-pyridone.

215. A composition of claim 193 wherein the compound is 1-ethyl-3-phenyl-5-(3-trifluoromethylphenyl)-4(1H)-pyridone.

216. A composition of claim 193 wherein the compound is 1-methyl-3-phenyl-5-(3-trifluoromethylphenyl)-4(1H)-pyridone.

217. A composition of claim 193 wherein the compound is 3-(4-chloro-3-trifluoromethylphenyl)-1-methyl-5-phenyl-4(4H)-pyridone.

218. A composition of claim 193 wherein the compound is 3-(2-chlorophenyl)-5-(3-chlorophenyl)-1-methyl-4(1H)-pyridone.

219. A composition of claim 193 wherein the compound is 3-(3-bromophenyl)-5-(3-chlorophenyl)-1-methyl-4(1H)-pyridone.

220. A composition of claim 193 wherein the compound is 3-(3-bromophenyl)-1-methyl-5-(2-methylphenyl)-4(1H)-pyridone.

221. A composition of claim 193 wherein the compound is 3-(3-chlorophenyl)-1-methyl-5-(2-methylphenyl)-4(1H)-pyridone.

222. A composition of claim 193 wherein the compound is 1-methyl-3,5-bis(3-methylphenyl)-4(1H)-pyridone.

223. A composition of claim 193 wherein the compound is a compound wherein R° represents methyl or ethyl.

224. A composition of claim 223 wherein the compound is a compound wherein R° represents methyl.

225. A composition of claim 187 wherein the compound is a compound wherein m represents 1, and the $R^1$ group is located at the meta position.

226. A composition of claim 225 wherein the compound is a compound wherein R represents methyl or ethyl.

227. A composition of claim 226 wherein the compound is a compound wherein R represents methyl.

228. A composition of claim 225 wherein the compound is a compound wherein X represents oxygen.

229. A composition of claim 228 wherein the compound is 1-methyl-3-phenyl-5-[3-(1,1,2,2-tetrafluoroethoxy)phenyl]-4(1H)-pyridone.

230. A composition of claim 228 wherein the compound is 3-(3-isobutylphenyl)-1-methyl-5-phenyl-4(1H)-pyridone.

231. A composition of claim 228 wherein the compound is a compound wherein $R^1$ represents trifluoromethyl.

232. A composition of claim 231 wherein the compound is 1-methyl-3-(3-trifluoromethylphenyl)-4(1H)-pyridone.

233. A composition of claim 231 wherein the compound is 3-chloro-1-methyl-5-(3-trifluoromethylphenyl)-4(1H)-pyridone.

234. A composition of claim 231 wherein the compound is 3-bromo-1-methyl-5-(3-trifluoromethylphenyl)-4(1H)-pyridone.

235. A composition of claim 231 wherein the compound is 1,3-dimethyl-5-(3-trifluoromethylphenyl)-4(1H)-pyridone.

236. A composition of claim 231 wherein the compound is 3-ethyl-1-methyl-5-(3-trifluoromethylphenyl)-4(1H)-pyridone.

237. A composition of claim 231 wherein the compound is 3-isopropyl-1-methyl-5-(3-trifluoromethylphenyl)-4(1H)-pyridone.

238. A composition of claim 231 wherein the compound is 1-methyl-3-allylthio-5-(3-trifluoromethylphenyl)-4(1H)-pyridone.

239. A composition of claim 231 wherein the compound is 3-ethylsulfinyl-1-methyl-5-(3-trifluoromethylphenyl)-4(1H)-pyridone.

240. A composition of claim 231 wherein the compound is 1-methyl-3-(3-trifluoromethylphenyl)-5-trifluoromethylthio-4(1H)-pyridone.

241. A composition of claim 231 wherein the compound is 1-methyl-3-(2-chloro-4-fluorophenyl)-5-(3-trifluoromethylphenyl)-4(1H)-pyridone.

242. A composition of claim 231 wherein the compound is 3-(2,5-dimethylphenyl)-1-methyl-5-(3-trifluoromethylphenyl)-4(1H)-pyridone.

243. A composition of claim 231 wherein the compound is 3-(3,4-dimethylphenyl)-1-methyl-5-(3-trifluoromethylphenyl)-4(1H)-pyridone.

244. A composition of claim 231 wherein the compound is 3-(2-bromophenyl)-1-methyl-5-(3-trifluoromethylphenyl)-4(1H)-pyridone.

245. A composition of claim 231 wherein the compound is 1-methyl-3-(2-methylphenyl)-5-(3-trifluoromethylphenyl)-4(1H)-pyridone.

246. A composition of claim 231 wherein the compound is 3-(2-ethylphenyl)-1-methyl-5-(3-trifluoromethylphenyl)-4(1H)-pyridone.

247. A composition of claim 231 wherein the compound is 1-methyl-3-(2-trifluoromethylphenyl)-5-(3-trifluoromethylphenyl)-4(1H)-pyridone.

248. A composition of claim 231 wherein the compound is 3-(2-methoxyphenyl)-1-methyl-5-(3-trifluoromethylphenyl)-4(1H)-pyridone.

249. A composition of claim 231 wherein the compound is 3-(3-bromophenyl)-1-methyl-5-(3-trifluoromethylphenyl)-4(1H)-pyridone.

250. A composition of claim 231 wherein the compound is 1-methyl-3-(3-methylphenyl)-5-(3-trifluoromethylphenyl)-4(1H)-pyridone.

251. A composition of claim 231 wherein the compound is 1-methyl-3-(4-methylphenyl)-5-(3-trifluoromethylphenyl)-4(1H)-pyridone.

252. A composition of claim 231 wherein the compound is 1-methyl-3-propyl-5-(3-trifluoromethylphenyl)-4(1H)-pyridone.

253. A composition of claim 231 wherein the compound is 3-methoxy-1-methyl-5-(3-trifluoromethylphenyl)-4(1H)-pyridone.

254. A composition of claim 231 wherein the compound is 3-ethoxy-1-methyl-5-(3-trifluoromethylphenyl)-4(1H)-pyridone.

255. A composition of claim 231 wherein the compound is 3-isopropoxy-1-methyl-5-(3-trifluoromethylphenyl)-4(1H)-pyridone.

256. A composition of claim 231 wherein the compound is 1-methyl-3-phenoxy-5-(3-trifluoromethylphenyl)-4(1H)-pyridone.

257. A composition of claim 231 wherein the compound is 3-ethylthio-1-methyl-5-(3-trifluoromethylphenyl)-4(1H)-pyridone.

258. A composition of claim 231 wherein the compound is 1-methyl-3-propylthio-5-(3-trifluoromethylphenyl)-4(1H)-pyridone.

259. A composition of claim 231 wherein the compound is 1-methyl-3-isopropylthio-5-(3-trifluoromethylphenyl)-4(1H)-pyridone.

260. A composition of claim 231 wherein the compound is 1-methyl-3-(3-methylthiophenyl)-5-(3-trifluoromethylphenyl)-4(1H)-pyridone.

261. A composition of claim 231 wherein the compound is 1,3-diethyl-5-(3-trifluoromethylphenyl)-4(1H)-pyridone.

262. A composition of claim 231 wherein the compound is 1-ethyl-3,5-bis(3-trifluoromethylphenyl)-4(1H)-pyridone.

263. A composition of claim 231 wherein the compound is a compound wherein R represents methyl or ethyl.

264. A composition of claim 263 wherein the compound is a compound wherein R represents methyl.

265. A composition of claim 187 wherein the compound is of the formula

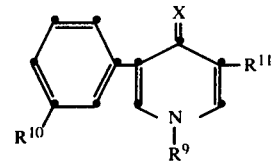

wherein
X represents oxygen or sulfur;
$R^9$ represents $C_1$–$C_3$ alkyl;
$R^{10}$ represents hydrogen, trifluoromethyl, $C_1$–$C_3$ alkyl, halo, methoxy or methylthio;
$R^{11}$ represents $C_1$–$C_4$ alkyl, $C_1$–$C_3$ alkoxy, $C_1$–$C_3$ alkylthio, phenyl, phenoxy, phenylthio, or phenyl, phenoxy or phenylthio monosubstituted with trifluoromethyl, $C_1$–$C_3$ alkyl, halo, methoxy or methylthio.

266. A composition of claim 265 wherein the compound is a compound wherein $R^9$ represents methyl or ethyl.

267. A composition of claim 266 wherein the compound is a compound wherein $R^9$ represents methyl.

268. A composition of claim 265 wherein the compound is a compound wherein X represents oxygen.

269. A composition of claim 268 wherein the compound is 1-methyl-3-(3-methylthiophenyl)-5-phenyl-4(1H)-pyridone.

270. A composition of claim 265 wherein the compound is a compound wherein X represents sulphur.

271. A composition of claim 270 wherein the compound is a compound wherein $R^9$ represents methyl or ethyl.

272. A composition of claim 271 wherein the compound is a compound wherein $R^9$ represents methyl.

* * * * *

UNITED STATES PATENT AND TRADEMARK OFFICE
CERTIFICATE OF CORRECTION

PATENT NO. : 4,152,136

DATED : May 1, 1979

INVENTOR(S) : Harold M. Taylor

It is certified that error appears in the above-identified patent and that said Letters Patent are hereby corrected as shown below:

Column 17, line 37, "form" should read --from--.

Column 39, line 47,"(3-methylthiphenyl)" should read --(3-methylthiophenyl)--.

In Table 2, column 51, line 1 of the table, the Example No. should read --1--.

In Table 2, columns 51 and 52, the next line after Example No. 38 insert
--39, 2, 4, 3, 3, 2, 2, 1, 3, 5, 5, 5, 5, 3, 3--
under the appropriate columns.

In Table 2, Column 52, last column of Example No. 54 insert --2--.

In Table 2, column 54, last column of Example No. 122 insert --1--.

In Table 3, column 58, in Example No. 26 under the column titled Cucumber, insert --1--.

In Table 3, column 59, last column of Example No. 54 insert --1--.

Column 75, line 62, last column of Example No. 51, insert --10--.

Column 80, line 65, "surghum" should read --sorghum--.

Column 83, line 37, "been" should read --become--.

UNITED STATES PATENT AND TRADEMARK OFFICE
CERTIFICATE OF CORRECTION

PATENT NO. : 4,152,136

DATED : May 1, 1979

INVENTOR(S) : Harold M. Taylor

It is certified that error appears in the above-identified patent and that said Letters Patent are hereby corrected as shown below:

Column 87, line 25, of Claim 37, "methyl." should read --methyl or ethyl.--.

Column 95, line 28, of Claim 216, "pyridone." should read --pyridinethione.--

Column 95, line 31, of Claim 217, "4(4H)" should read --4(1H)--.

Signed and Sealed this

Twenty-ninth Day of January 1980

[SEAL]

Attest:

SIDNEY A. DIAMOND

Attesting Officer

Commissioner of Patents and Trademarks